US012162010B2

(12) United States Patent
Parthasarathy

(10) Patent No.: US 12,162,010 B2
(45) Date of Patent: Dec. 10, 2024

(54) BIOLOGICAL FLUID FILTRATION SYSTEM

(71) Applicant: Astrin Biosciences, Inc., Excelsior, MN (US)

(72) Inventor: Jayant Parthasarathy, Excelsior, MN (US)

(73) Assignee: Astrin Biosciences, Inc., St. Paul, MN (US)

( * ) Notice: Subject to any disclaimer, the term of this patent is extended or adjusted under 35 U.S.C. 154(b) by 856 days.

(21) Appl. No.: 17/205,393

(22) Filed: Mar. 18, 2021

(65) Prior Publication Data

US 2021/0237067 A1 Aug. 5, 2021

Related U.S. Application Data

(63) Continuation of application No. 17/162,450, filed on Jan. 29, 2021.

(Continued)

(51) Int. Cl.
*B01L 3/00* (2006.01)
*B01D 46/00* (2022.01)
(Continued)

(52) U.S. Cl.
CPC .... *B01L 3/502753* (2013.01); *B01D 46/0013* (2013.01); *B01D 46/0028* (2013.01);
(Continued)

(58) Field of Classification Search
CPC ......... B01L 3/502753; B01L 3/502715; B01L 2300/0654; B01L 2300/0681;
(Continued)

(56) References Cited

U.S. PATENT DOCUMENTS

| 5,316,725 A | 5/1994 | Carver, Jr. et al. |
| 5,628,727 A | 5/1997 | Hakky et al. |

(Continued)

FOREIGN PATENT DOCUMENTS

| CN | 101629909 B * | 2/2012 | ................ G01J 3/02 |
| EP | 1281951 A1 * | 2/2003 | ............. G01N 15/14 |

(Continued)

OTHER PUBLICATIONS

PCT International Search Report and Written Opinion for PCT Application PCT/US2021/015945; Apr. 21, 2021.
(Continued)

*Primary Examiner* — Matthew D Krcha
*Assistant Examiner* — Sophia Y Lyle
(74) *Attorney, Agent, or Firm* — Lathrop GPM LLP; Lisa Hillman

(57) ABSTRACT

A biological fluid filtration system for scanning a biological fluid so as to filter potentially undesirable constituents from the biological fluid for therapeutic or diagnostic purposes. The biological fluid filtration system generally includes a fluid receiving device adapted to receive a biological fluid. A valve including an inlet, a first outlet, and a second outlet is fluidly connected to the fluid receiving device. The biological fluid within the fluid receiving device is scanned by a scanner to produce scanned data relating to the biological fluid. A control unit in communication with the scanner and the valve receives the scanned data and controls the valve based on the scanned data. The valve is controlled to direct the biological fluid through either the first or second outlet of the valve depending upon the constituents of the biological fluid identified by the control unit.

21 Claims, 55 Drawing Sheets

Related U.S. Application Data

(60) Provisional application No. 62/968,476, filed on Jan. 31, 2020.

(51) Int. Cl.
*B01D 46/24* (2006.01)
*B01D 46/52* (2006.01)
*B01D 46/64* (2022.01)
*B01D 46/70* (2022.01)
*B01D 53/78* (2006.01)

(52) U.S. Cl.
CPC ....... *B01D 46/2414* (2013.01); *B01D 46/522* (2013.01); *B01D 46/64* (2022.01); *B01D 46/70* (2022.01); *B01D 53/78* (2013.01); *B01L 3/502715* (2013.01); *B01L 2300/0654* (2013.01); *B01L 2300/0681* (2013.01)

(58) Field of Classification Search
CPC ............ B01D 46/0013; B01D 46/0028; B01D 46/2414; B01D 46/522; B01D 46/64; B01D 46/70; B01D 53/78; G01N 2015/0294; G01N 15/0227; G01N 15/1425; G01N 15/1429; G01N 2015/1006; G01N 2015/149; G01N 2015/1493; G01N 2015/1497; G01N 15/147; G01N 15/1475; G01N 15/1484; A61B 5/6866
See application file for complete search history.

(56) References Cited

U.S. PATENT DOCUMENTS

| | | |
|---|---|---|
| 8,241,238 B2 | 8/2012 | Hiruma et al. |
| 8,548,219 B2 | 10/2013 | Ortyn et al. |
| 9,422,517 B2 | 8/2016 | Chen et al. |
| 9,458,489 B2 | 10/2016 | Teck et al. |
| 9,545,471 B2 | 1/2017 | Van Rijn et al. |
| 9,808,803 B2 | 11/2017 | Toner et al. |
| 10,073,024 B2 | 9/2018 | Nagrath et al. |
| 10,147,180 B2 | 12/2018 | Couch et al. |
| 10,386,384 B2 | 8/2019 | Hong |
| 10,407,180 B2 | 9/2019 | Morellec et al. |
| 10,519,175 B2 | 12/2019 | Londesbrough et al. |
| 2002/0005354 A1 | 1/2002 | Spence |
| 2002/0033939 A1 | 3/2002 | Hansen |
| 2002/0058332 A1 | 5/2002 | Quake et al. |
| 2002/0182738 A1 | 12/2002 | Connelly et al. |
| 2003/0198523 A1 | 10/2003 | Bohm et al. |
| 2004/0072278 A1 | 4/2004 | Chou |
| 2004/0161143 A1* | 8/2004 | Dietz ................. G01N 15/1475 382/133 |
| 2005/0142570 A1 | 6/2005 | Parthasarathy et al. |
| 2005/0221271 A1 | 10/2005 | Murphy |
| 2005/0255001 A1 | 11/2005 | Padmanabhan et al. |
| 2007/0054350 A1 | 3/2007 | Walker, Jr. |
| 2007/0286254 A1 | 12/2007 | Fon et al. |
| 2008/0038713 A1 | 2/2008 | Gao et al. |
| 2008/0213821 A1 | 9/2008 | Liu et al. |
| 2008/0248499 A1 | 10/2008 | Chiu et al. |
| 2008/0261295 A1 | 10/2008 | Bulter et al. |
| 2009/0198168 A1 | 8/2009 | Hiruma et al. |
| 2011/0003325 A1 | 1/2011 | Durack |
| 2011/0217729 A1 | 9/2011 | Hong et al. |
| 2012/0021453 A1 | 1/2012 | Patra |
| 2012/0129190 A1 | 5/2012 | Chiu et al. |
| 2012/0264646 A1* | 10/2012 | Link .................. C40B 50/08 435/23 |
| 2013/0011210 A1 | 1/2013 | Toner et al. |
| 2013/0171685 A1 | 7/2013 | Schutze et al. |
| 2013/0190202 A1 | 7/2013 | Southern |
| 2013/0314526 A1 | 11/2013 | Yasuda |
| 2014/0074008 A1 | 3/2014 | Fontanazzi et al. |
| 2014/0170735 A1 | 6/2014 | Holmes |
| 2014/0190888 A1 | 7/2014 | Van et al. |
| 2014/0248621 A1 | 9/2014 | Collins et al. |
| 2014/0376816 A1 | 12/2014 | Lagae et al. |
| 2015/0118728 A1 | 4/2015 | Rahmen et al. |
| 2015/0132766 A1 | 5/2015 | Yasuda et al. |
| 2015/0238963 A1 | 8/2015 | Han et al. |
| 2016/0032350 A1 | 2/2016 | Hou et al. |
| 2016/0084814 A1 | 3/2016 | Olson et al. |
| 2016/0106353 A1 | 4/2016 | Schuetz et al. |
| 2016/0146823 A1 | 5/2016 | Chiu |
| 2016/0231274 A1 | 8/2016 | Tirapu Azpiroz et al. |
| 2016/0340636 A1* | 11/2016 | Tabata ................. G01N 15/147 |
| 2017/0003267 A1 | 1/2017 | Meyer et al. |
| 2017/0080142 A1 | 3/2017 | Biran |
| 2017/0122861 A1* | 5/2017 | Lin ..................... G01N 15/147 |
| 2017/0212033 A1 | 7/2017 | Ozaki |
| 2017/0248508 A1 | 8/2017 | Ward et al. |
| 2017/0327783 A1 | 11/2017 | Grummitt et al. |
| 2017/0368373 A1 | 12/2017 | Velayudhan |
| 2018/0104691 A1 | 4/2018 | Merten et al. |
| 2018/0128723 A1 | 5/2018 | Hiruma et al. |
| 2018/0154361 A1 | 6/2018 | Foster et al. |
| 2018/0297085 A1 | 10/2018 | Deshpande et al. |
| 2018/0313816 A1 | 11/2018 | Fiering et al. |
| 2018/0321128 A1 | 11/2018 | Harriman et al. |
| 2018/0334670 A1 | 11/2018 | Bharadwaj et al. |
| 2019/0022652 A1 | 1/2019 | Xie |
| 2019/0151847 A1 | 5/2019 | Bhagat et al. |
| 2019/0195774 A1 | 6/2019 | El-Zehiry |
| 2019/0300928 A1 | 10/2019 | Parthasarathy |
| 2019/0332054 A1 | 10/2019 | Hong |
| 2019/0360915 A1* | 11/2019 | Foster ................. G01N 15/1459 |
| 2019/0369557 A1 | 12/2019 | Lee et al. |
| 2020/0206740 A1 | 7/2020 | Hiu et al. |
| 2020/0222905 A1* | 7/2020 | Hill .................... B01L 3/502784 |
| 2020/0376488 A1 | 12/2020 | Wu |
| 2021/0196767 A1 | 7/2021 | Minami et al. |
| 2021/0237064 A1 | 8/2021 | Parthasarathy |
| 2021/0237065 A1 | 8/2021 | Parthasarathy |
| 2021/0237066 A1 | 8/2021 | Parthasarathy |
| 2021/0237067 A1 | 8/2021 | Parthasarathy |
| 2021/0237068 A1 | 8/2021 | Parthasarathy |
| 2021/0237069 A1 | 8/2021 | Parthasarathy |
| 2021/0237070 A1 | 8/2021 | Parthasarathy |
| 2021/0237071 A1 | 8/2021 | Parthasarathy |
| 2021/0237072 A1 | 8/2021 | Parthasarathy |
| 2021/0237073 A1 | 8/2021 | Parthasarathy |
| 2021/0237074 A1 | 8/2021 | Parthasarathy |
| 2021/0237075 A1 | 8/2021 | Parthasarathy |
| 2021/0237076 A1 | 8/2021 | Parthasarathy |
| 2021/0252512 A1 | 8/2021 | Parthasarathy |
| 2021/0252513 A1 | 8/2021 | Parthasarathy |
| 2021/0346584 A1 | 11/2021 | Lee et al. |
| 2022/0088041 A1 | 3/2022 | Londesbrough et al. |
| 2022/0409584 A1 | 12/2022 | Bilal et al. |

FOREIGN PATENT DOCUMENTS

| | | | |
|---|---|---|---|
| EP | | 1190229 B1 | 10/2011 |
| EP | | 2902108 A1 | 8/2015 |
| WO | WO 1999/061888 A2 | | 12/1999 |
| WO | WO 1999/061888 A3 | | 12/1999 |
| WO | WO 2009/051734 A1 | | 4/2009 |
| WO | WO 2013/085797 A1 | | 6/2013 |
| WO | WO 2017/034517 A1 | | 3/2017 |
| WO | WO-2017035262 A1 * | | 3/2017 ............ A61K 35/12 |
| WO | WO 2017/189899 A1 | | 11/2017 |
| WO | WO 2018/020285 A2 | | 2/2018 |
| WO | WO 2018/237239 A1 | | 12/2018 |
| WO | WO 2019/035952 A1 | | 2/2019 |
| WO | WO 2019/040599 A1 | | 2/2019 |
| WO | WO 2019/189408 A1 | | 10/2019 |
| WO | WO 2019/195934 A1 | | 10/2019 |

(56) References Cited

FOREIGN PATENT DOCUMENTS

| WO | WO 2019/204333 A1 | 10/2019 | |
|---|---|---|---|
| WO | WO-2019204854 A1 * | 10/2019 | ......... G01N 15/0612 |

OTHER PUBLICATIONS https://bmccancer.biomedcentral.com/track/pdf/10.1186/1471-2407-13-283.pdf; "Detection of Cancer Before Distant Metastasis" Article; Leon WMM Terstappen et al.; BMC Cancer; Published Jun. 13, 2013.

https://www.nature.com/articles/s41408-020-0320-7.pdf; ""Direct to Drug" Screening as a Precision Medicine Tool in Multiple Myeloma" Article; Cecilia Bonolo de Campos et al.; Blood Cancer Journal; Published May 11, 2020.

https://www.mdpi.com/1422-0067/21/13/4813/pdf; "A Pilot Study of the Predictive Potential of Chemosensitivity and Gene Expression Assays Using Circulating Tumour Cells from Patients with Recurrent Ovarian Cancer" Article; Stefano Guadagni et al.; International Journal of Molecular Sciences; Jul. 7, 2020.

https://www.mdpi.com/2072-6694/12/3/743/pdf; "Gauging the Impact of Cancer Treatment Modalities on Circulating Tumor Cells (CTCs)" Article; Michele I. Vitolo et al.; Cancers Journal; Mar. 21, 2020.

https://www.pnas.org/content/pnas/117/29/16839.full.pdf; "Ultrahigh-Throughput Magnetic Sorting of Large Blood Volumes for Epitope-Agnostic Isolation of Circulating Tumor Cells" Article; Daniel A. Haber et al.; PNAS; May 13, 2020.

https://wjso.biomedcentral.com/track/pdf/10.1186/1477-7819-11-159.pdf; "Extracorporeal Tumor Cell Filtration during Extended Liver Surgery: First Clinical use of Leukocyte Depletion Filters—a Case Series" Article; Nils R. Frühauf et al.; World Journal of Surgical Oncology; Jul. 17, 2013.

https://clincancerres.aacrjournals.org/content/clincanres/24/22/5635.full-text.pdf; "Single-Cell Analyses of Prostate Cancer Liquid Biopsies Acquired by Apheresis" Article; Johann S. de Bono et al.; AACR Publications; Aug. 9, 2018.

https://www.nature.com/articles/s41467-019-09439-9.pdf; "A Temporary Indwelling Intravascular Aphaeretic System for In Vivo Enrichment of Circulating Tumor Cells" Article; Sunitha Nagrath et al.; Nature Communications; Apr. 1, 2019.

https://academic.oup.com/noa/article-pdf/2/1/vdaa052/33236713/vdaa052.pdf; "Evaluation of Neurapheresis Therapy In Vitro: a Novel Approach for the Treatment of Leptomeningeal Metastases" Article; Shivanand P. Lad et al.; Neuro-Oncology Advances: Apr. 18, 2020.

https://www.ncbi.nlm.nih.gov/pmc/articles/PMC4486079/pdf/nihms-702225.pdf; "The CTC-Chip: An Exciting New Tool to Detect Circulating Tumor Cells in Lung Cancer Patients" Article; Sunitha Nagrath, PhD et al.; J Thorac Oncol.; PMC—HHS Author Manuscripts; Jun. 30, 2015.

https://aip.scitation.org/doi/pdf/10.1063/1.5120501; "Label-Free Microfluidic Sorting of Microparticles" Article; Ian Papautsky et al.; APL Bioengineering; Dec. 11, 2019.

https://onlinelibrary.wiley.com/doi/epdf/10.1002/cyto.a.23100; "Quantitative Phase Microscopy Spatial Signatures of Cancer Cells" Article; Darina Roitshtain et al.; Submitted to Cytometry Part A; Wiley Online Library; Apr. 20, 2017.

https://www.ncbi.nlm.nih.gov/pmc/articles/PMC6261517/pdf/nihms982306.pdf; "An Intravascular Magnetic Wire for the High-Throughput Retrieval of Circulating Tumour Cells In Vivo" Article; Sanjiv S. Gambhir et al.; Nat Biomed Eng.; MC-HHS Author Manuscripts; Sep. 2018.

Extended European Search Report for European Patent Application No. 21748010.2, mailed Jan. 30, 2024.

GAMBRO BCT, "COBE®Spectra Aphoresis System Essentials Guide", Mar. 2005.

Sharma et al., "Circulating Tumor Cell Isolation, Culture, and Downstream Molecular Analysis", Biotechnol Adv., Jul.-Aug. 2018, 36(4): 1063-1078.

* cited by examiner

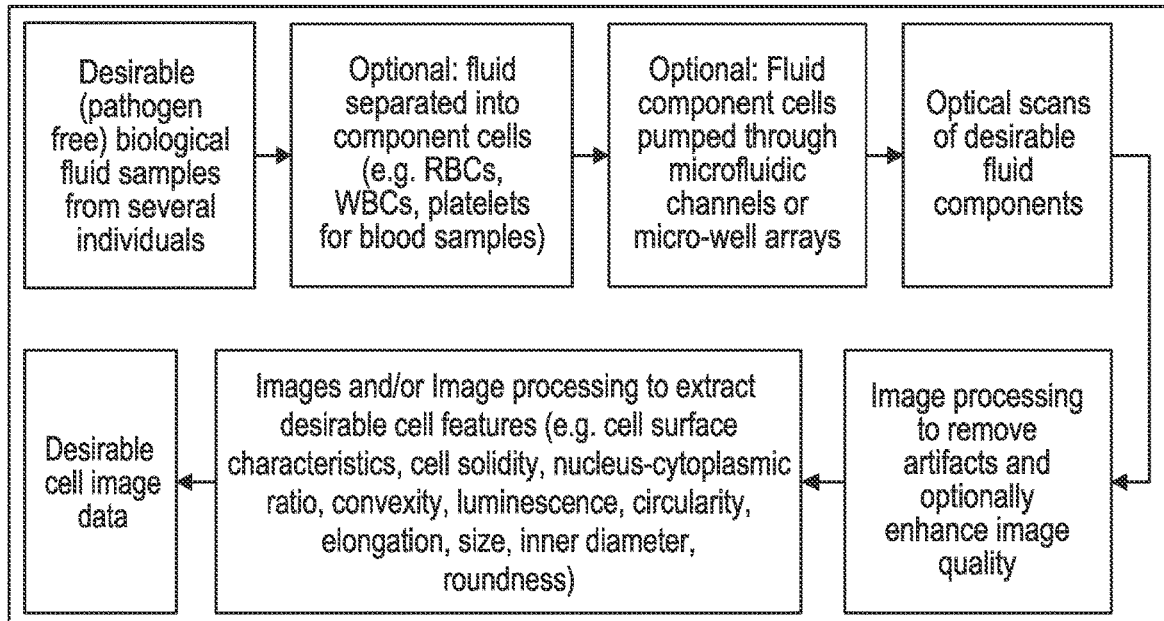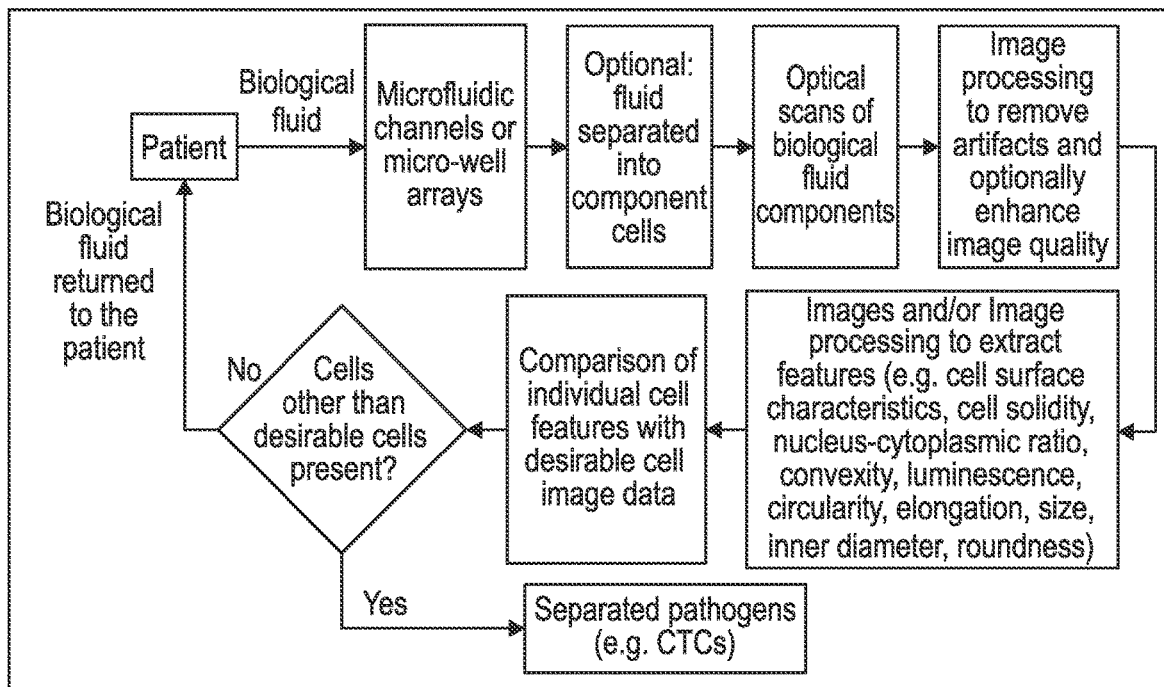
FIG. 27

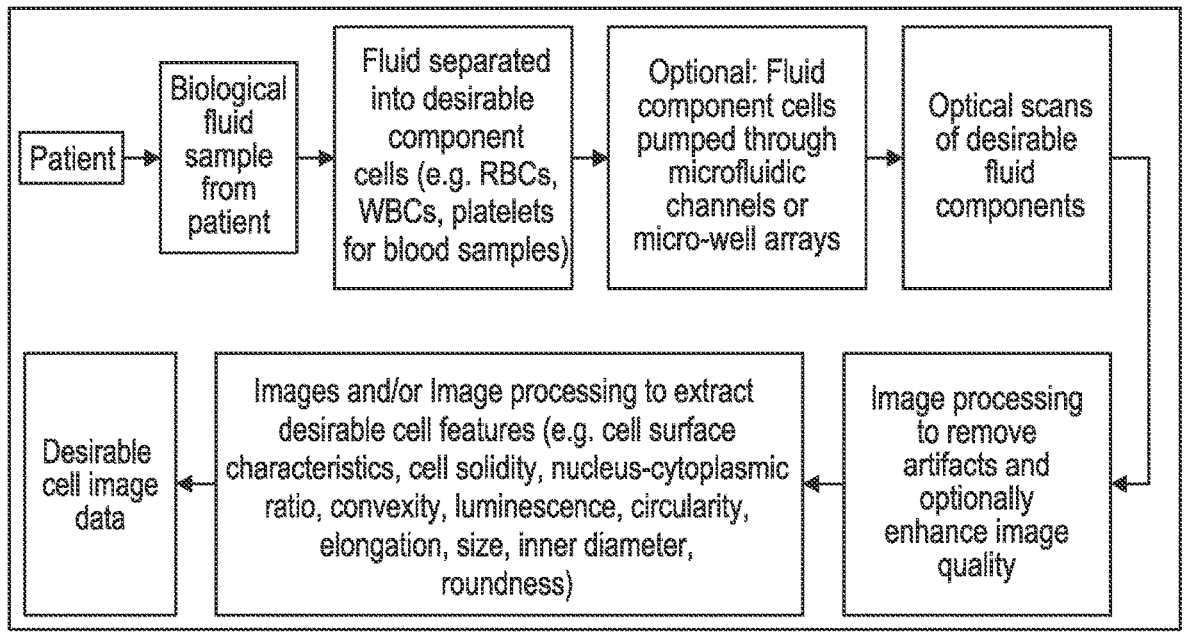
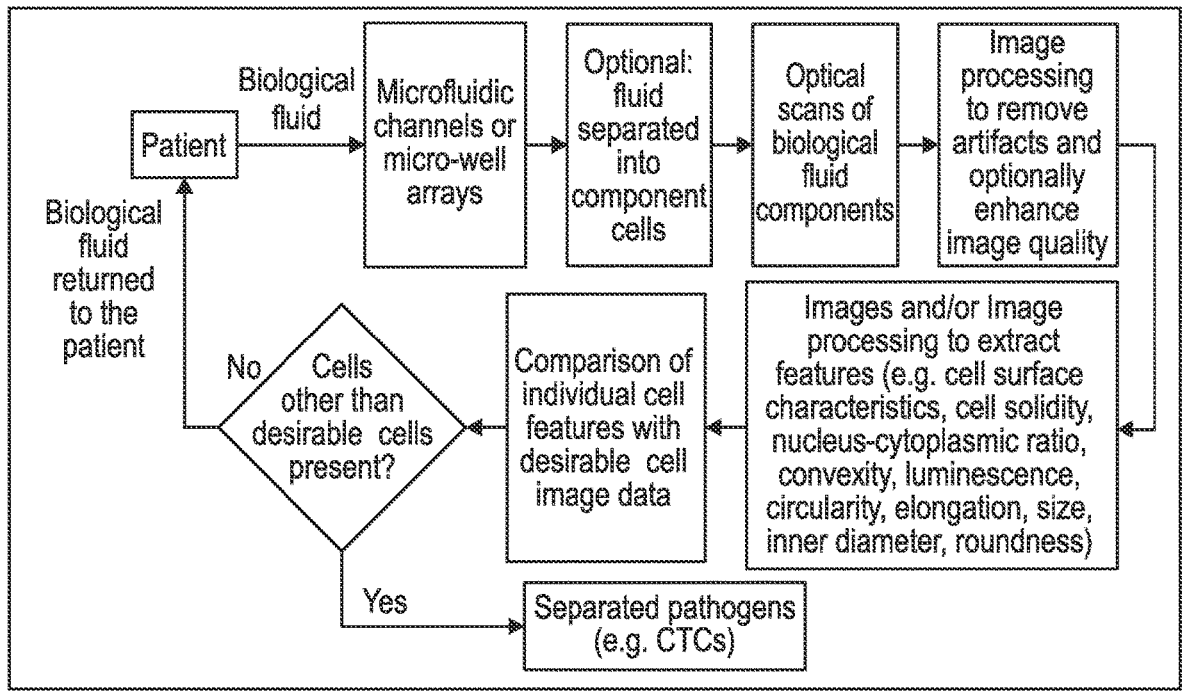
FIG. 28

BIOLOGICAL FLUID FILTRATION SYSTEM

CROSS REFERENCE TO RELATED APPLICATIONS

The present application is a continuation of U.S. application Ser. No. 17/162,450 filed on Jan. 29, 2021, which claims priority to U.S. Provisional Application No. 62/968,476 filed Jan. 31, 2020. Each of the aforementioned patent applications, and any applications related thereto, is herein incorporated by reference in their entirety.

STATEMENT REGARDING FEDERALLY SPONSORED RESEARCH OR DEVELOPMENT

Not applicable to this application.

BACKGROUND

Field

Example embodiments in general relate to a biological fluid filtration system for optically scanning a biological fluid so as to filter potentially harmful constituents from the biological fluid for therapeutic or diagnostic purposes.

Related Art

Any discussion of the related art throughout the specification should in no way be considered as an admission that such related art is widely known or forms part of common general knowledge in the field.

Eight million people die from cancer each year and it is predicted that 13.2 million patients will do so in 2030. 90% of deaths are caused by metastases. Cancer metastasis spreads when Circulating Tumor Cells (CTCs) dislodge from the primary tumor site and travel via the circulatory system (or lymphatic system) and lodge at another site. Certain cancer types disseminate as single cells, while others—such as oral squamous cell carcinoma, colorectal carcinoma, melanoma, breast cancer, endometrial carcinoma, and pancreatic cancer, do so by collective cell (CTC-cluster) migration. Significant variability has also been found from transcriptional profiling and surface marker analysis, leading to an understanding that CTCs are highly heterogeneous. In 2012, it was shown that CTC-variability is highly consistent with tumor tissue variability, meaning that phenotyping of CTCs will bring to light many of the characteristics present in the tumor itself.

It is estimated that every day, tumors release thousands of cells into the circulation where CTCs survive for about 1-2.5 hours. Most CTCs undergo apoptosis upon release or remain dormant, and only a few (0.1%) are able to survive the effect of stressors and ultimately then form distant metastases. Using the only FDA-approved system for CTC separation, CellSearch (Menarini Silicon Biosystems), researchers detected a single CTC (median 1, range from 0 to 4) in 7.5 ml of blood in 13% of analyzed samples, while analyzing 30-mL blood volume samples allowed a detection rate of 2 CTCs (range from 0 to 9) in 47% of the analyzed samples. Thus, rarity is a significant challenge for the identification and separation of CTCs and CTC-clusters. 10 ml of a peripheral blood sample from a metastatic cancer patient typically contains 0-100 single CTCs and roughly 0-5 CTC-clusters (5-20% of all CTCs) among approximately $50 \times 10^9$ red blood cells, $80 \times 10^6$ white blood cells and $3 \times 10^9$ platelets. Furthermore, some CTCs overlap in size with white blood cells, making size based separation challenging.

Yet, due to the clinical significance of CTCs in cancer prognosis and treatment, research in techniques to separate CTCs is very active. Separation strategies are categorized as positive enrichment, negative enrichment, and label-free techniques. Positive enrichment typically refers to a process that selects for the CTCs while leaving the other particles behind. This typically has a very high accuracy, and one of the most common methods involves antibody tagging surface antigens (e.g. EpCAM) on the CTC.

Negative enrichment involves targeting and removing other types of cells, in this case, white and red blood cells. This generally leads to lower purity but does not have the challenge of removal of binding probes from the surface of the CTC, and is often able to bypass the challenge of CTC heterogeneity. A label-free technique is one that avoids biochemically tagging the desired molecule. This means that rather than using immune affinity for capture or sample cleaning, another method that does not involve labeling cells is used such as size-based, mechanical property based, acoustic, or optical. Some researchers have proposed combining several techniques, such as optical detection of fluorescently tagged CTCs followed by size based microfluidic separation, to achieve better results. Recently, building upon advances in AI and machine learning, methods have been published to automatically detect CTCs by training machine learning algorithms on microscopic images of CTCs in sample blood.

SUMMARY

An example embodiment is directed to a biological fluid filtration system. The biological fluid filtration system generally includes a fluid receiving device adapted to receive a biological fluid. A valve including an inlet, a first outlet, and a second outlet is fluidly connected to the fluid receiving device. The biological fluid within the fluid receiving device is scanned by a scanner to produce scanned data relating to the biological fluid. A control unit in communication with the scanner and the valve receives the scanned data and controls the valve based on the scanned data. The valve is controlled to direct the biological fluid through either the first or second outlet of the valve depending upon the constituents of the biological fluid identified by the control unit.

There has thus been outlined, rather broadly, some of the embodiments of the biological fluid filtration system in order that the detailed description thereof may be better understood, and in order that the present contribution to the art may be better appreciated. There are additional embodiments of the biological fluid filtration system that will be described hereinafter and that will form the subject matter of the claims appended hereto. In this respect, before explaining at least one embodiment of the biological fluid filtration system in detail, it is to be understood that the biological fluid filtration system is not limited in its application to the details of construction or to the arrangements of the components set forth in the following description or illustrated in the drawings. The biological fluid filtration system is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

FIG. 27 is a block diagram of an aphaeretic system and method of computer processing of reference image data obtained from optic scans of biological fluid components from fluid samples of representative individuals other than patient.

FIG. 28 is a block diagram of an aphaeretic system and method of computer processing of reference image data obtained from optic scans of biological fluid components from fluid sample of patient.

DETAILED DESCRIPTION

Figure 1:
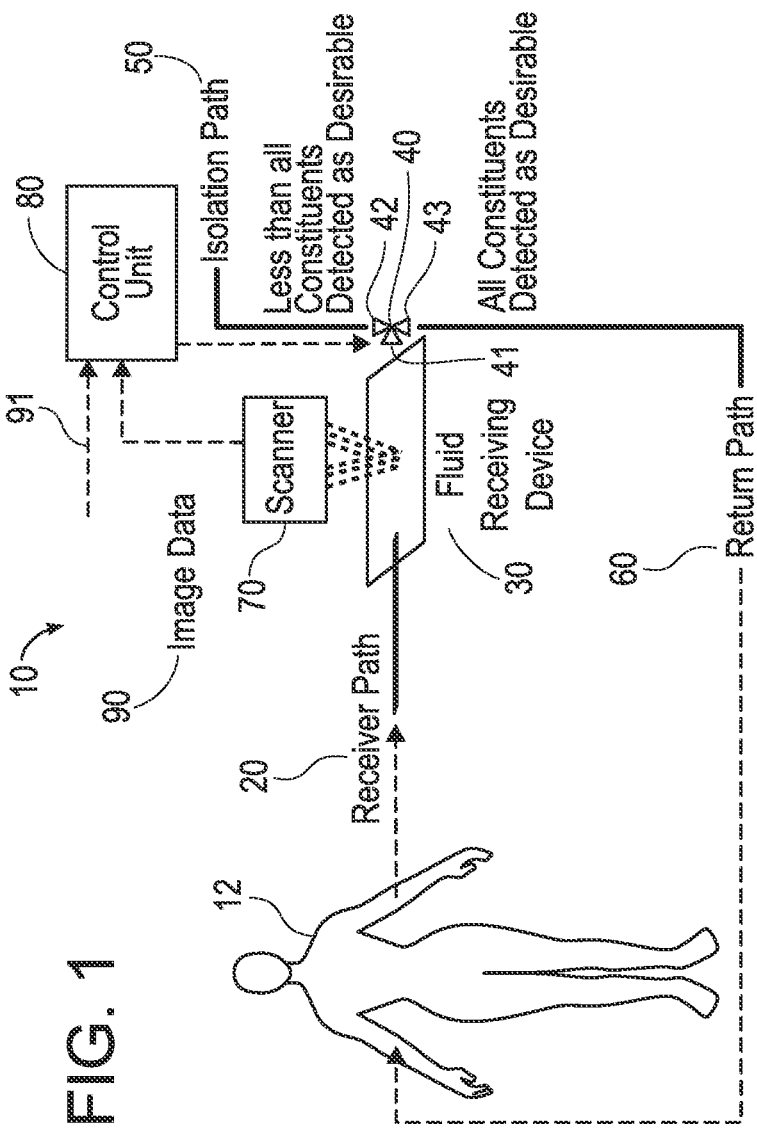
FIG. 1 is a perspective view of a biological fluid filtration system in accordance with an example embodiment.

A. Overview.

An example biological fluid filtration system 10 generally comprises a receiver path 20 adapted to receive a biological fluid 16 from a biological fluid source 17. The receiver path 20 may comprise various types of conduits, channels, or the like known in the art for transferring a fluid between two locations such as, for example, an apheresis catheter, an indwelling line, or a venous catheter. Other examples could include two intravenous (IV) lines: one for access to an artery and the other for access to a vein. The systems and methods described herein may be utilized for filtering a wide range of biological fluids 16, such as but not limited to blood, lymphatic fluid, cerebrospinal fluid, sweat, urine, pericardial fluid, stools, saliva, and the like. The biological fluid source 17 may comprise the patient 12 herself or, in some embodiments, a separate reservoir in which the biological fluid 16 is temporarily stored after being drawn from the patient 12.

As shown throughout the figures, a fluid receiving device 30 may be fluidly connected to the receiver path 20 so as to receive the biological fluid 16 from the receiver path 20. The fluid receiving device 30 generally comprises a structure in which the biological fluid 16 is temporarily stored or channeled to be optically scanned by a scanner 70. As discussed in more detail below, the fluid receiving device 30 may vary in different embodiments. In a first exemplary embodiment, the fluid receiving device 30 may comprise one or more microfluidic channels 31. In a second exemplary embodiment, the fluid receiving device 30 may comprise a microwell array 32 comprised of a plurality of microwells. In yet another exemplary embodiment, the fluid receiving device 30 may comprise a microfluidic droplet generator 34 to scan cell encapsulating droplets 39.

A valve 40 may be positioned downstream of the fluid receiving device 30, with the valve 40 being configured to direct flow of the biological fluid 16 after being scanned within the fluid receiving device 30. The valve 40 may comprise an inlet 41 which is fluidly connected to the fluid receiving device 30. The valve 40 may comprise a first outlet 42 which is fluidly connected to an isolation path 50 and, in some embodiments, a second outlet 43 which is fluidly connected to a return path 60. In some embodiments, the return path 60 may be omitted, with the biological fluid 16 being returned to the biological fluid source 17 through the receiver path 20 rather than a separate return path 60. In some embodiments, instead of or in addition to a return path 60 back to the biological fluid source 17, a reprocessing path 62 may be utilized to return back to the fluid receiving device 30 for further processing.

It should be appreciated that the valve 40 may have a default state in which flow is directed towards one of the two outlets 42, 43 in the absence of control of the valve 40. For example, the valve 40 may be a spring-based valve 40 that, by default, directs flow to the first outlet 42. Such a valve 40 may be adjusted to direct flow to the second outlet 43, such as by activation of a spring. Upon release of the spring, such a valve 40 may revert back to its original, default state in which the valve 40 directs flow to the first outlet 42. Thus, the valve 40 may not need to be controlled if the default state of the valve 40 already directs flow to the desired outlet 42, 43.

The isolation path 50 is fluidly connected to the first outlet 42 of the valve 40 such that the biological fluid 16 contents of the fluid receiving device 30 may be isolated or sequestered from the biological fluid source 17 if undesirable constituents 14 are identified in the biological fluid 16 during scanning by the scanner 70 as discussed in more detail below. The isolation path 50 may comprise one or more channels which are fluidly connected to the first outlet 42 of the valve 40 such that any scanned biological fluid 16 containing undesirable constituents 14 may be sequestered or isolated. The isolation path 50 may be fluidly connected to a reservoir, cartridge, container, vessel, or any device capable of holding a fluid. Such sequestered or isolated biological fluids 16 may be utilized for diagnostics or may be disposed of.

The scanner 70 is generally oriented toward the fluid receiving device 30. Although the singular term is used throughout, it should be appreciated that, in some embodiments, multiple scanners 70 may be utilized. For example, in an embodiment in which the fluid receiving device 30 is comprised of a microwell array 32, a first scanner 70 could be oriented toward a first portion of the microwell array 32 and a second scanner 70 could be oriented toward a second portion of the microwell array 32. In any case, the scanner 70 is adapted to optically scan the biological fluid 16 within the fluid receiving device 30 so as to derive a scanned data 90 of the biological fluid 16.

In an exemplary embodiment, the scanner 70 may utilize digital holographic microscopy (DHM) to scan the contents of the fluid receiving device 30. In such an embodiment, the scanner 70 may comprise a light source 72 which is adapted to illuminate the biological fluid 16 to be scanned. More specifically, the scanner 70 may comprise a light source 72 such as a laser or a light-emitting diode. In addition to the light source 72, the scanner 70 in such an embodiment will generally include a microscope objective 73 adapted to gather light from the biological fluid 16 and an image sensor 76 so as to produce a holographic image. Thus, the microscope objective 73 will generally comprise a lens which functions to collect an object wave 77 front created by the light source 72 as discussed below.

The control unit 80 in such an embodiment may then function as a digital lens to calculate a viewable image of the object wave 77 front. Since the microscope objective 73 in such a digital holographic microscopy embodiment is only used to collect light, rather than to form an image, the microscope objective 73 may be omitted entirely in some embodiments. Other example embodiments could rely on other arrangements to generate holograms of the object being scanned.

A control unit 80 may be communicatively connected to the scanner 70 so as to receive the scanned data 90 of the biological fluid 16 from the scanner 70. The control unit 80 may be operatively connected to the valve 40 such that the control unit 80 may direct the opening or closing of the inlet 41 and outlets 42, 43 of the valve 40.

The control unit 80 is adapted to compare the scanned data 90 of the biological fluid 16 with a reference data 91. As discussed below, the reference data 91 may comprise patterns, criteria, images, and/or other characteristics of desirable constituents 15 such as red blood cells, white blood cells, and the like. The desirable constituents 15 may comprise biological fluid constituents 13 that are desirable for a particular patient 12 or for a particular application. It should be appreciated that a biological fluid constituent 13 which is desirable for a first patient 12 may be undesirable for a second patient 12. Further, a biological fluid constituent 13 which is desirable for a particular application may be undesirable for other applications.

Thus, the control unit 80 may be configured to determine if a particular sample of biological fluid 16 consists only of such desirable constituents, with the sample of biological fluid 16 being directed through the first outlet 42 of the valve 40 if only desirable constituents are identified. If the sample of biological fluid 16 does not consist exclusively of such desirable constituents, the sample of the biological fluid 16 may be directed instead through the second outlet 43 of the valve 40.

The control unit 80 is adapted to direct flow of the biological fluid 16 from the fluid receiving device 30 by operation of the valve 40. If the scanned data 90 of the biological fluid 16 contains only desirable constituents 15 exhibiting criteria that match with any of the healthy or desirable constituents of the reference data 91, the control unit 80 will switch the valve 40 so as to direct the biological fluid 16 to the biological fluid source 17 by a return path 60, such as by the receiver path 20 in reverse. If the scanned data 90 of the biological fluid 16 includes one or more undesirable constituents 14 not exhibiting criteria that match with any known desirable constituents 15 of the reference data 91, the control unit 80 will switch the valve 40 so as to direct the biological fluid 16 to the isolation path 50 to be isolated or sequestered from the biological fluid source 17 for further diagnostic or therapeutic processing. Alternatively, if the scanned data 90 includes one or more undesirable constituents 14, the valve 40 may be switched so as to direct the biological fluid 16 back to the fluid receiving device 30 by a reprocessing path 62 for further processing. The scanned and reference data 90, 91 could include images and/or morphological data of the cells in the images.

In an exemplary embodiment, the biological fluid filtration system 10 may comprise a fluid receiving device 30 adapted to receive a biological fluid 16 from a biological fluid source 17. A valve 40 may be fluidly connected to the fluid receiving device 30, with the valve 40 including an inlet 41, a first outlet 42, and a second outlet 43. The inlet 41 of the valve 40 is fluidly connected to the fluid receiving device 30. A scanner 70 is configured to scan the biological fluid 16 within the fluid receiving device 30 to produce a scanned data 90 relating to the biological fluid 16 within the fluid receiving device 30. A control unit 80 is in communication with the scanner 70 and the valve 40, with the control unit 80 being configured to receive the scanned data 90 from the scanner 70 and to control the valve 40 based on the scanned data 90 from the scanner 70. The control unit 80 is configured to control the valve 40 to (a) direct the biological fluid 16 through the first outlet 42 if the control unit 80 determines that the scanned data 90 indicates a presence of an undesirable constituent 14 within the biological fluid 16 or (b) direct the biological fluid 16 through the second outlet 43 if the control unit 80 determines that the scanned data 90 does not indicate a presence of an undesirable constituent 14 within the biological fluid 16.

The fluid receiving device 30 may comprise a microfluidic channel 31. An inlet valve 33 may be fluidly connected to an inlet of the microfluidic channel 31 for pausing flow of the biological fluid 16 into the microfluidic channel 31. The undesirable constituent 14 may be comprised of an unknown constituent of the biological fluid 16 that is not recognized by the control unit 80. The undesired constituent 14 may be comprised of a tumor cell. The control unit 80 may be configured to compare the scanned data 90 to a reference data 91. The reference data 91 may be comprised of a characteristic or an image of a healthy cell. The scanned data 90 may be comprised of an image.

The fluid receiving device 30 may comprise a plurality of microfluidic channels 31. Each of the microfluidic channels 31 may be arranged in parallel. The scanner 70 may be configured to scan each of the plurality of microfluidic channels 31. The biological fluid 16 may be comprised of blood, cerebrospinal fluid, or lymphatic fluid. The first outlet 42 of the valve 40 may be fluidly connected to a reservoir. The second outlet 43 of the valve 40 may be fluidly connected to a biological fluid source 17. The scanner 70 may be comprised of an optical scanner such as a digital holographic microscope. The scanner 70 may include a monochromatic laser.

In an exemplary embodiment of the biological fluid filtration system 10, the control unit 80 is configured to control the valve 40 to (a) direct the biological fluid 16 through the first outlet 42 if the control unit determines that the scanned data 90 indicates that the biological fluid 16 consists of only desirable constituents 15 or (b) direct the biological fluid 16 through the second outlet 43 if the control unit 80 determines that the scanned data 90 does not indicate that the biological fluid 16 consists of only desirable constituents 15. A microfluidic separation module 100 may be fluidly connected to an inlet of the fluid receiving device 30 for removing one or more biological fluid constituents 13 from the biological fluid 16 prior to scanning.

In an exemplary embodiment, the control unit 80 is configured to determine that the scanned data 90 indicates the presence of the undesirable constituent 14 when the control unit 80 detects the undesirable constituent 14 within the scanned data 90. In another exemplary embodiment, the control unit 80 is configured to determine that the scanned data 90 indicates the presence of the undesirable constituent 14 when the control unit 80 detects an unknown constituent within the scanned data 90. In another exemplary embodiment, the control unit 80 is configured to determine that the scanned data 90 indicates the presence of the undesirable constituent 14 when the control unit 80 detects only desirable constituents 15 within the scanned data 90.

An exemplary method of filtering a biological fluid 16 using the biological fluid filtration system 10 may comprise the steps of receiving the biological fluid 16 by the fluid receiving device 30; scanning the biological fluid 16 within the fluid receiving device 30 by the scanner 70; directing the biological fluid 16 through the first outlet 42 if the control unit 80 determines that the scanned data 90 indicates a presence of an undesirable constituent 14 within the biological fluid 16; and directing the biological fluid 16 through the second outlet 43 if the control unit 80 determines that the scanned data 90 indicates a presence of an undesirable constituent 14 within the biological fluid 16.

B. Biological Fluid Filtration System.

Figure 30:
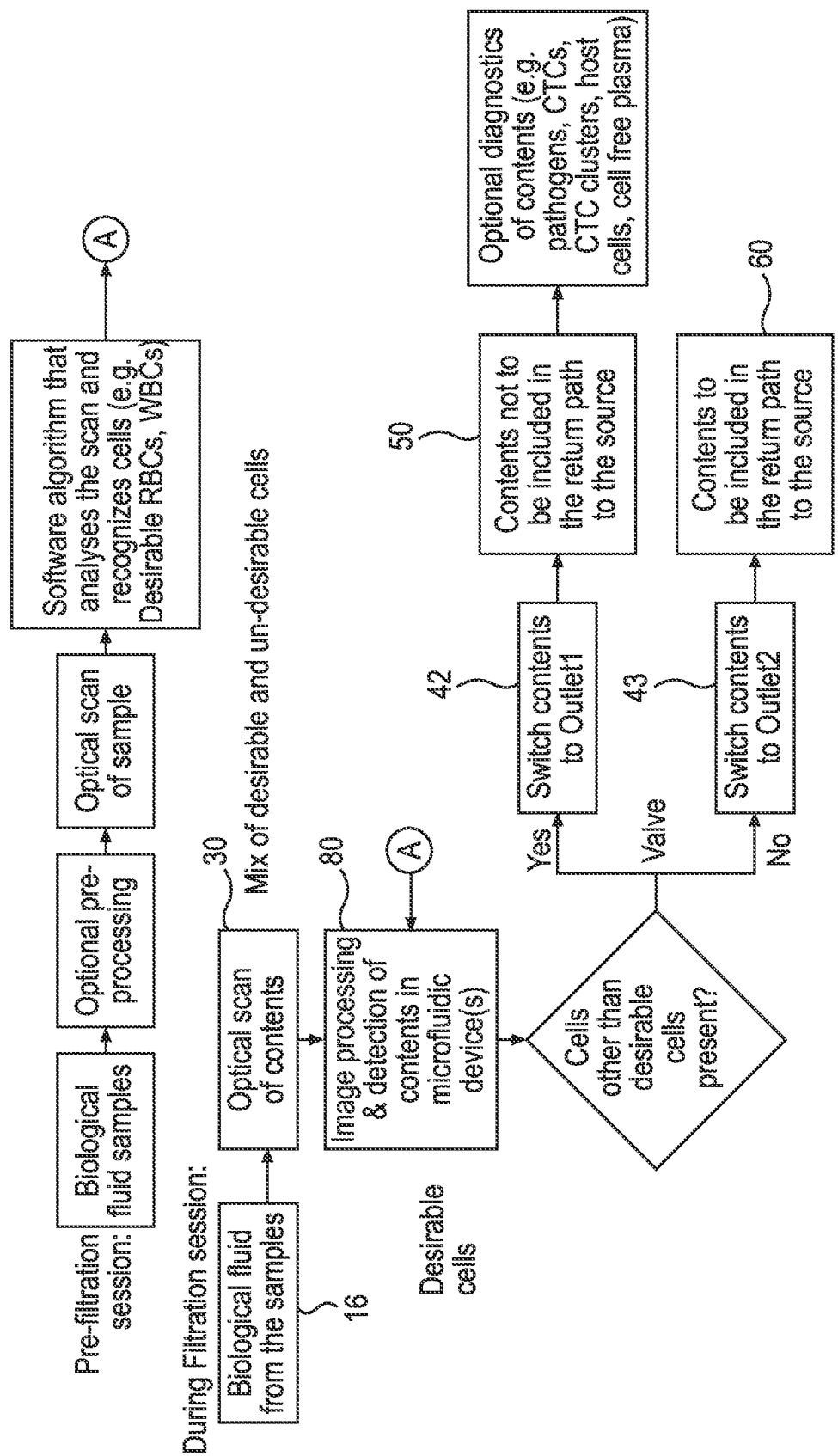
FIG. 30 is a flowchart illustrating a system and method of filtering a biological fluid utilizing both a pre-filtration session and a filtration session in accordance with an example embodiment.

As shown in FIG. 30, an exemplary embodiment of a biological fluid filtration system 10 may comprise an automated optofluidic system for removal of undesirable constituents 14 from a biological fluid 16 by optically inspecting the biological fluid constituents 13 and sequestering any undesirable constituents 14 that do not meet recognized criterial of known desirable constituents 15 of the biological fluid 16 such as biological fluid constituents 13 that are desirable for a particular patient 12 or application. It should be appreciated that the biological fluid constituents 13 may comprise biological constituents or may comprise non-biological constituents such as dyes and the like.

The systems and methods described herein may be utilized for the filtration of a wide range of biological fluids 16, such as but not limited to blood, lymphatic fluid, cerebrospinal fluid, sweat, urine, pericardial fluid, stools, saliva, and any other organism-derived extracellular fluid that retains or transports nutrients, cells, waste products, or foreign bodies, or that is susceptible to pathogenic infection. It should be appreciated that the systems and methods described herein are further not intended to be limited to humans, and could be utilized in connection with veterinary treatment of a wide range of animals in some embodiments.

The systems and methods described herein may be utilized for both diagnostic and therapeutic applications. In some embodiments, multiple biological fluids 16 may be processed from the same individual (animal or human). As a non-limiting example, there are cases in which cancer has spread from the original tumor site (e.g., breast, lung, etc.) to the meninges surrounding the brain and/or spinal cord. In such cases, the systems and methods described herein may be utilized to process and filter CTCs and CTC-clusters from multiple biological fluids 16, such as from blood as well as from cerebrospinal fluid. In some embodiments, these multiple biological fluids 16 may be aphaeretically processed simultaneously, particularly in a diagnostic setting.

After sequestration of the output, the sequestered output may be reprocessed additional times using an optical filtration system (without the aphaeretic components) to further isolate CTCs, CTC-clusters, WBC's, and cell-free plasma. By utilizing multiple valves and output ports, the isolated CTCs, CTC-clusters, WBC's, and cell-free plasma could be held separately for further processing.

In some embodiments, rather than the biological fluid 16 being directly sourced from a person or animal, the biological fluid 16 could be a sample with or without a return path 60 back to its source. Such embodiments could include the use in diagnostic systems to separate pathogens, CTCs, or CTC-clusters from biological samples for downstream diagnostics (e.g., genomic, transcriptomic, metabolomics, drug sensitivity, drug resistance, etc.) and characterization.

Figure 32:
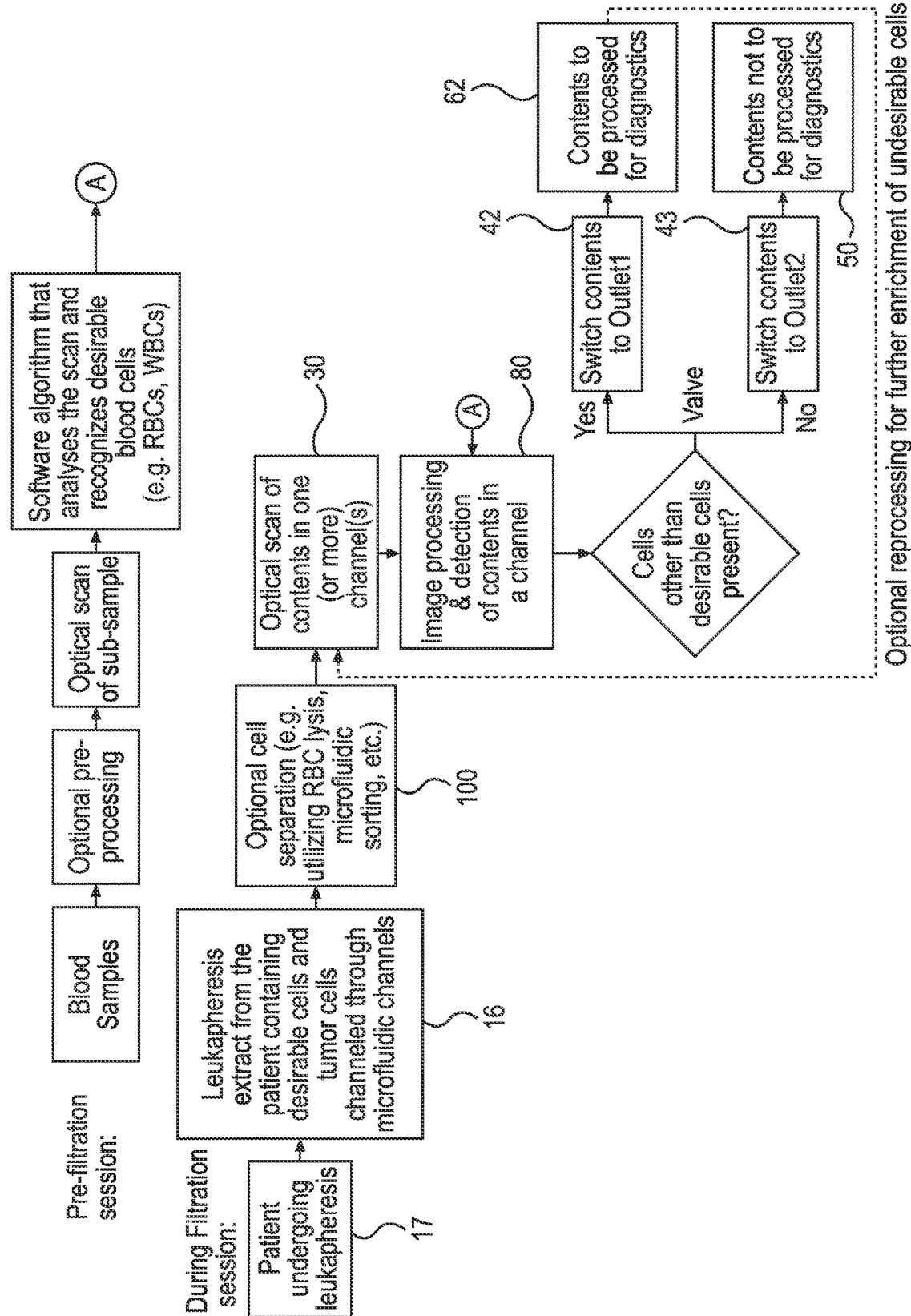
FIG. 32 is a flowchart illustrating a system and method of filtering a biological fluid for use in connection with leukapheresis in accordance with an example embodiment.

In another exemplary embodiment, the biological fluid source 17 could be an aphaeretic extract from a therapeutic aphaeresis or leukapheresis machine. Such leukapheresis machines are routinely utilized in labs, such as where WBC's are separated from a patient. In the case of cancer patients, such leukapheresis extracts may contain CTCs or CTC-clusters and some platelets in addition to WBC's. FIG. 32 illustrates an exemplary method of optical filtration being utilized to process leukapheresis extracts and filter CTCs and CTC-clusters.

Figure 33:
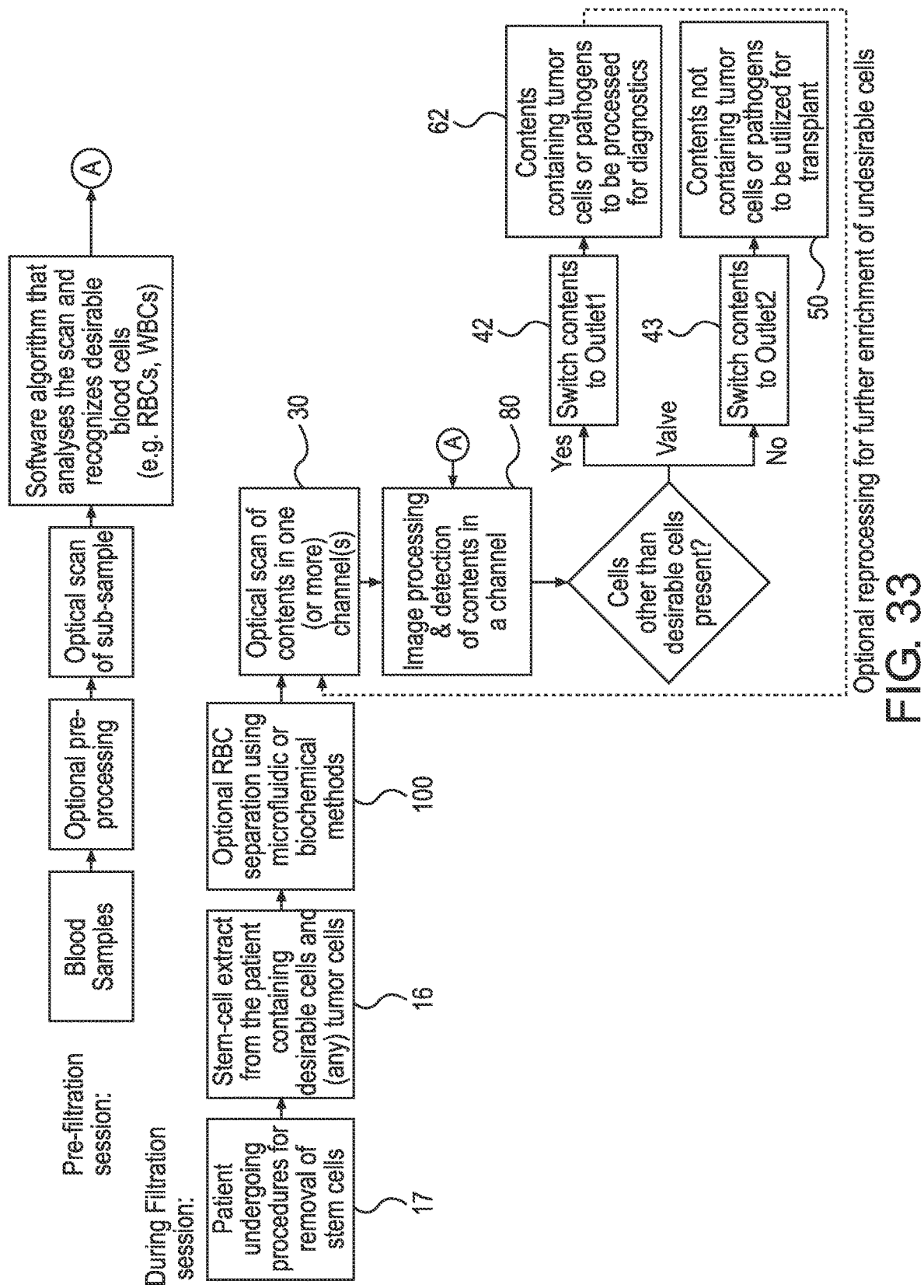
FIG. 33 is a flowchart illustrating a system and method of filtering a biological fluid for use in connection with the removal of stem cells in accordance with an example embodiment.

In yet another exemplary embodiment, tumor cell contaminants may be identified and removed from autologous stem-cell transplant products. Autologous stem cell transplants are typically used in patients who need to undergo high doses of chemotherapy and radiation to cure their diseases. These treatments could be toxic and damage the bone marrow. An autologous stem cell transplant aids to replace the damaged bone marrow, but it is often reported that the process to collect stem cells from the patient could lead to contamination of such products with tumor cells. FIG. 33 illustrates an exemplary method of optical filtration being utilized to process stem cell extracts.

Biological fluid constituents 13 of the biological fluid 16 may comprise desirable constituents 15 and undesirable constituents 14. The desirable constituents 15 may comprise entities within the biological fluid 16 that are recognized as being normally found in the subject biological fluid 16 or that are desirable for a particular patient 12 or application. Such desirable constituents 15 will typically play a role in the proper functioning of tissues, organs, and body systems. In some embodiments, desirable constituents 15 may comprise biological fluid constituents 13 which are known to be benign or otherwise non-harmful.

The undesirable constituents 14 may comprise any biological fluid constituents 13 which are not recognized as being benign, healthy, or otherwise non-harmful. Undesirable constituents 14 may comprise any entity that is not a healthy constituent for a particular patient 12. It should be appreciated that biological fluid constituents 13 may be healthy or desirable for a first patient 12 and unhealthy or undesirable for a second patient 12. Thus, the identification of a particular biological fluid constituent 13 as either healthy/desirable or unhealthy/undesirable will typically be on a patient-by-patient basis. By way of example and without limitation, undesirable constituents 14 may comprise circulating tumor cells (CTCs), CTC-clusters, and pathogens, including bacterial and fungal organisms, protozoa, extracellular vesicles, lipids, cholesterol, dyes, drugs, and infectious viral agents. In some embodiments, any biological fluid constituent 13 which is unrecognized or unknown may be assumed to be an undesirable constituent 14.

FIG. 1 is a schematic diagram illustrating a configuration of one embodiment of biological fluid filtration system 10. The illustrated exemplary embodiment includes a receiver path 20 adapted to receive a biological fluid 16 from a biological fluid source 17; a fluid receiving device 30 fluidly connected to the receiver path 20 so as to receive the biological fluid 16 from receiver path 20; a valve 40 comprising an inlet 41, a first outlet 42, and a second outlet 43, wherein the inlet 41 is fluidly connected to the fluid receiving device 30; an isolation path 50 fluidly connected to first outlet 42; a return path 60 in fluid communication with second outlet 43; a scanner 70 oriented toward the fluid receiving device 30, and a control unit 80 communicatively connected to the scanner 70 and operatively connected to the valve 40.

The scanner 70 is adapted to optically scan the biological fluid 16 within the fluid receiving device 30 so as to derive a scanned data 90 of the biological fluid 16 and relay the scanned data 90 to the control unit 80. The control unit 80 is adapted to compare the scanned data 90 of the biological fluid 16 with a reference data 91, the reference data 91 comprising recognized data patterns characteristic of desirable constituents 15 of the biological fluid 16. In some embodiments, both the scanned and reference data 90, 91 may comprise images which are compared to each other. In other embodiments, the scanned and reference data 90, 91 may comprise characteristics such as cellular characteristics including but not limited to cell solidity, cell surface characteristics, nucleus-cytoplasmic ratio, convexity, luminescence, circularity, elongation, size, inner diameter and roundness. In other embodiments, the scanned and reference data 90, 91 may comprise both images as well as characteristics of the cells in those images, such as cellular characteristics including but not limited to cell solidity, cell surface characteristics, nucleus-cytoplasmic ratio, convexity, luminescence, circularity, elongation, size, inner diameter and roundness.

The control unit 80 is adapted to switch the valve 40 so as to direct the biological fluid 16 to the biological fluid source 17 by the return path 60 if the scanned data 90 of the biological fluid 16 includes only desirable constituents 15 having one or more recognized characteristics of any of the desirable constituents 15 of the reference data 91. The control unit 80 is further adapted to switch the valve 40 so as to direct the biological fluid 16 to the isolation path 50 if the scanned data 90 of the biological fluid 16 includes one or more undesirable constituents 14 lacking one or more recognized characteristics of any of the desirable constituents 15 of the reference data 91. In some embodiments, a reprocessing path 62 may be included to route the biological fluid 16 back to the fluid receiving device 30 for further processing. The return path 60 and reprocessing path 62 may comprise any device or conduit suitable for transferring a fluid.

The return path 60 may comprise a channel or a plurality of channels through which the biological fluid 16 may be returned to the biological fluid source 17. For example, the return path 60 may comprise a catheter, one or more intravenous lines, an indwelling line, or a venous catheter. Similarly, the reprocessing path 60 may comprise a channel or a plurality of channels through which the biological fluid 16 may be returned to the fluid receiving device 30 for further processing.

The receiver path 20 includes any suitable vessel for sterile delivery or transfer of a biological fluid 16 for various purposes such as clinical analysis or processing. For example, in the aphaeretic system of the preferred embodiment, the receiver path 20 may be an apheresis catheter, two intravenous lines (one for the artery and the other for a vein), an indwelling line, or a venous catheter.

The fluid receiving device 30 includes any microfluidic device or system suitable for optic imaging or microscopy. The fluid receiving device 30 will generally include an inlet through which biological fluid 16 is received into the fluid receiving device 30 and an outlet through which biological fluid 16 may exit the fluid receiving device 30. In some embodiments, the fluid receiving device 30 may include multiple inlets and/or multiple outlets. The inlet of the fluid receiving device 30 may be fluidly connected to the biological fluid source 17, and the outlet of the fluid receiving device 30 may be fluidly connected to an isolation path 50, return path 60, reprocessing path 62, or cartridge 126, 146.

Figure 5:
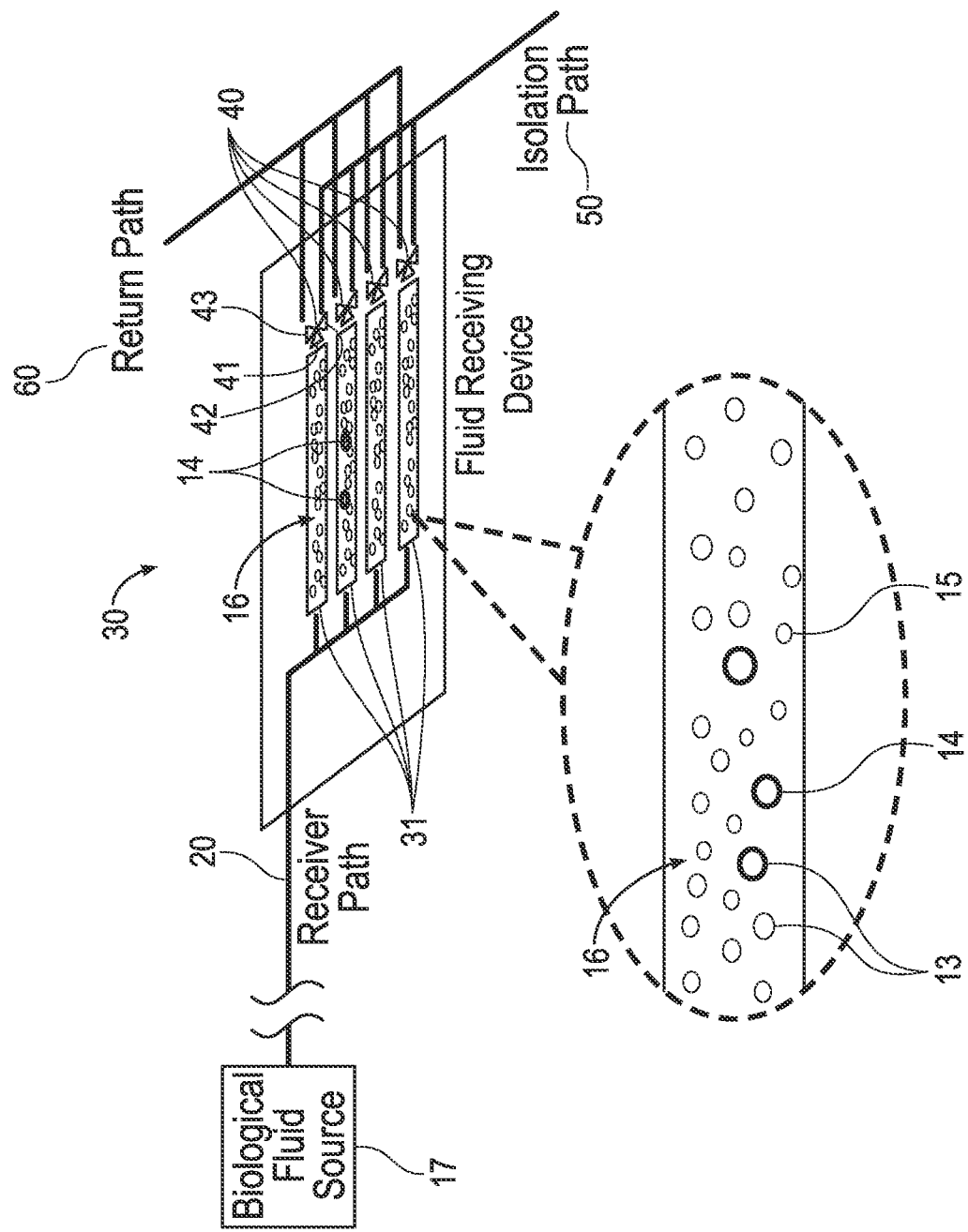
FIG. 5 is a perspective drawing of a fluid receiving device with microfluidic channels in accordance with an example embodiment.
Figure 6:
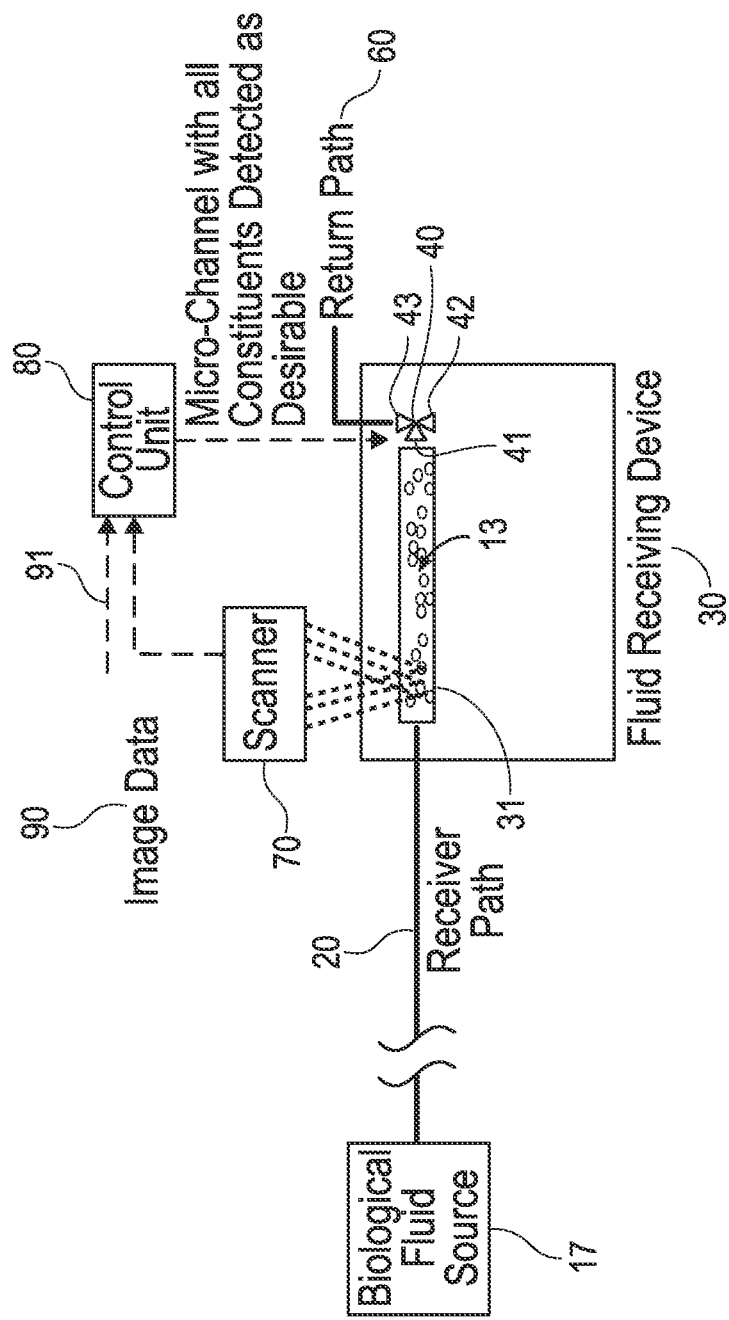
FIG. 6 is a schematic drawing of a fluid receiving device with microfluidic channels in accordance with an example embodiment.
Figure 7:
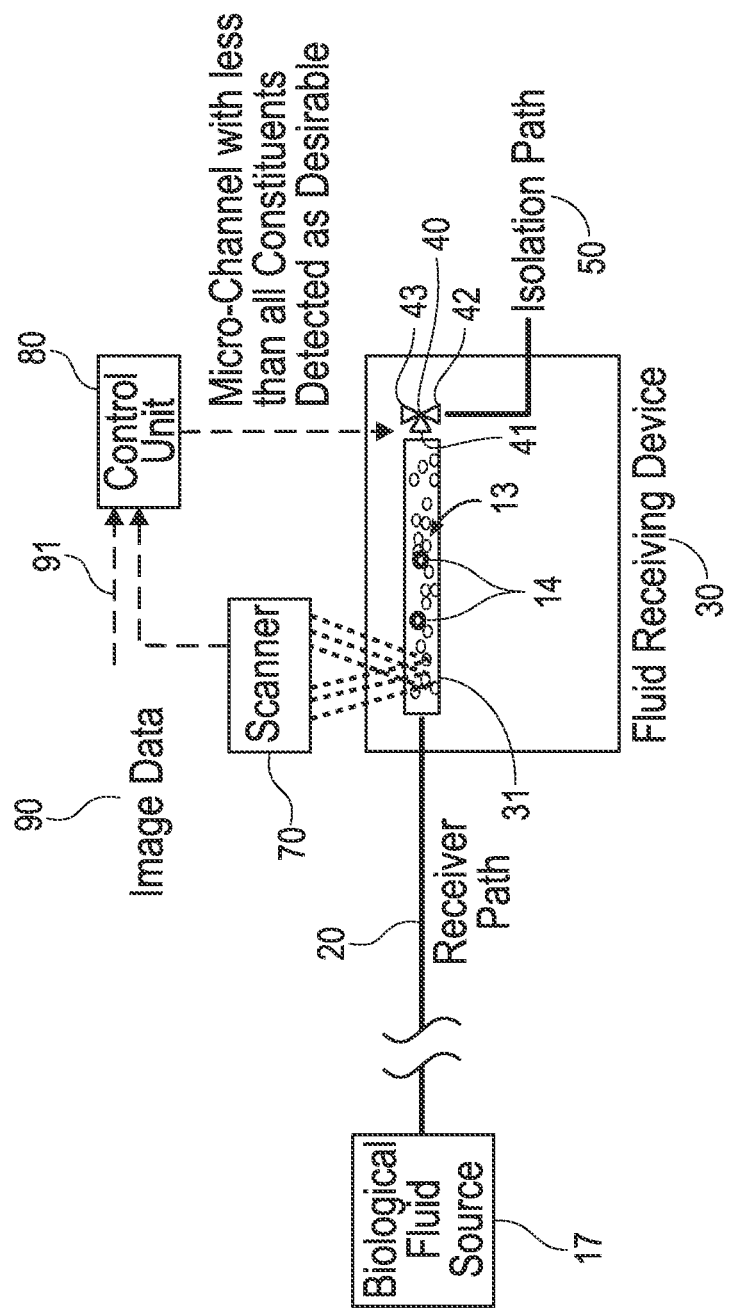
FIG. 7 is a schematic drawing of a fluid receiving device with microfluidic channels in accordance with an example embodiment.

In one embodiment, which is shown schematically in FIGS. 5-7, the fluid receiving device 30 comprises one or more microfluidic channels 31. In the illustrated embodiment, the microfluidic channels 31 are configured for illustration purposes as a batch of planar, parallel channels with a linear geometry. However, microfluidic channels suitable for use with systems and methods described herein may have any number of topographies, geometries and patterns. For example, the microfluidic channels 31 may be etched or molded in a microfluidic chip.

Figure 8:
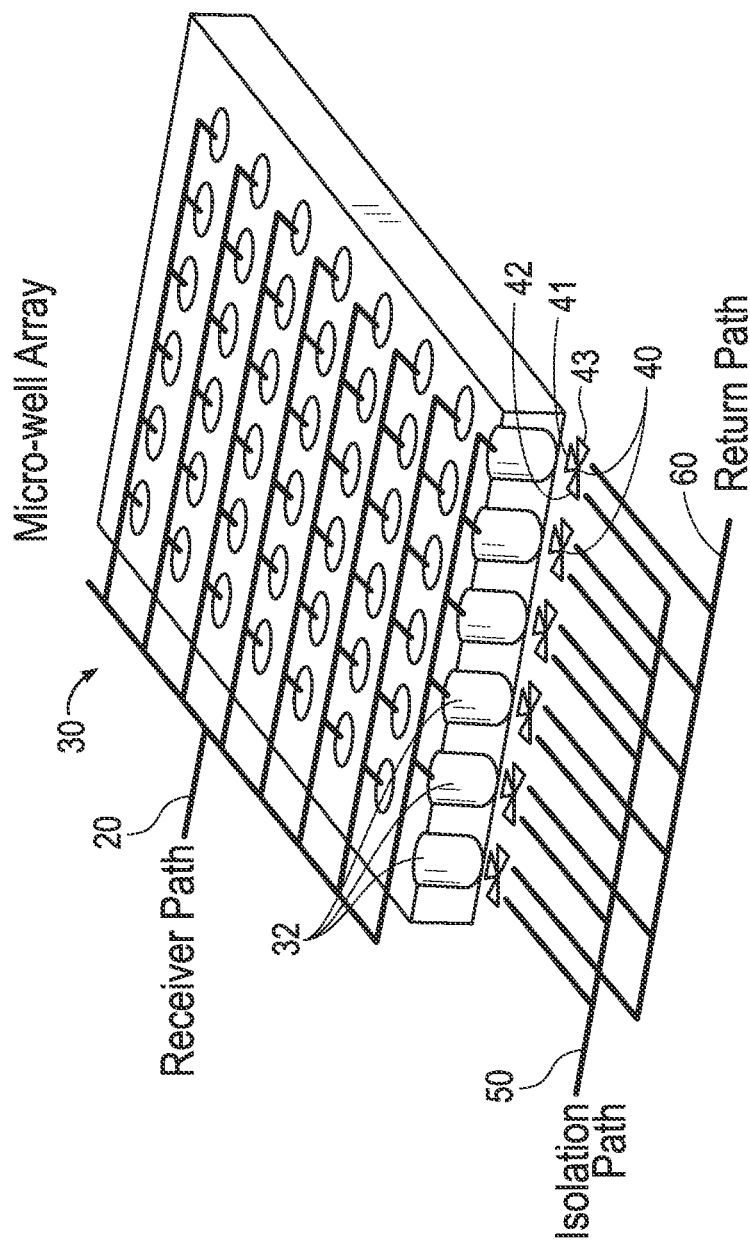
FIG. 8 is a perspective drawing of a fluid receiving device with a microwell array in accordance with an example embodiment.
Figure 9:
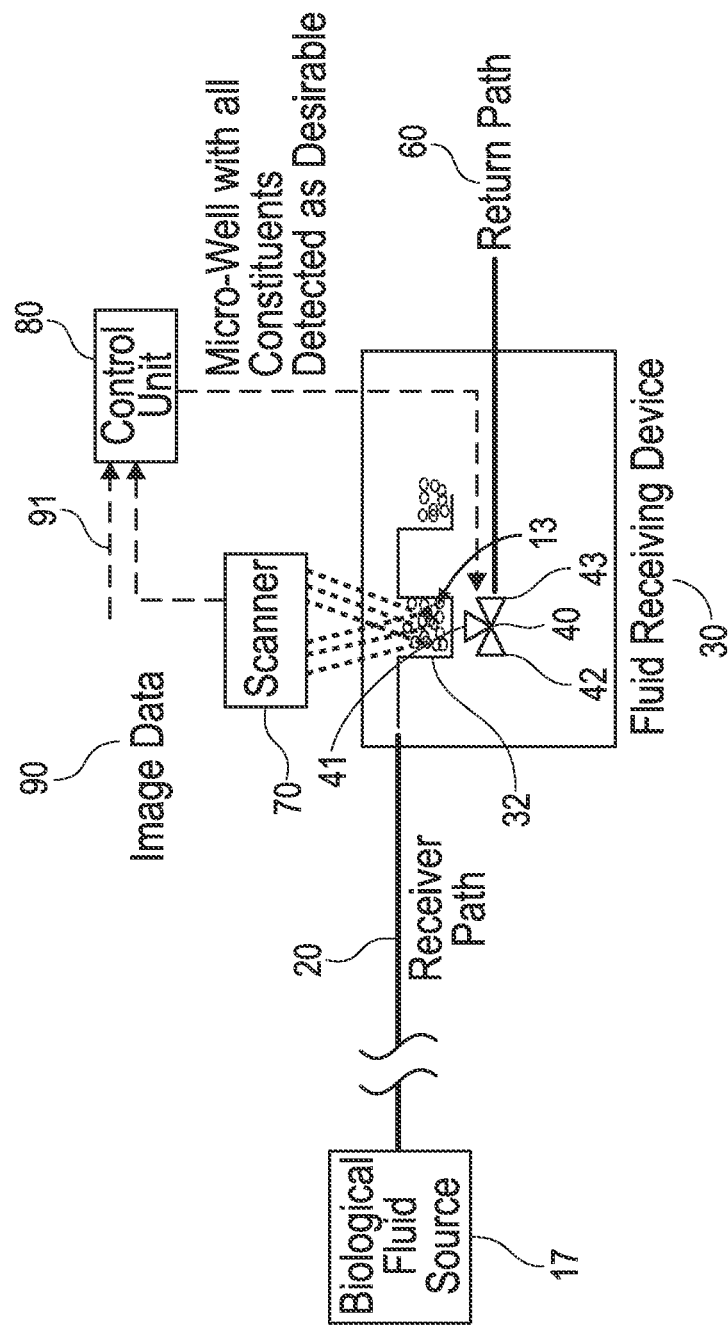
FIG. 9 is a schematic drawing of a fluid receiving device with a microwell array in accordance with an example embodiment.
Figure 10:
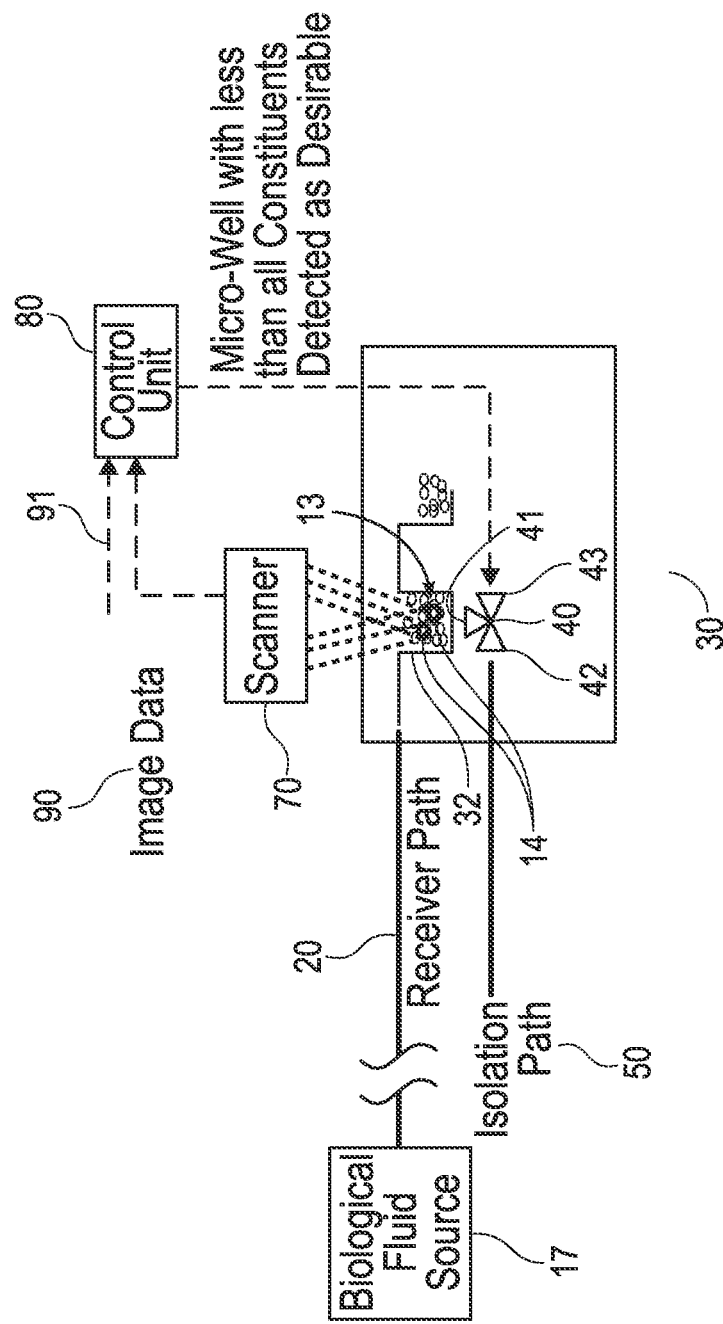
FIG. 10 is a schematic drawing of a fluid receiving device with a microwell array in accordance with an example embodiment.
Figure 11:
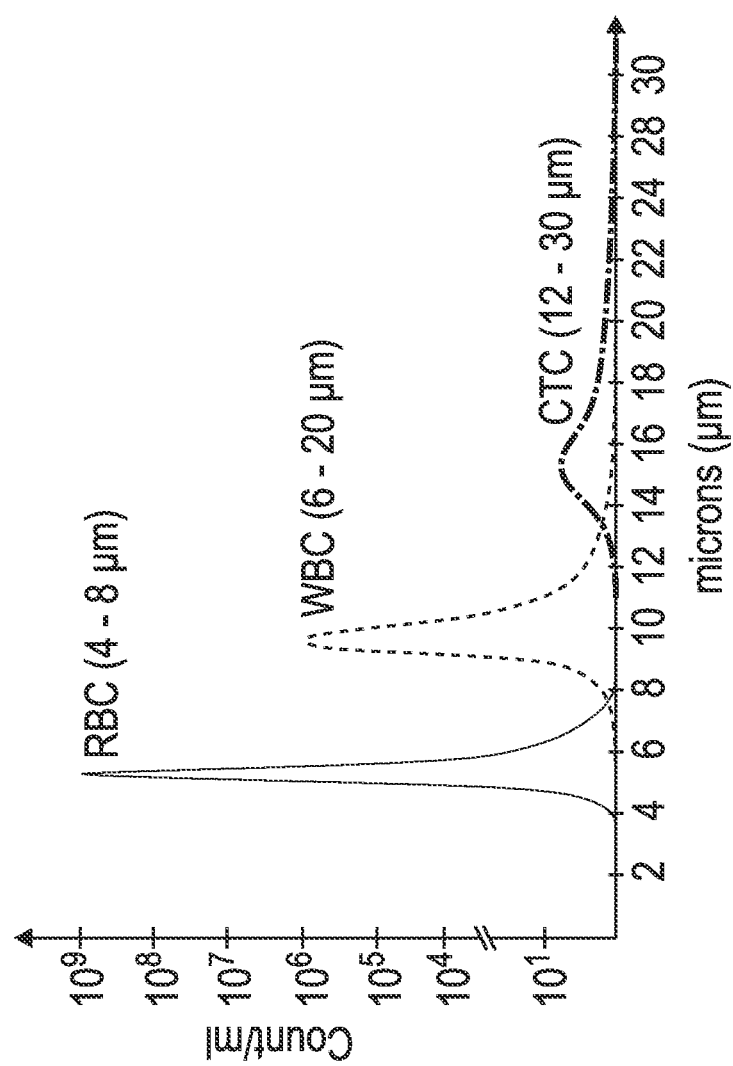
FIG. 11 is a histogram of typical cell count data in blood.

In an alternative embodiment, which is shown in FIGS. 8 and 9, the fluid receiving device 30 comprises a microwell array 32. Other suitable microfluidic devices include, e.g., glass capillary systems. In a further embodiment, best shown in FIG. 36A, the fluid receiving device 30 may comprise a microfluidic droplet generator 34.

The valve 40 is preferably a router-type micro-valve, but could include other types as well such as diaphragm-type micro-valve with electromagnetic actuation, piezo electric, thermoplastic, etc. The valve 40 is actuated by a control signal 81 sent by the control unit 80. The valve 40 can be actuated by various methods such as, for example, mechanically, electrically, piezo, electro-thermally, pneumatically, electromagnetically, by phase changes, or by introduction of external force. The valve 40 is preferably a diaphragm-type micro-valve with electromagnetic actuation. For fluid receiving devices 30 comprising multiple microfluidic channels 31 or a microwell array 32, a corresponding number of valves 40, in which each valve 40 exclusively directs the flow of contents out of a single corresponding channel or well, is preferred. However, in some example embodiments, multiple wells could share a valve 40. In other example embodiments, rather than valves 40, pipettes could be utilized to extract contents from microwells.

The isolation path 50 includes any suitable vessel or microwells for sterile delivery or transfer of a biological fluid 16 for various purposes such as in connection with clinical analysis or processing. In a preferred embodiment, biological fluid 16 directed to the isolation path is transported and stored in accordance with appropriate hematology procedures for diagnostic or conformational analysis, as described in more detail below.

The scanner 70 may comprise any device capable of scanning a biological fluid 16. The scanner 70 may comprise an optical scanner, including but not limited to a digital holographic microscope. The scanner 70 generally comprises a light source and optical detector. The scanner 70 is preferably configured to develop a multi-modal reference data 91 from which patterns characteristic of desirable constituents 15 of biological fluid 16 may be can be recognized. In an example embodiment, the scanner 70 comprises a Differential Interference Contrast Microscopy System (DIC Microscopy System). Generally, DIC Microscopy generates contrast by translating refractive index gradients of different areas of a specimen into amplitude variations that are visualized as differences in brightness. In that regard, the DIC Microscopy System is adapted to create enhanced contrast images, and is particularly suited for use in imaging unstained cell specimens exhibiting little natural visible contrast. DIC Microscopy's contrast-enhanced imaging yields information concerning cell characteristics highly relevant for many of the embodiments presented herein, including but not limited to cell solidity, cell surface characteristics, nucleus-cytoplasmic ratio, convexity, luminescence, circularity, elongation, size, inner diameter and roundness.

Other imaging devices and techniques suitable for use individually or in combination as a scanner 70, for example include, Phase contrast microscopy (PCM), Hoffman modulation, polarized light microscopy, holographic microscopy, confocal scanning optic microscopy (CSOM), or laser scanning optic microscopy (SOM) to measure voxel fluorescence, bright-field microscopy, dark-field illumination, Raman spectrometry to measure Raman Scattering, Optical interferometry to measure optical interference, total internal reflection fluorescence microscopy to measure evanescent effect, planar waveguides for refractive index detection, photonic crystal biosensors for measure of biomolecules on cell surfaces, and light property modulation detections such as surface plasmon resonance (SPR) detection.

The optical detector of the scanner 70 may comprise a single lens, or multiple linear lenses or lens arrays, and may include lenses of different shapes, for example, PCX lenses or Fresnel lenses.

In alternative embodiment, the scanner 70 and fluid receiving device 30 are combined in individual modules in a modular optofluidic system (MOPS), which permits modification or reconfiguration of modules to suit a given application.

Figure 29:
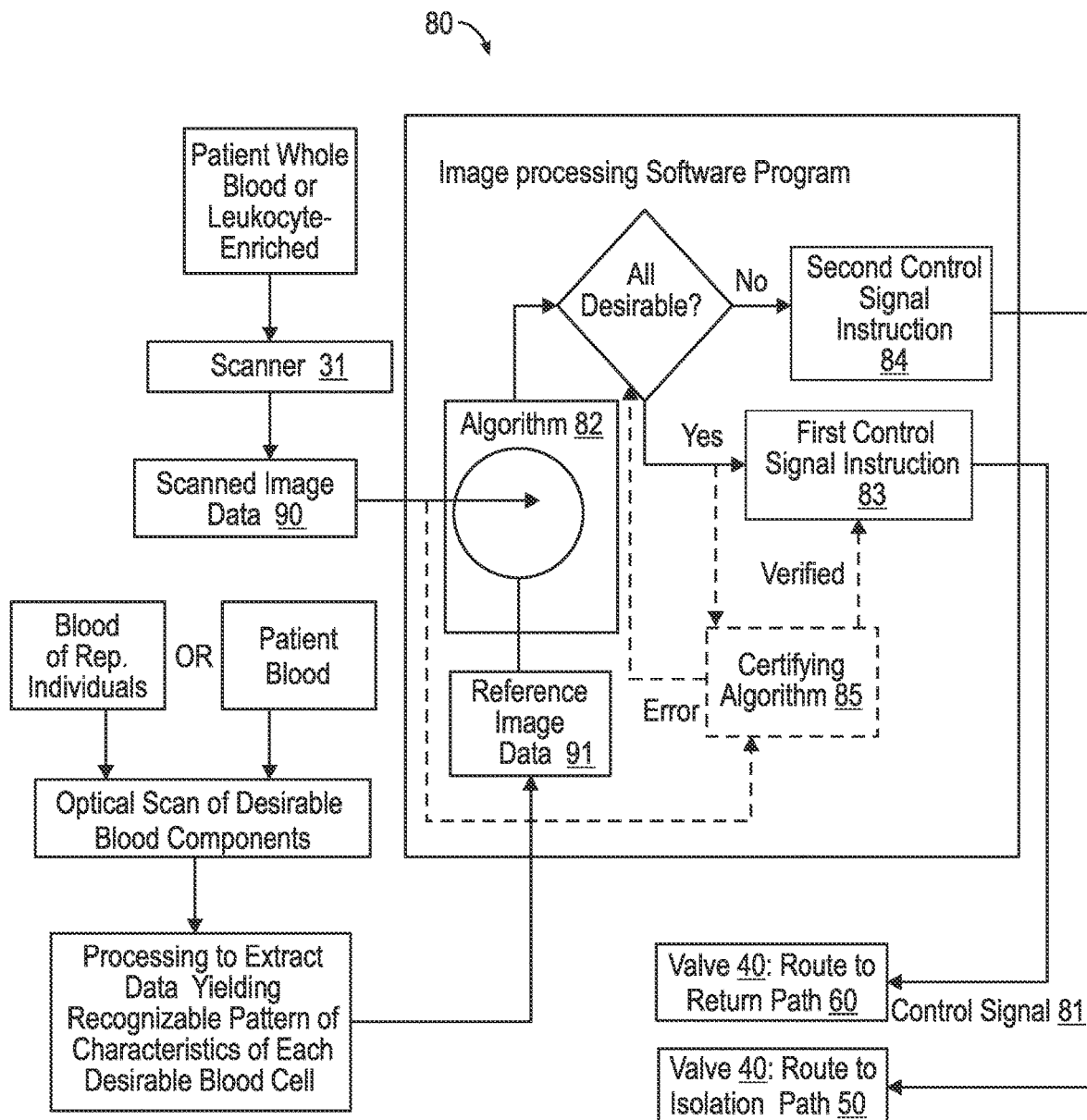
FIG. 29 is a block diagram of an aphaeretic system and method which utilizes a certifying/verification algorithm to remove undesirable pathogens from component blood fluid in accordance with an example embodiment.

The control unit 80 may be local, remote, or cloud-hosted such as through distributed networking. As shown in FIG. 29, the control unit 80 follows an image processing software program comprising an algorithm 82 (or series of algorithms) adapted to identify patterns in reference data 91 of images taken of desirable constituents 15 of a biological fluid 16 and to recognize those patterns in processing the scanned data 90 obtained by the scanner 70.

If all biological fluid constituents 13 of the scanned biological fluid 16 present in the fluid receiving device 30 at that moment sufficiently match one or more characteristics of desirable constituents 15 recognized by the algorithm 82, then the image processing software program generates a first control signal instruction 83 to the control unit 80 to relay a control signal 81 to the valve 40 to route the scanned biological fluid 16 to the return path 60.

If, on the other hand, one or more of the constituents 13 of the scanned biological fluid 16 present in the fluid receiving device 30 at that moment fails to sufficiently match patterns of desirable constituents 15 recognized by algorithm 82, then the image processing software program generates a second control signal instruction 84 to the control unit 80 to relay a control signal 81 to the valve 40 to route the scanned biological fluid 16 to the isolation path 50.

The control unit 80 may optionally also follow an additional image processing software program adapted to recognize and search for patterns in the scanned data 90 indicating the presence of an undesirable constituent 14 such as a disease-related constituent in the scanned biological fluid 16. The additional processing software program preferably comprises a certifying algorithm 85 adapted to provide validation for each control signal instruction based on a verification condition. For example, a control signal instruction to route the scanned biological fluid 16 to the return path 60 is validated only on condition that no patterns were detected in the scanned data 90 to indicate the presence of an undesirable constituent 14 such as a targeted disease-related constituent in the scanned biological fluid 16. If the condition is not satisfied, a corrected instruction is issued to route the scanned biological fluid 16 to the isolation path 50.

In one embodiment, the reference data 91 is derived based on normative data for recognized desirable constituents 15 of the biological fluid 16 within a relevant reference population. In another embodiment, the reference data 91 is derived by imaging biological fluid 16 samples obtained from representative individuals in the relevant reference population. In other embodiments, the reference data 91 may at least partially be derived from a pre-filtration session with a particular patient 12.

In such an embodiment, as illustrated in FIGS. 12-17 and 19, the reference data 91 is obtained based on imaging of a fluid sample of the subject patient's biological fluid system during a pre-filtration session. Because the reference data 91 of the embodiment is patient specific, data ambiguity based on constituent heterogeneity is avoided. Accordingly, the algorithm 82, which may rely upon machine learning, is configured to more precisely identify patterns of desirable constituents 15 in the subject-specific reference data 91 and thus more precisely recognize desirable constituents 15 of the scanned data 90 taken of the subject biological fluid source 17 during filtration.

In some embodiments, machine learning and/or artificial intelligence models may be utilized to develop and optimize the reference data 91. By way of example, samples of biological fluids 16 from the patient 12 or from others May be analyzed to identify desirable constituents 15 of the biological fluid 16 through machine learning. Such a system may be more easily accomplished with relation to healthy cells which are common to all patients 12, such as red blood cells, white blood cells, and the like. This is a result of consistency of the characteristics or images of such healthy cells and the availability of a large sample size. With respect to undesirable constituents 14, machine learning and/or artificial intelligence models may also be applied, though with a smaller sample size and with the caveat that certain unhealthy cells such as CTCs may have different characteristics in different patients 12. Additionally, the scanned data 90 may also be analyzed using machine learning and/or artificial intelligence models. Further, the process of comparing the scanned data 90 with the reference data 91, and the resulting determination by the control unit 80, may also utilize machine learning and/or artificial intelligence models.

Figure 16:
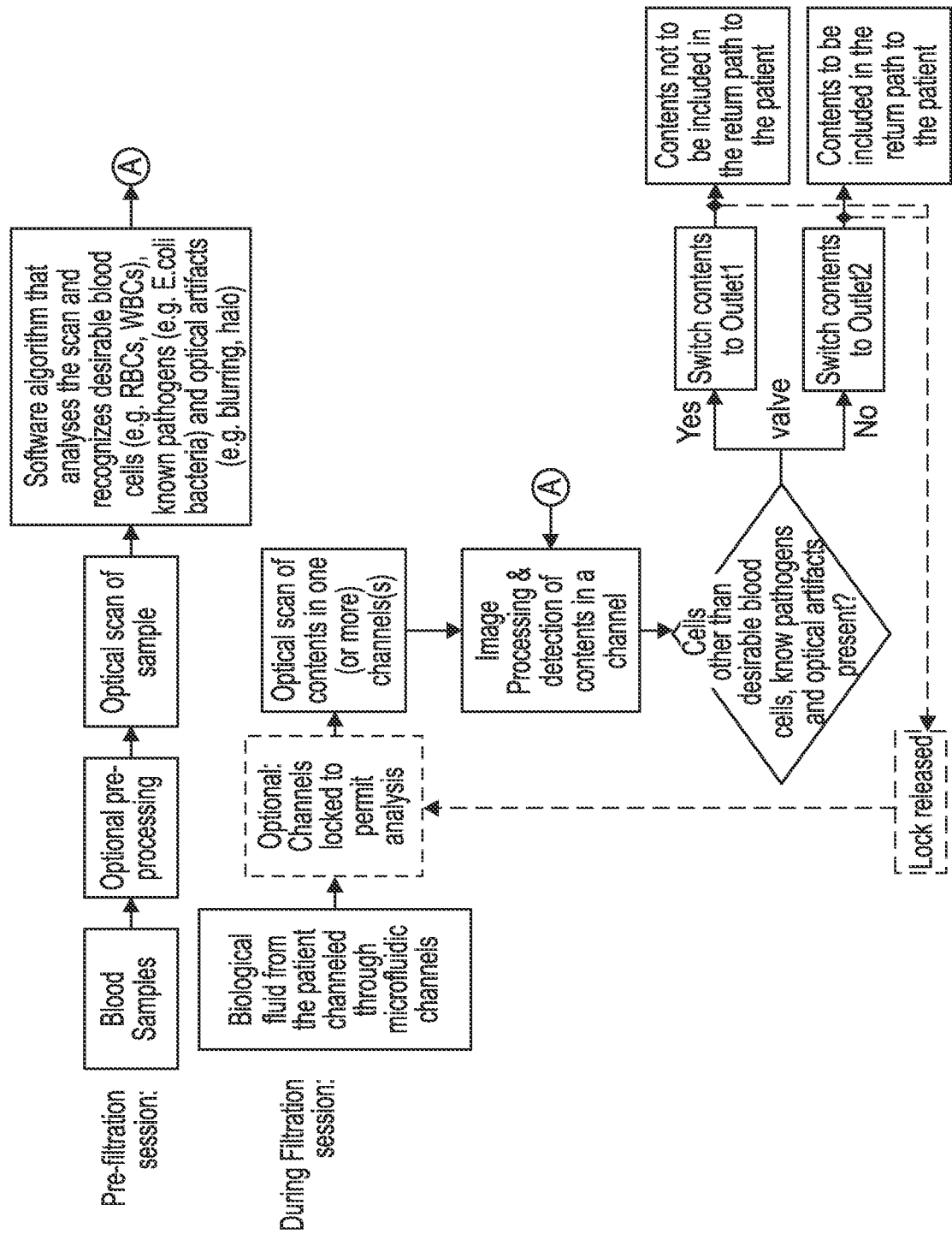
FIG. 16 is a block diagram of an aphaeretic system and method incorporating image data of known pathogens and optical artifacts into a reference data in accordance with an example embodiment.

In another embodiment, as illustrated in FIG. 16, the reference data 91 includes imaging data allowing the control unit 80 to discern optical artifacts, e.g., halos, air bubbles, or blurring, to avoid errors where characteristics of such artifacts in the imaging data might otherwise trigger an erroneous second control signal instruction 84 to direct fluid containing only desirable constituents 15 to the isolation path 50. For the same reason, the reference data 91 may include imaging data allowing the control unit 80 to discern non-targeted biological entities, e.g., benign bacteria.

In another embodiment, the biological fluid filtration system 10 conducts a continuous-flow microfluidic operation. In such an embodiment, the biological fluid 16 may continuously flow through the fluid receiving device 30 as the biological fluid 16 is scanned. In an alternative embodiment, as illustrated in FIGS. 12-16, the microfluidic channel 31 includes an inlet valve 33 such as a channel lock adapted to suspend fluid flow while biological fluid 16 in the microfluidic channel 31 is scanned.

In yet another embodiment, which is illustrated in FIGS. 2, 15, 17, 18, and 20-22, the biological fluid filtration system 10 performs pre-processing on the biological fluid 16 using a microfluidic separation module 100 to separate particular cellular constituents of the biological fluid 16 for promotion to the fluid receiving device 30. Suitable pre-processing devices and techniques suitable May rely on a variety of cell-characteristics to perform separation including, size, density, inertial hydrodynamic, antigen binding affinity, acoustics, motility, electric charge, electric dipole moment, centrifugation, or magnetism. Some techniques might also involve the use of buffer solutions.

In one embodiment, in which blood is filtered for removal of CTCs, whole blood is pre-processed to separate leukocytes from smaller-sized blood constituents (i.e., erythrocytes, thrombocytes, plasma) and large CTCs or CTC-clusters. The separated, leukocyte-enriched blood, which contains small CTCs, is promoted to the fluid receiving device 30 for scanning and filtering. CTC-free leukocytes along with the other separated healthy blood constituents are returned to the subject's circulatory system, and the separated large and small CTCs or CTC-clusters are sequestered.

The other separated blood constituents can optionally be subjected to additional filtering before being returned to the subject's circulatory system. For example, as illustrated in FIGS. 23-26, separated small blood constituents can be subject to antigen-based filtration to remove proteins that promote metastasis, including aiding in CTC extravasation and evasion of immune response, e.g., cytokines, chemokines, and growth factors released by tumor-associated macrophages. Antigen-based filtration may also be optionally used to compliment both pre-processing and optical scanning and filtering processes to remove any remaining CTCs in pre-processed or optically scanned and filtered biological fluids 16 before being returned to the subject.

In an exemplary embodiment, which is shown in FIGS. 1-4, the biological fluid 16 is blood, the biological fluid source 17 is the patient 12, and the biological fluid filtration system 10 is an aphaeretic system that circulates blood from the circulatory system of a patient 12, removes undesirable constituents 14 from the blood, and then returns the filtered, healthy blood back to the circulatory system. Such a biological fluid filtration system 10 has equal application to other biological fluids 16, including, for example, cerebrospinal fluid, lymphatic fluid, and the various other fluids described herein.

Figure 3:
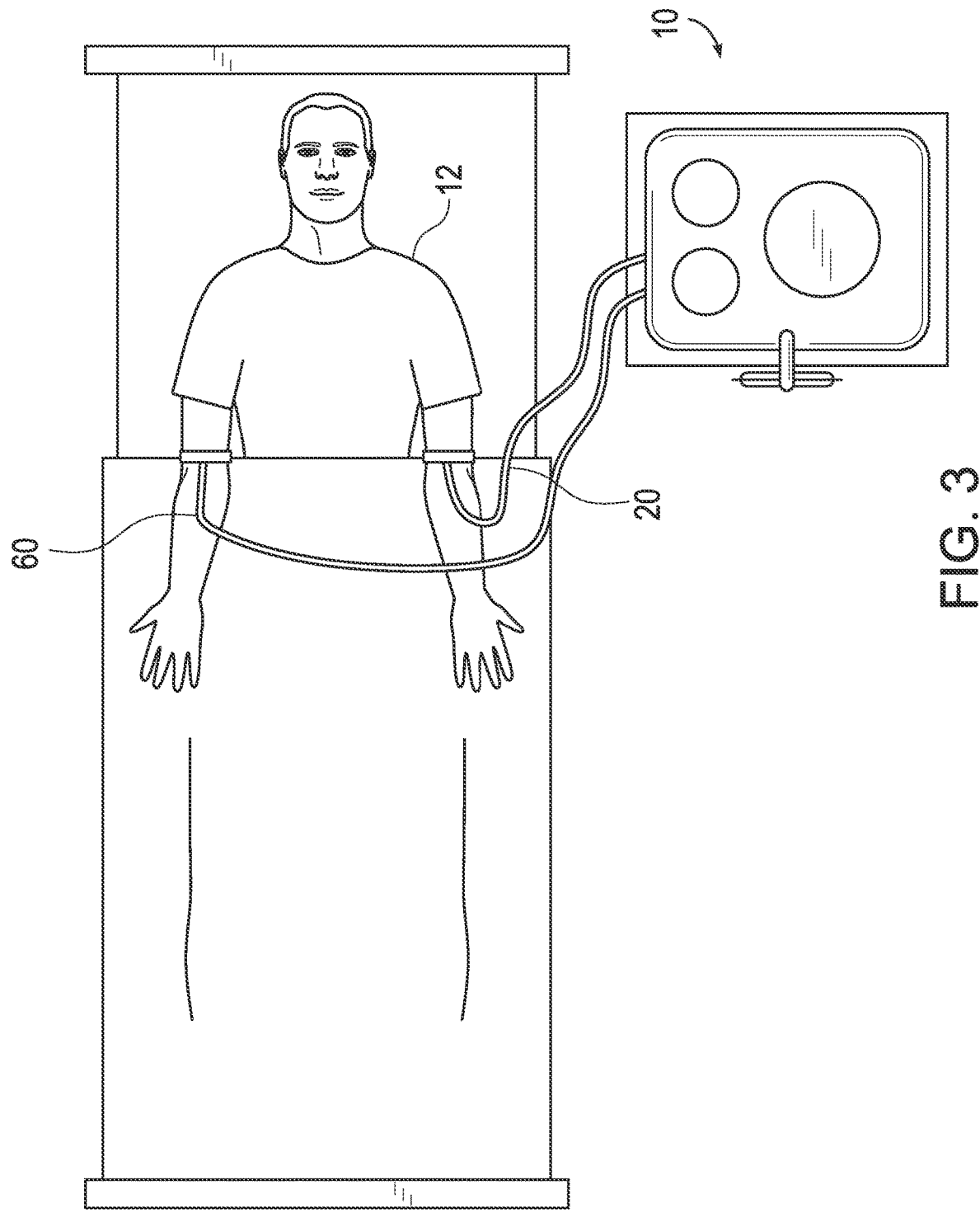
FIG. 3 is a perspective view of a biological fluid filtration system in accordance with an example embodiment.
Figure 4:
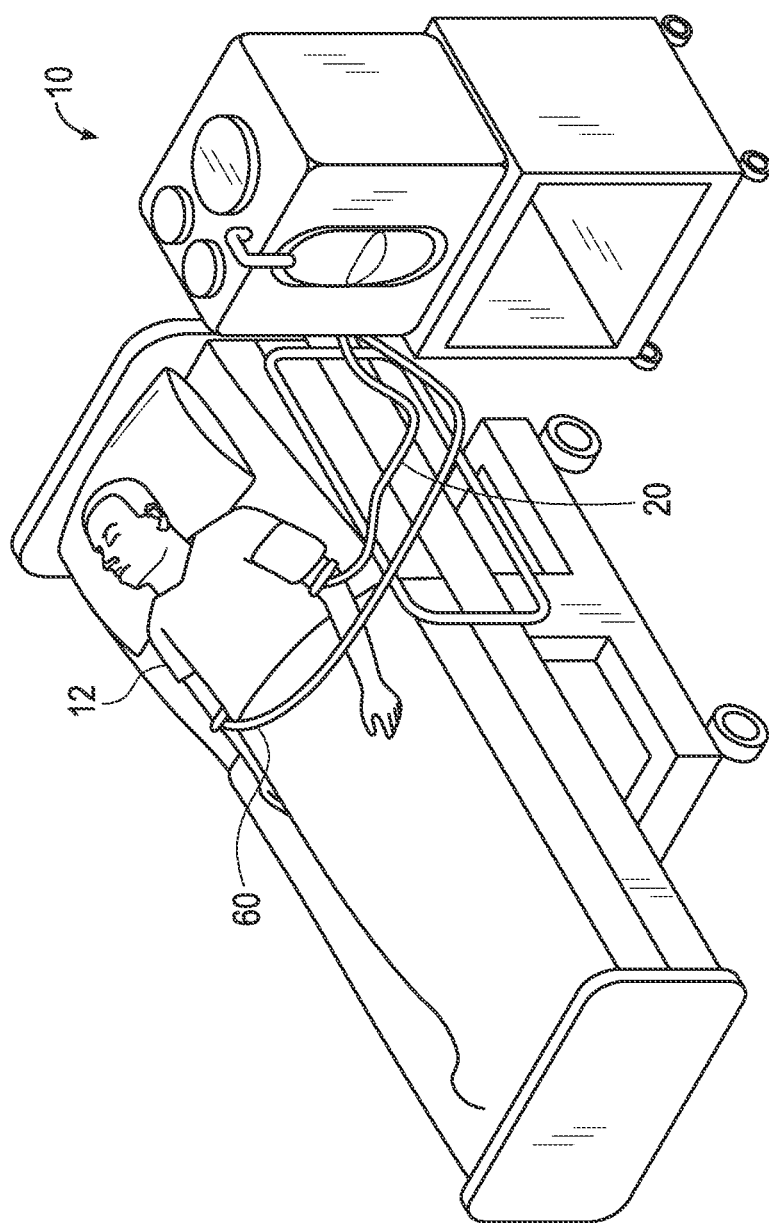
FIG. 4 is a perspective view of a biological fluid filtration system in accordance with an example embodiment.

The biological fluid filtration system 10 can be applied as a therapeutic, a diagnostic system, or both. In one embodiment, a patient's pathology is determined and the particular cancer-associated CTCs or disease causative agent identified, and the system is adapted to filter out the known CTCs or agents from patients the biological fluid system. In such an embodiment as illustrated in FIGS. 3 and 4, the receiver path 20 is adapted to receive and facilitate flow of biological fluid 16 from the patient 12 via, e.g., a cannula and venous catheter assembly, to the fluid receiving device 30.

Figure 2:
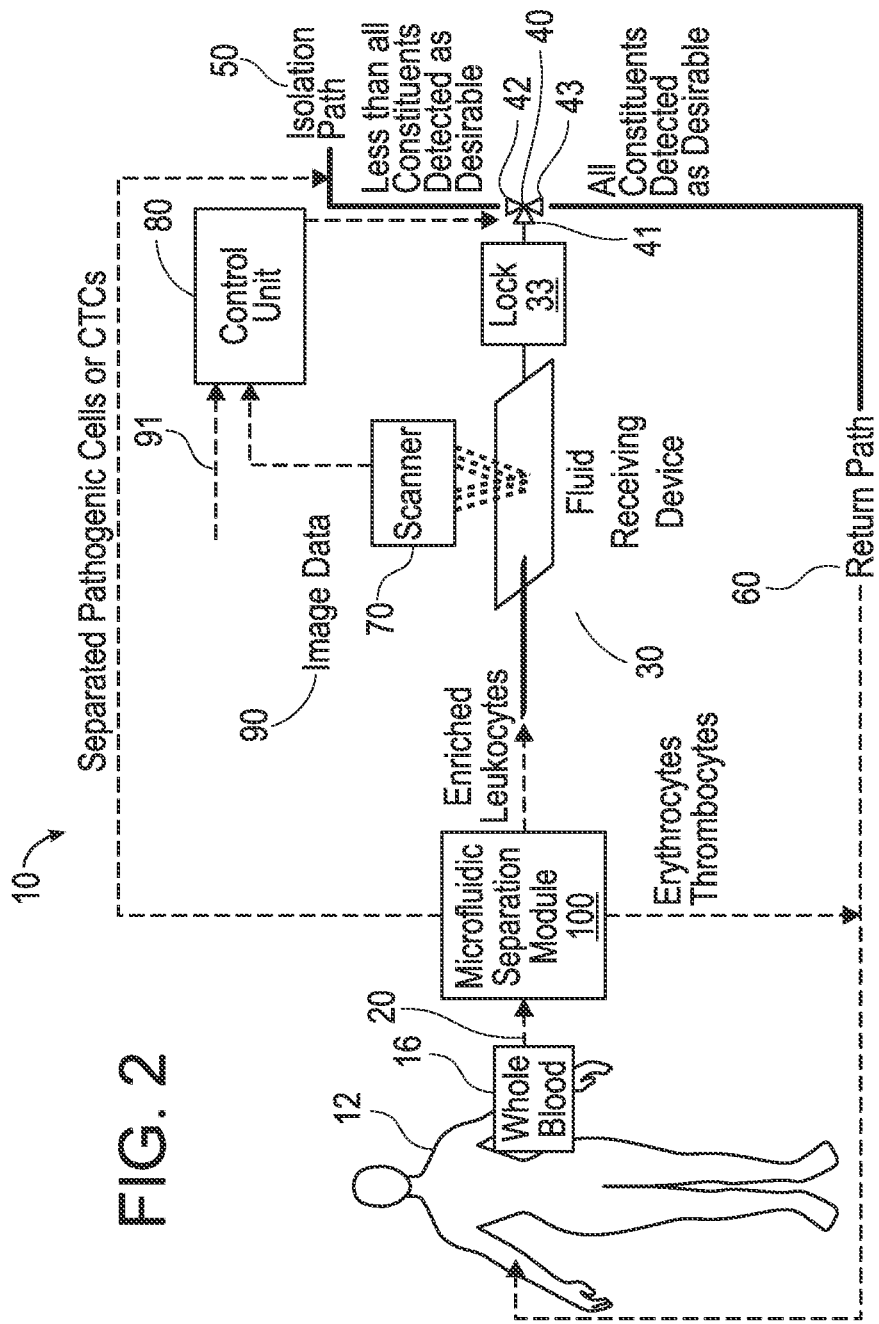
FIG. 2 is a perspective view of a biological fluid filtration system in accordance with an example embodiment.

As shown in FIGS. 1 and 2, the scanner 70 is adapted to optically scan the biological fluid 16 on or within the fluid receiving device 30 so as to derive a scanned data 90 of the biological fluid 16 and relay the scanned data 90 to the control unit 80. The control unit 80 is adapted to compare the scanned data 90 of the biological fluid 16 with a reference data 91 to relay a control signal 81 to the valve 40 to route healthy biological fluid 16 to the return path 60 and sequester biological fluid 16 containing CTCs or undesirable disease causative agents to the isolation path 50, as described herein. The return path 60 is adapted to receive and facilitate flow of healthy biological fluid 16 from the fluid receiving device 30 via the valve 40, and returning the fluid 16 to the patient 12 via, e.g., a cannula and venous catheter assembly. In another embodiment, the sequestered biological fluid 16 is diagnostically processed for conformational analysis.

Figure 14:
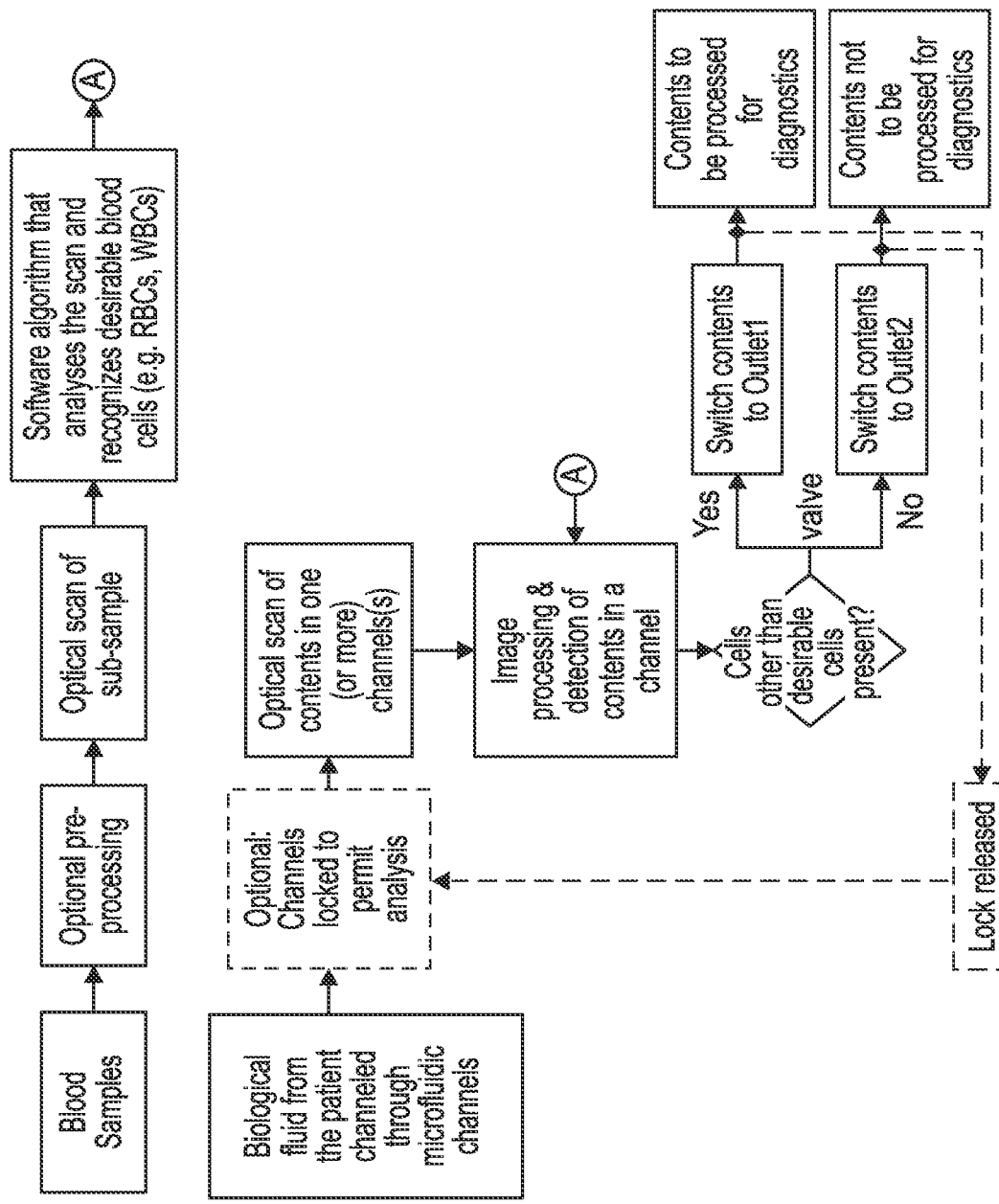
FIG. 14 is a block diagram of a diagnostic system in accordance with an example embodiment.

In another embodiment, which is shown in FIG. 14, a subject's pathology is undetermined, and the system is adapted to filter out undesirable constituents 14 not recognized by the system as meeting pre-determined criteria characteristic of desirable constituents 15 of the subject biological fluid 16, as described herein. As with the therapeutic system described above, the scanner 70 of the diagnostic system is adapted to optically scan the biological fluid 16 within the fluid receiving device 30 so as to derive the scanned data 90 of the biological fluid and relay the scanned data 90 to the control unit 80, and, in turn, the control unit 80 is adapted to compare the scanned data 90 of the biological fluid 16 with the reference data 91 and relay a control signal 81 to the valve 40 to route healthy biological fluid 16 to the return path 60 and sequester biological fluid 16 containing undesirable constituents 14, such as undesirable, indeterminate biological agents, as described herein. If used for diagnostic purposes, in some embodiments, such a system could be used for early detection of the signs of cancer in the patient. In such diagnostic systems, even the filtered fluid containing healthy components may not be returned back to the subject.

The sequestered biological fluid 16 is then subject to diagnostic testing to identify the undesirable constituents 14 present in the sequestered biological fluid 16. In the diagnostic embodiment, the receiver path 20 is optionally adapted to receive and facilitate flow of biological fluid 16 from the patient's biological fluid system and the return path 60 is optionally adapted to return healthy biological fluid 16 to the patient's biological fluid system. In one embodiment, the receiver path 20 and return path 60 are respectively adapted to receive and return biological fluid 16 from the subject's biological fluid system, the diagnostic system is adapted to both diagnose and filter out undesirable constituents 14 in the subject's biological fluid system. In an alternative embodiment, the receiver path 20 is adapted to receive and facilitate flow of a biological fluid 16 sample taken of the subject's biological fluid system, and the healthy biological fluid 16 routed to the return path 60 is processed for storage or disposal.

Figure 36A:
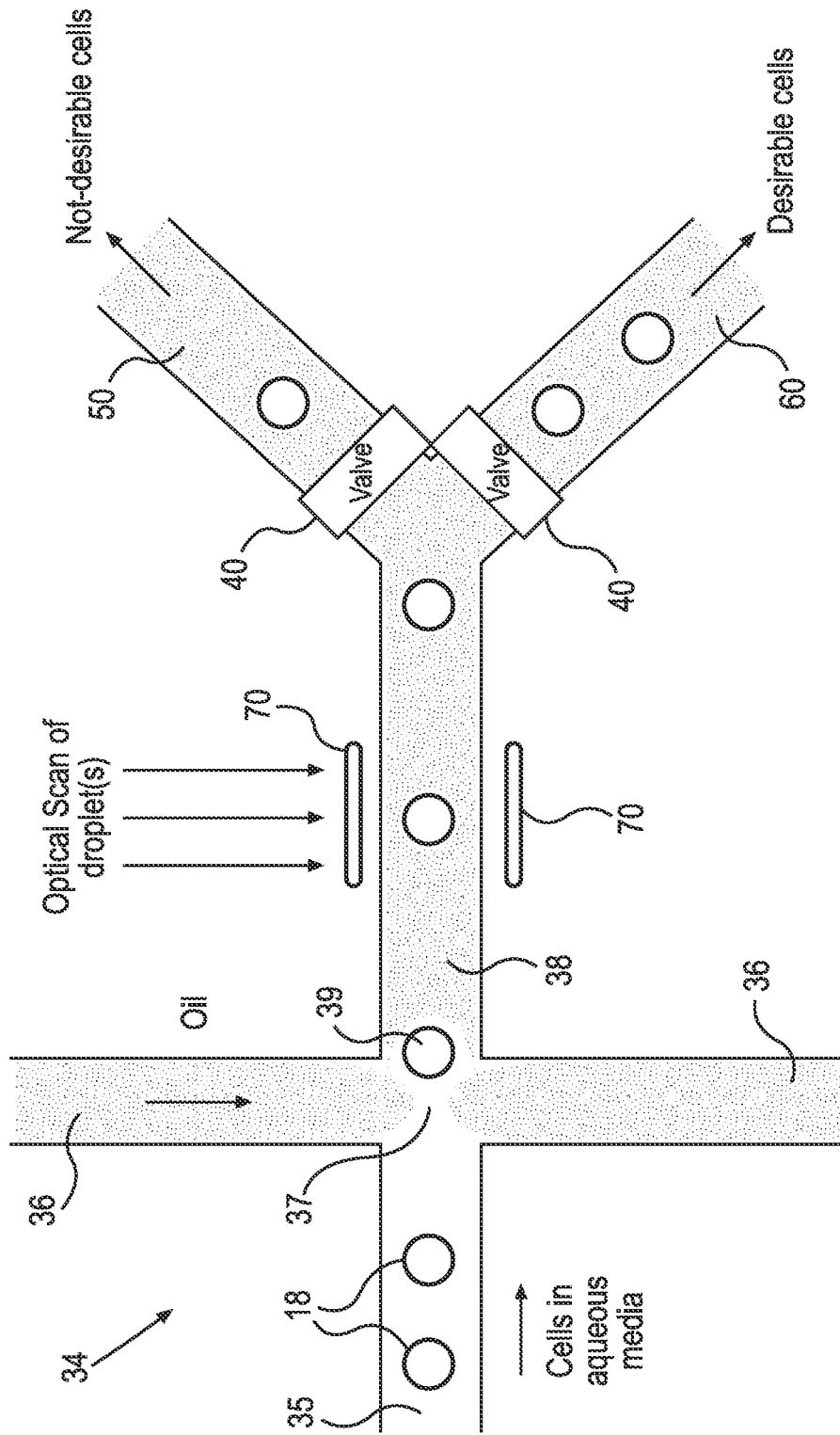
FIG. 36A is a block diagram illustrating a system and method of filtering a biological fluid including a fluid receiving device utilizing droplet sorting in accordance with an example embodiment.
Figure 36B:
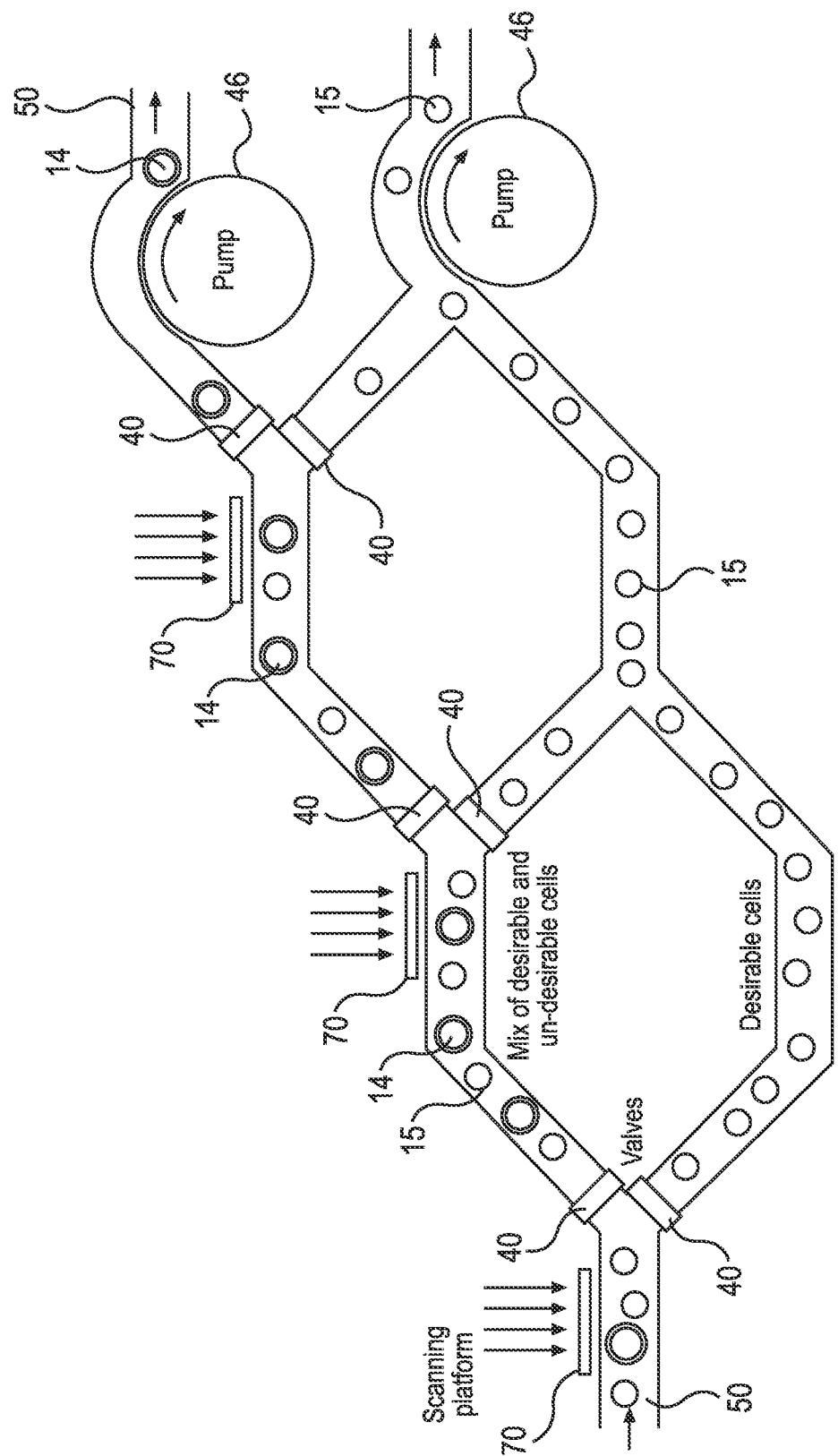
FIG. 36B is a block diagram illustrating additional channels added after an isolation path of a biological fluid filtration system in accordance with an example embodiment.

In some embodiments such as shown in FIG. 36B, the isolation path 50 may further bifurcate into additional channels and valves 40, with each such bifurcated additional channel including its own fluid receiving device 30 and scanner 70. The geometry of such additional channels could be of various shapes, including without limitation rectangular, serpentine, spiral, circular, square, or combinations thereof. The geometry of the exemplary embodiment shown in FIG. 36B should thus not be construed as limiting.

Continuing to reference FIG. 36B, additional channels may be added after the isolation path 50 of any of the embodiments described and shown herein. Contents from such an isolation path 50 are scanned in multiple additional stages for further enrichment of the biological fluid 16. As shown in FIG. 36B, contents from an isolation path 50 enter an additional fluid receiving device 30 and are scanned again by a scanner 70. The resulting scanned data 90 is processed by the control unit 80. Valves 40 are provided to direct the contents into additional stages, with the valves 40 being operated by the control unit 80 based on the results of its processing of the contents. In exemplary embodiments utilized in an aphaeretic setting, any contents including only healthy cells (e.g., desirable constituents 15) are carried forward, such as back to the biological fluid source 17 via a return path 60.

Contents which include a mixture of healthy and non-healthy cells (e.g., any contents including undesirable constituents 14) are directed along an additional channel to an additional fluid receiving device 30 and are scanned again by a scanner 70. After the additional fluid receiving device 30, valves 40 are provided to bifurcate the additional channel such that contents including only healthy cells may be diverted towards a return path 60. Contents including non-healthy cells such as undesirable constituents 14 are directed along an additional channel to an additional fluid receiving device 30 and are scanned again by a scanner 70. This process may be repeated any number of times, with healthy cells being carried forward to be isolated or returned, and any unhealthy cells being scanned additional times.

As shown in FIG. 36B, pumps 46 may be utilized to regulate flow rates of the biological fluid 16 through the various channels. The pumps 46 may comprise pressure pumps, syringes, peristaltic, and the like. The scanning techniques could vary across successive stages or sections (e.g., DHM, digital inline holography, etc.) and the algorithms utilized to identify cells may also vary (e.g., neural network type classifiers to decision trees, etc.). In other example embodiments, such an arrangement could involve droplets 39 as opposed to cells in media.

C. Fluid Receiving Device.

As described and shown herein, a wide range of fluid receiving devices 30 may be utilized for the biological fluid filtration system 10 in combination with various types of biological fluids 16, including but not limited to blood and/or leukapheresis extracts. The fluid receiving device 30 may comprise a microfluidic platform. In a first exemplary embodiment as shown in FIG. 5, the fluid receiving device 30 may comprise one or more microfluidic channels 31. In a second exemplary embodiment as shown in FIG. 8, the fluid receiving device 30 may comprise a microwell array 32. In a third exemplary embodiment as shown in FIG. 36A, the fluid receiving device 30 may comprise a microfluidic droplet generator 34. It should also be appreciated that various other types of fluid receiving devices 30 may be utilized.

It should be appreciated that, in some embodiments, multiple types of fluid receiving devices 30 may be grouped together. For example, an exemplary fluid receiving device 30 may comprise both microfluidic channels 31 and a microwell array 32, arranged together in parallel or in series. As a further example, a fluid receiving device 30 may comprise both microfluidic channels 31 and a droplet generator 34. As yet another example, a fluid receiving device 30 may comprise microfluidic channels 31, a microwell array 32, and a droplet generator 34 all configured to work in concert. Additionally, in some embodiments, there could be multiple successive valves 40 and fluid receiving devices 30 attached to a single outlet to enrich the contents of a microchannel.

As shown in FIG. 5, an exemplary embodiment of the fluid receiving device 30 may comprise one or more microfluidic channels 31. The microfluidic channels 31 will generally comprise networks of one or multiple channels through which biological fluids 16 may be routed to be processed using the systems and methods described herein. In some embodiments, a single microfluidic channel 31 may be utilized, such as with an embodiment effectuating single-stage processing of a single biological fluid 16. In other embodiments, multiple microfluidic channels 31 may be utilized, such as with an embodiment effectuating multi-stage processing of a single biological fluid 16, or single-stage processing of multiple biological fluids 16 simultaneously.

By way of example, multiple fluid receiving devices 30 may be arranged in parallel so as to allow for multiple biological fluids 16, either from the same or different biological fluid sources 17, to be simultaneously scanned and then routed accordingly. In this manner, multiple types of biological fluids 16 from the same or multiple biological fluid sources 17 may be processed simultaneously. By way of example, a first biological fluid 16 may be processed in a first fluid receiving device 30 and a second biological fluid may be processed in a second fluid receiving device 30. Additional fluid receiving devices 30 may similarly be operated in parallel to suit any number of biological fluids 16.

As a further example, multiple fluid receiving devices 30 may be arranged in series such that a single biological fluid 16, or multiple biological fluids 16, may be scanned multiple times in multiple stages. For example, a first fluid receiving device 30 may process a biological fluid 16 a first time, and then the biological fluid 16 may be transferred to a second fluid receiving device 30 in series with the first fluid receiving device 30 so as to process the biological fluid 16 a second time. Subsequent fluid receiving devices 30 may also be added, allowing for multi-stage separation of the biological fluid 16 as discussed herein. In some embodiments, multiple fluid receiving devices 30 may be arranged both in parallel and in series so as to allow simultaneous, multi-stage processing of multiple biological fluids 16.

The microfluidic channels 31 may be fabricated from polymeric materials, including but not limited to polymethylmethacrylate, cylic olefin copolymer (COC), polycarbonate, polydimethylsiloxane (PDMS), SU-8 photoresist, and the like. As previously discussed, the microfluidic channels 31 may comprise various topographies, geometries, and patterns, and thus should not be construed as limited by the exemplary topographies, geometries, and patterns shown in the exemplary figures.

The microfluidic channels 31 may be arranged in a multilayer, 2-dimensional or 3-dimensional configuration. Moreover, various channel geometries may be employed including, for example, curvilinear and spiral geometries. Various channel patterns in addition to parallel patterns may be suitable including, for example, knot, basket-weave, and braided patterns. By way of example and without limitation, the microfluidic channels 31 may be straight, curved, or helical. Where multiple microfluidic channels 31 are utilized, the plurality of microfluidic channels 31 may be arranged in parallel. In other embodiments, one or more microfluidic channels 31 may cross paths without being fluidly interconnected.

The microfluidic channels 31 may be formed of various materials including polymers, such as silicon, glass or polymers, e.g., polydimethylsiloxane (PDMS). In some embodiments, the microfluidic channels 31 may be stacked on top of each other. The positioning, orientation, and arrangement of the microfluidic channels 31 may vary and thus should not be construed as limited by the exemplary FIGS. or description herein.

As shown in FIG. 8, another exemplary embodiment of the fluid receiving device 30 may comprise one or more microwell arrays 32. Each microwell array 32 will generally comprise an array of microwells into which the biological fluid 16 may be transferred for scanning by the scanner 70 using the various techniques discussed herein. The shape, size, and density of the individual wells of the microwell array 32 used herewith may vary in different embodiments.

The number of microwell arrays 32 utilized for scanning each biological fluid 16, or for scanning multiple biological fluids 16, may vary in different embodiments. In some embodiments, a single microwell array 32 may be utilized such as shown in FIG. 8. In other embodiments, multiple microwell arrays 32 may be utilized, such as for scanning multiple biological fluids 16 simultaneously or in-turn.

By way of example, multiple microwell arrays 32 may be arranged in parallel so as to allow for multiple biological fluids 16, either from the same or different biological fluid sources 17, to be simultaneously scanned and then routed accordingly. In this manner, multiple types of biological fluids 16 from the same or multiple biological fluid sources 17 may be processed simultaneously. By way of example, a first biological fluid 16 may be processed in a first microwell array 32 and a second biological fluid 16 may be processed in a second microwell array 32. Additional microwell arrays 32 may similarly be operated in parallel to suit any number of biological fluids 16. Some embodiments could combine the use of microwell arrays 32 and microfluidic channels 31.

As a further example, multiple microwell arrays 32 may be arranged in series such that a single biological fluid 16, or multiple biological fluids 16, may be scanned multiple times in multiple stages. For example, a first microwell array 32 may process a biological fluid 16 a first time, and then the biological fluid 16 may be transferred to a second microwell array 32 in series with the first microwell array 32 so as to process the biological fluid 16 a second time. Subsequent microwell arrays 32 may also be added, allowing for multi-stage separation of the biological fluid 16 as discussed herein. In some embodiments, multiple microwell arrays 32 may be arranged both in parallel and in series so as to allow simultaneous, multi-stage processing of multiple biological fluids 16.

It should also be appreciated that the type of microwell array 32 may vary in different embodiments. The microwell array 32 may comprise single-use wells (e.g. parylene valves) or multi-use wells (e.g., piezo locks). The number of microwells included in each microwell array 32 may vary in different embodiments to suit different applications. Further, the manner in which the biological fluid 16 is introduced into the microwell array 32 may vary in different embodiments. By way of example and without limitation, the biological fluid 16 may be introduced into the microwell array 32 utilizing pumps, valves, microfluidic devices, pipettes, or various combinations thereof.

As best shown in FIG. 36A, another exemplary embodiment of a fluid receiving device 30 may comprise a droplet generator 34 in which cells are encapsulated within droplets 39 such that the droplets 39 may be scanned by the scanner 70. Such an embodiment may rely on the use of droplets 39 to compartmentalize cells in nanoliter scale compartments. Similar systems have been previously used as reaction chambers for transcriptomic analysis. Utilizing the systems and methods described herein, cells may be encapsulated into droplets 39. Those droplets 39 may then be scanned by the scanner 70 to differentiate between healthy cells (e.g., normal blood cells) or unhealthy cells (e.g., cancer cells). The generated droplets 39 may comprise various shapes and sizes. The generated droplets 39 may be spherical or non-spherical (e.g., oblong).

In an embodiment utilizing droplet sorting such as shown in FIG. 36A, a defined microfluidic channel-cross design, such as a droplet generator 34, may be utilized. Using the droplet generator 34, two or more immiscible phase channels 35, 36 will generally meet at an angle to generate droplets 39. A first exemplary immiscible phase may comprise a dispersed phase channel 35 through which an aqueous solution containing cells 18 may be routed. A second exemplary immiscible phase channel may comprise one or more continuous phase channels 36, through which oil may be routed.

Continuing to reference FIG. 36A, it can be seen that the dispersed phase channel 35 includes an aqueous solution containing cells 18 from the biological fluid 16. The continuous phase channel 36 includes oil or oils which are immiscible with the aqueous solution. The dispersed phase channel 35 and continuous phase channel 36 meet at a juncture 37 at an angle such that droplets are generated which compartmentalize the cells to be scanned. In the embodiment shown in FIG. 36A, multiple continuous phase channels 36 are utilized.

As can be seen in FIG. 36A, the juncture 37 may comprise a four-way juncture 37 having a single dispersed phase channel 35, a pair of continuous phase channels 36, and a scanning channel 38 wherein the droplets 39 containing compartmentalized cells 18 are scanned. It should be appreciated, however, that such a configuration of the juncture 37 and associated channels 35, 36, 38 may vary in different embodiments. For example, in some embodiments, only a single continuous phase channel 36 may be utilized.

The angle at which the dispersed phase channel 35 and continuous phase channel(s) 36 converge at the junction 37 may vary in different embodiments. In the exemplary embodiment shown in the figures, a pair of continuous phase channels 36 meets at right angles with a single dispersed phase channel 35. However, various other angles may be utilized in different embodiments to suit different applications. Further, the angle of the scanning channel 38 with respect to the dispersed phase channel 35 and continuous phase channel(s) 36 may also vary in different embodiments.

The flow rates of the respective phase channels 35, 36 define the throughput of the system. The flow rate within the respective phase channels 35, 36 may vary in different embodiments. Generally, the flow rate of the dispersed phase channel 35, generally containing cells 18 from the biological fluid 16 in an aqueous media, such as an aqueous solution, will be greater than the flow rate of the continuous phase channel 36, generally containing an oil. However, different flow rates may be utilized to suit different biological fluids 16, scanners 70, or other considerations. Further, the rate of flow through the scanning channel 38 may vary in different embodiments. In some embodiments, the scanning channel may include a channel lock such as an inlet valve 33 so as to pause or reduce flow rate while cells 18 are being scanned.

The size of the droplet generator 34 and the ratio of the dispersed phase channel 35 when compared with the continuous phase channel 36 will generally define the size of generated droplets 39 exiting the juncture 37. Thus, the size of the droplet generator 34, and the ratio of the sizes of the dispersed phase channel 35 and continuous phase channel 36, may vary in different embodiments to suit different sizes of generated droplets 39 to be scanned by the scanner 70. Accordingly, the size of the droplet generator 34 and ratio between the respective phase channels 35, 36 should not be construed as the exemplary embodiment shown in FIG. 36A.

Cells 18 of the biological fluid 16 are routed first through the dispersed phase channel 35 in an aqueous media such as an aqueous solution. The aqueous media containing the cells 18 from the biological fluid 16 passes through the juncture 37, at which point oil from the continuous phase channel(s) 36 is introduced to encapsulate the cells 18 in droplets 39, with the oil being immiscible with the aqueous solution so as to generate the droplets 39. FIG. 36A illustrates that oil is introduced at a right angle from two separate continuous phase channels 36. It should be appreciated that oil may be introduced at various other angles, and more or less continuous phase channels 36 may be utilized than are shown in the exemplary embodiment shown in the figures.

In an exemplary embodiment, individual droplets 39 exit the juncture 37 through a scanning channel 38 to pass a scanner 70 such as a digital holographic microscope. The scanner 70 is configured to scan each droplet 39 as it passes out of the juncture 37 and through the scanning channel 38. The scanner 70 may be configured to scan each droplet 39 within the scanning channel 38 separately in-turn, or may be configured to scan multiple droplets 39 simultaneously. In some embodiments, multiple droplets 39 may be scanned simultaneously within the scanning channel 38 to determine if any of the droplets 39 encapsulate cells 18 that are undesirable or malignant; with the droplets 39 being sorted by diverting the flow of the droplets 39 according to the scan results.

The results from the scanner 70 are then analyzed, such as by a control unit 80, to determine if the encapsulated cells 18 within each droplet 39 are healthy or unhealthy (e.g., malignant). If the cells 18 are healthy, those cells 18 may be separated from other cells 18 (e.g., malignant cells) by use of one of a pair of valves 40. In the exemplary embodiment shown in FIG. 36A, it can be seen that a first valve 40 leads to a return path 60 for healthy cells and a second valve 40 leads to an isolation path 50 for all other cells 18 (unidentified cells 18 or malignant cells 18).

When a healthy cell 18 is scanned by the scanner 70, the first valve 40 is opened and the second valve 40 is closed. When an undesirable or malignant cell 18 is scanned by the scanner 70, the second valve 40 is opened and the first valve 40 is closed. The first valve 40 may lead to a return path 60 such that healthy cells 18 may be returned to the patient 12 for therapeutic purposes, or may lead to an isolation path 50 to be sequestered for diagnostic purposes. The second valve 40 may lead to an isolation path 50 to be sequestered.

It should also be appreciated that the fluid receiving device 30 may comprise one or more inlet valves 33 such as channel locks adapted to pause flow of the biological fluid 16 into of the fluid receiving device 30. Such inlet valves 33 may comprise valves, locks, or other structures which are adapted to block flow of the biological fluid 16 at certain times. For example, one or more inlet valves 33 of the fluid receiving device 30 may be engaged to pause flow of the biological fluid 16 into the fluid receiving device 30 while scanning is being performed by the scanner 70.

D. Scanning Techniques.

As described and shown herein, a wide range of scanning techniques May be utilized to scan a biological fluid 16 and identify any constituent biological elements thereof, such as but not limited to white blood cells, red blood cells, CTCs, platelets, host cells, cell-free plasma, pathogens, and the like. The types of biological fluids 16 that can be scanned include a wide range of biological fluids 16, such as but not limited to blood, lymphatic fluid, cerebrospinal fluid, sweat, urine, pericardial fluid, stools, saliva, and the like. In some embodiments, multiple types of biological fluids 16 may be scanned either together or in turn. For example, both blood and cerebrospinal fluids may be simultaneously or sequentially scanned by the same fluid receiving device 30.

Exemplary techniques for scanning may include Phase contrast microscopy (PCM), DIC Microscopy, Hoffman modulation, polarized light microscopy, digital holographic microscopy, confocal scanning optic microscopy (CSOM), or laser scanning optic microscopy (SOM) to measure voxel fluorescence, bright-field microscopy, dark-field illumination, Raman spectrometry to measure Raman Scattering, Optical interferometry to measure optical interference, total internal reflection fluorescence microscopy to measure evanescent effect, planar waveguides for refractive index detection, photonic crystal biosensors for measure of biomolecules on cell surfaces, and light property modulation detections such as surface plasmon resonance (SPR) detection.

With respect to digital holographic microscopy, digital holography is used to record a wave front diffracted from an object by a light source 72. Utilizing the interference of light from the light source 72, both amplitude and phase information of an object wave 77 may be recorded to produce a hologram containing the information of the object wave 77. A three-dimensional image May then be reconstructed from the hologram by the control unit 80.

In an embodiment utilizing digital holographic microscopy, the scanner 70 may include a light source 72 as previously discussed. The light source 72 may comprise various types of illuminating devices, such as but not limited to a laser such as a monochromatic laser. A pair of laser light waves is generated from the light source 72 by dividing the laser beam with a beam splitter 74 such that one of the split light waves illuminates the biological fluid 16. The light diffracted from the biological fluid 16 forms an object wave 77, which illuminates the scanner 70 and is collected by the microscope objective 73. The remaining laser light wave is directly detected by the microscope objective 73 of the scanner 70 to serve as a reference wave 78. The object and reference waves 77, 78 interfere with each other at the scanner 70 to form an interference fringe image which is scanned by an image sensor 76.

Continuing to reference digital holographic microscopy, the object and reference wave 77, 78 fronts may be joined by the beam splitter 74 such that the object and reference wave 77, 78 fronts interfere and create a hologram which is detected by an image sensor 76. The control unit 80 may then process the digital hologram, with the control unit 80 functioning as a digital lens to calculate a viewable image of the object wave 77 front utilizing a numerical reconstruction algorithm.

While a microscope objective 73 may be used to collect the object wave 77 front, it should be appreciated that the microscope objective 73 is only used to collect light waves and not to form an image. Thus, the microscope objective 73 may comprise a simple lens, or may be omitted entirely in some embodiments. The interference pattern (hologram) may thus be recorded in such embodiments by a digital image sensor 76.

Digital holographic microscopy may be utilized to observe living cells within the biological fluid 16. From the recorded interference pattern of such living cells, the intensity and phase shift across various points of the cells may be numerically computed by the control unit 80. The control unit 80 may thus measure the phase delay images of biological cells within the biological fluid 16 to provide quantitative information about the morphological properties (e.g., cellular dry mass, surface texture, shape, etc.) of individual cells within the biological fluid 16.

In an exemplary embodiment, the systems and methods described herein may utilize these quantitative indicators of morphological properties in an algorithm to distinguish between cell types within the biological fluid 16. By way of example and without limitation, the control unit 80 may be adapted to extract parameters such as cell thickness, cell area, cell volume, cell dry mass, the phase shift across the cell, surface roughness and texture, cell shape, elongation, convexity, luminance, circularity, solidity, and the like.

Figure 31:
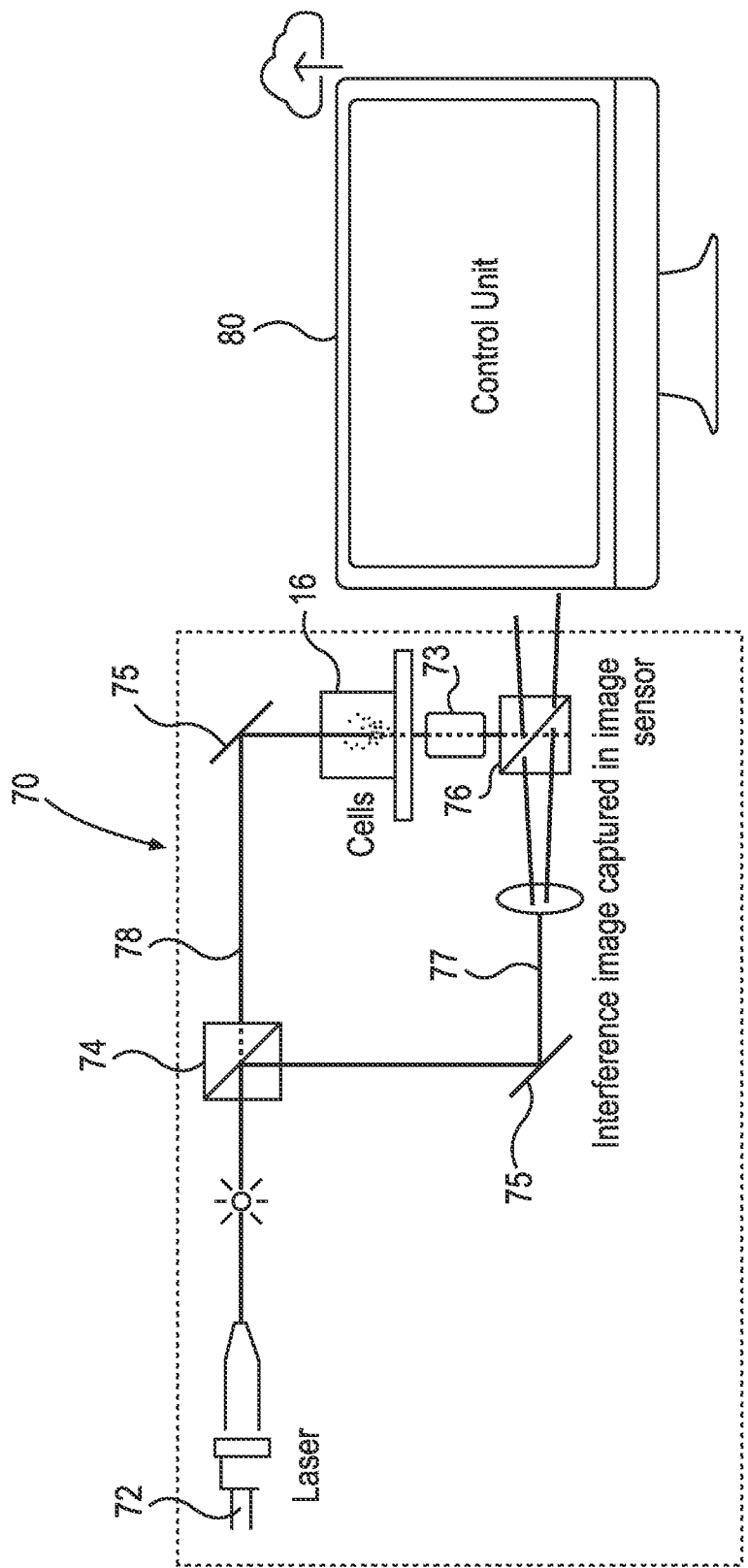
FIG. 31 is a block chart illustrating a scanner utilizing digital holographic microscopy of a biological fluid filtration system in accordance with an example embodiment.

Various types of digital holography may be utilized with the systems and methods described herein, including but not limited to off-axis Fresnel, Fourier, image plane, in-line, Gabor, and phase-shifting digital holography. FIG. 31 illustrates an off-axis embodiment. By utilizing digital holographic microscopy, the control unit 80 may differentiate between the various constituents 13 within a biological fluid 16 sample for further processing utilizing the systems and methods described herein.

It should be appreciated that multiple laser wavelengths may be utilized when scanning the biological fluid 16 with digital holographic microscopy. It has been shown that the refraction amount increases as the wavelength of light decreases. Thus, shorter wavelengths of light (e.g., violet and blue) are more slowed and consequently experience more bending than longer wavelengths of light (e.g., orange and red).

Since the morphological parameters in digital holographic microscopy are dependent upon the wavelength of the laser used, an exemplary embodiment of a scanning technique relying upon digital holographic microscopy may utilize multiple lasers each having different wavelengths. By way of example, the analysis may be initially conducted using a light source at a first wavelength. If the sample of cells requires additional confirmation, the light source may be switched to a different wavelength.

E. Ex Vivo Testing.

The systems and methods described herein may be utilized for ex vivo testing of various drugs and treatments on a patient 12 specific basis. While established tissue culture cell lines are often used for in vitro drug sensitivity assays, such cell lines are not truly representative of the cellular heterogeneity evidenced during metastasis and recurrence in specific patients 12. Thus, it is would be far more desirable to test such drugs and treatments on patient-derived CTCs and CTC-clusters.

Patient-derived CTCs and CTC-clusters offer greater precision in predicting outcomes for a particular patient 12, as they represent the heterogeneity profile for that particular patient 12 at that particular time. Critically, patient-derived CTCs and CTC-clusters may exhibit enhanced resistance to chemotherapy during stages of relapse.

Using the systems and methods described herein, sufficient CTCs and CTC-clusters may be extracted to permit both genomic and transcriptomic profiling. This allows for "direct-to-drug" ex vivo testing of treatments and drug agents to identify an optimal course of therapy for a particular patient 12 at any particular time during the progress of treatment.

Figure 34:
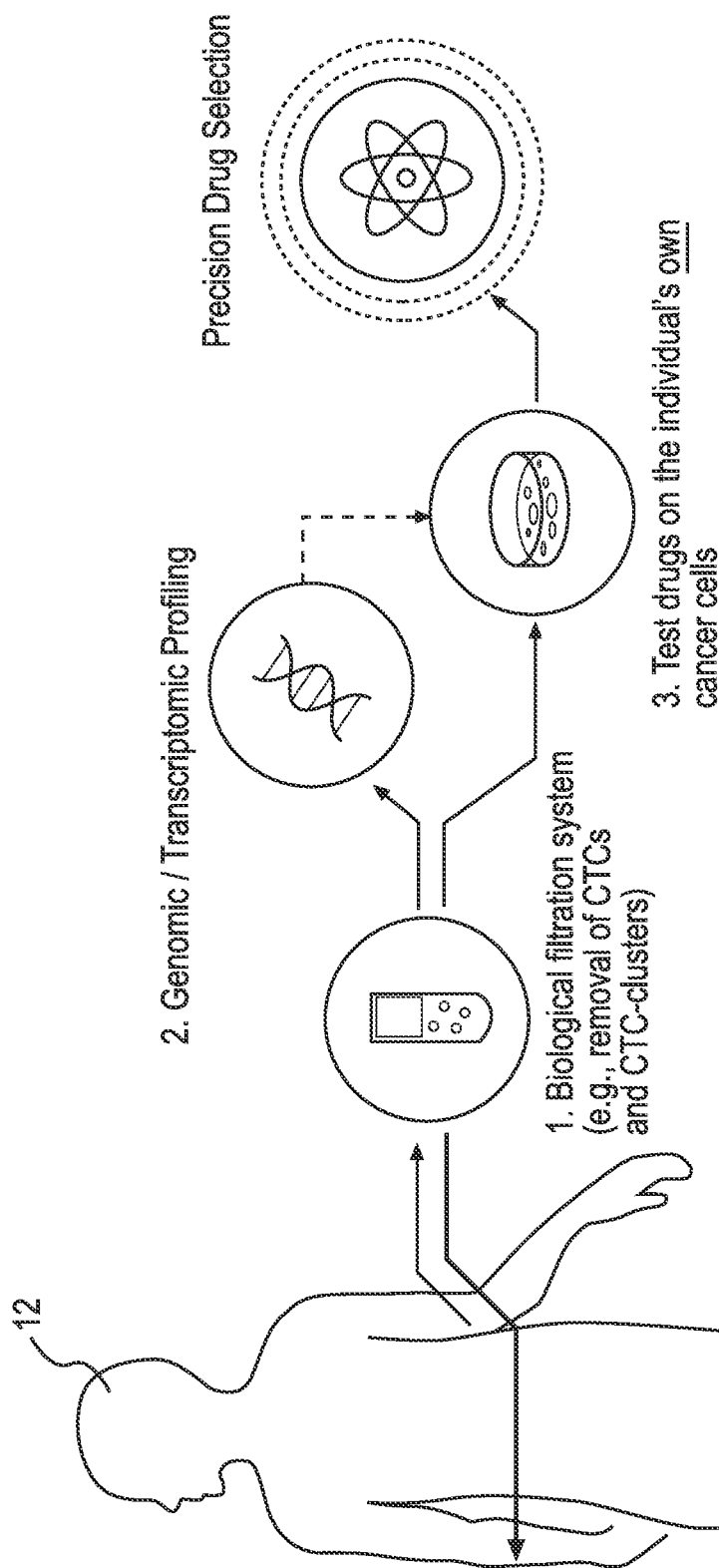
FIG. 34 is a block diagram illustrating a system and method of filtering a biological fluid for use in connection with testing of drugs and treatments in accordance with an example embodiment.

FIG. 34 illustrates an exemplary embodiment in which a portion of CTCs which have been identified and separated by the systems and methods described herein may be profiled for heterogeneity. As can be seen, CTCs and CTC-clusters may undergo genomic and transcriptomic profiling to determine potentially relevant drugs or treatments. After identifying potential drugs or treatments based upon the isolated CTCs and CTC-clusters from a particular patient 12, relevant drug targets may be identified. The drugs or treatments may then be tested on that particular patient's cancer cells ex vivo to identify optimal pathways.

In this manner, drugs and treatments may be optimized for each patient 12 based upon the cancer cells identified and separated by the methods and systems described herein to allow for precision drug selection that is unique to each patient 12 in consideration of the cancer cells unique to that patient 12 and in consideration of the course of treatment to that point for that patient 12.

F. Multi-Stage Separation.

Figure 35:
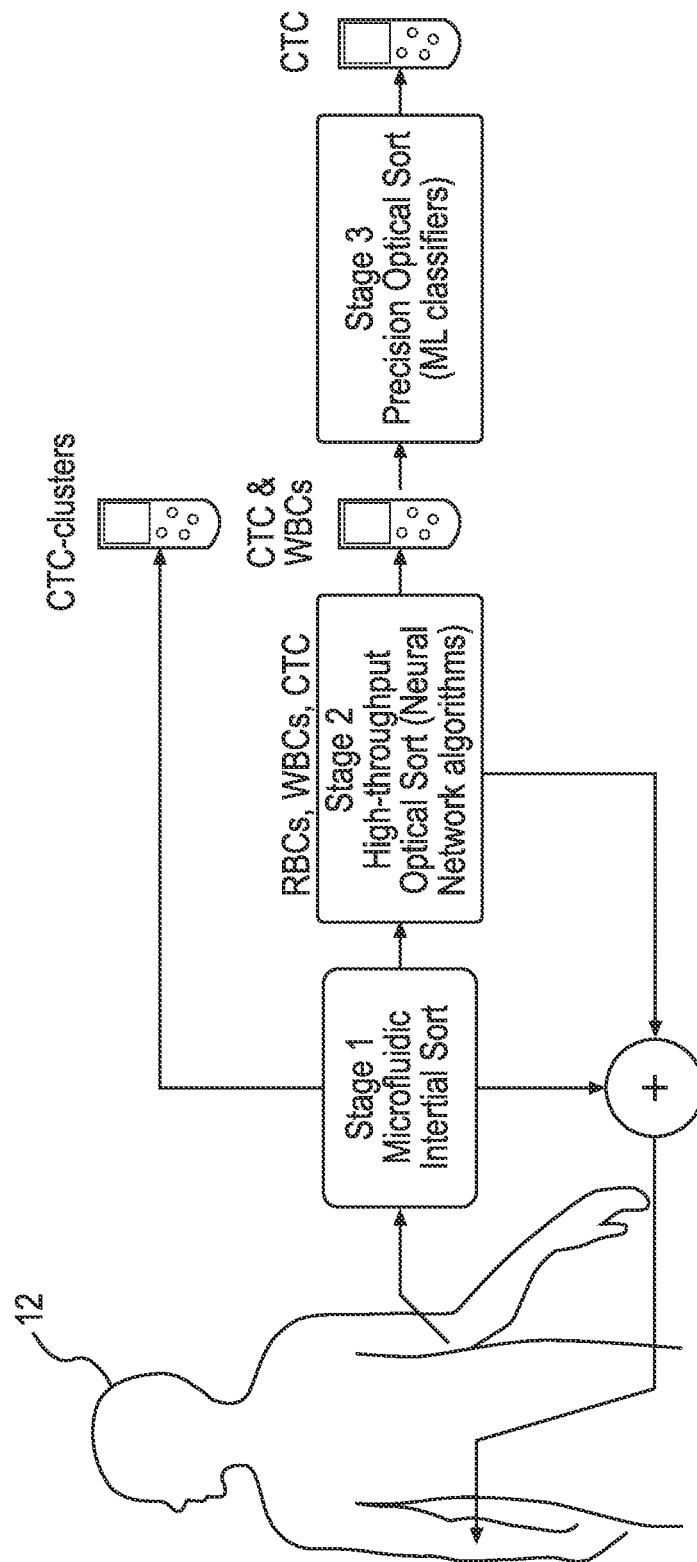
FIG. 35 is a flowchart illustrating a multi-stage system and method of filtering a biological fluid in accordance with an example embodiment.

As previously discussed, the systems and methods described herein may be utilized for multi-stage separation of non-healthy or malignant cells from healthy cells. FIG. 35 illustrates an exemplary embodiment of such a multi-stage separation system in which multiple stages are utilized to separate CTCs and CTC-clusters from a biological fluid 16. FIG. 36B illustrates another exemplary embodiment in which an isolation path 50 is split into additional channels for repeated, additional enrichment through scanning.

As shown in FIG. 35, the first stage of the multi-stage separation methodology involves receiving a biological fluid 16 from the patient 12. The biological fluid 16 may enter the multi-stage separation directly from the patient 12. At the first stage, passive inertial sorting, with or without the use of buffer fluids, may be utilized to separate red blood cells and CTC-clusters from the biological fluid 16. Red blood cells separated at this first stage may be returned to the biological fluid source 17 and CTC-clusters may be isolated for further processing.

Continuing to reference FIG. 35, CTC-clusters and red blood cells are separated from the biological fluid 16 in the first stage by inertial sorting. The remaining cells, which will generally include additional red blood cells, white blood cells, and CTCs, will then be passed onto the second stage. Such remaining cells may be passed onto a fluid receiving device 30 for a high-throughput optical sort utilizing neural network algorithms. The second stage will thus be utilized to further separate the cells of the biological fluid 16. Any separated red and white blood cells may then be returned to the patient 12, with identified CTCs and any remaining white blood cells being passed on to a third stage.

As shown in FIG. 35, the third stage may comprise precision optical sorting through use of an additional fluid receiving device 30 that is in series with the fluid receiving device 30 of the second stage. Interpretable machine learning classifiers may be utilized to separate the remaining white blood cells, thus leaving only CTCs which are separated at the third stage. In this manner, CTC-clusters and CTCs May be individually separated from a biological fluid 16, with white and red blood cells from the biological fluid 16 being returned to the patient 12. The individually separated CTC-clusters and CTCs may then be retained for further processing, such as ex vivo testing, therapeutics, or diagnostics. Additional stages may also be added as-needed for further enrichment.

G. Optical Filtration of Subsets of Healthy Cells.

The methods and systems described herein may be utilized to filter specific subsets of healthy cells (e.g., T-cells) from other types of cells. In such an embodiment, the library of desirable constituents 15 (e.g., healthy cells) may be configured to exclude specific subsets of healthy cells (e.g., T-cells) so as to allow the biological fluid filtration system 10 to filter such subtypes of healthy cells. As previously indicated, such methods may be applied for human or veterinary uses. The biological fluid 16 may be scanned for subsets of healthy cells utilizing fluid receiving devices 30 such as but not limited to microfluidic channels 31, microwell arrays 32, and droplet generators 34.

In the course of some therapies and treatments, such as Chimeric antigen receptor (CAR) T-cell therapy, T-cells engineered with chimeric antigen receptors may be utilized for cancer therapy. As is known in the art, T-cells are a type of white blood cell which develops in the thymus gland and play a central role in the body's immune response. CAR-T immunotherapy is utilized to modify T-cells to recognize cancer cells in order to more effectively target and destroy them.

T-cells are harvested, genetically altered, and then the resulting CAR-T cells are infused into the patient 12 to attack cancer cells. Such CAR-T cells may be derived from T-cells in the patient's 12 own blood (autologous) or derived from the T-cells of another healthy donor (allogenic). Once isolated, these T-cells are genetically engineered to express a specific CAR, which programs the T-cells to target an antigen that is present on the surface of tumors. In other therapies, other forms of white blood cells (such as natural killer or "NK" cells) are similarly engineered to fight cancers.

In an exemplary embodiment of a biological fluid filtration system 10 for filtration of subsets of healthy cells, the biological fluid source 17 may be an aphaeretic extract from a therapeutic apheresis or leukapheresis machine containing white blood cells including T-cells. The systems and methods described herein may be utilized to extract just the T-cells by recognizing all healthy cells except for the T-cells, and then filtering out the undesirable cells (the T-cells). As a further example, other types of healthy cells may be omitted from recognition, such as NK cells, so that those healthy cells may be filtered out in a similar manner.

Figure 37:
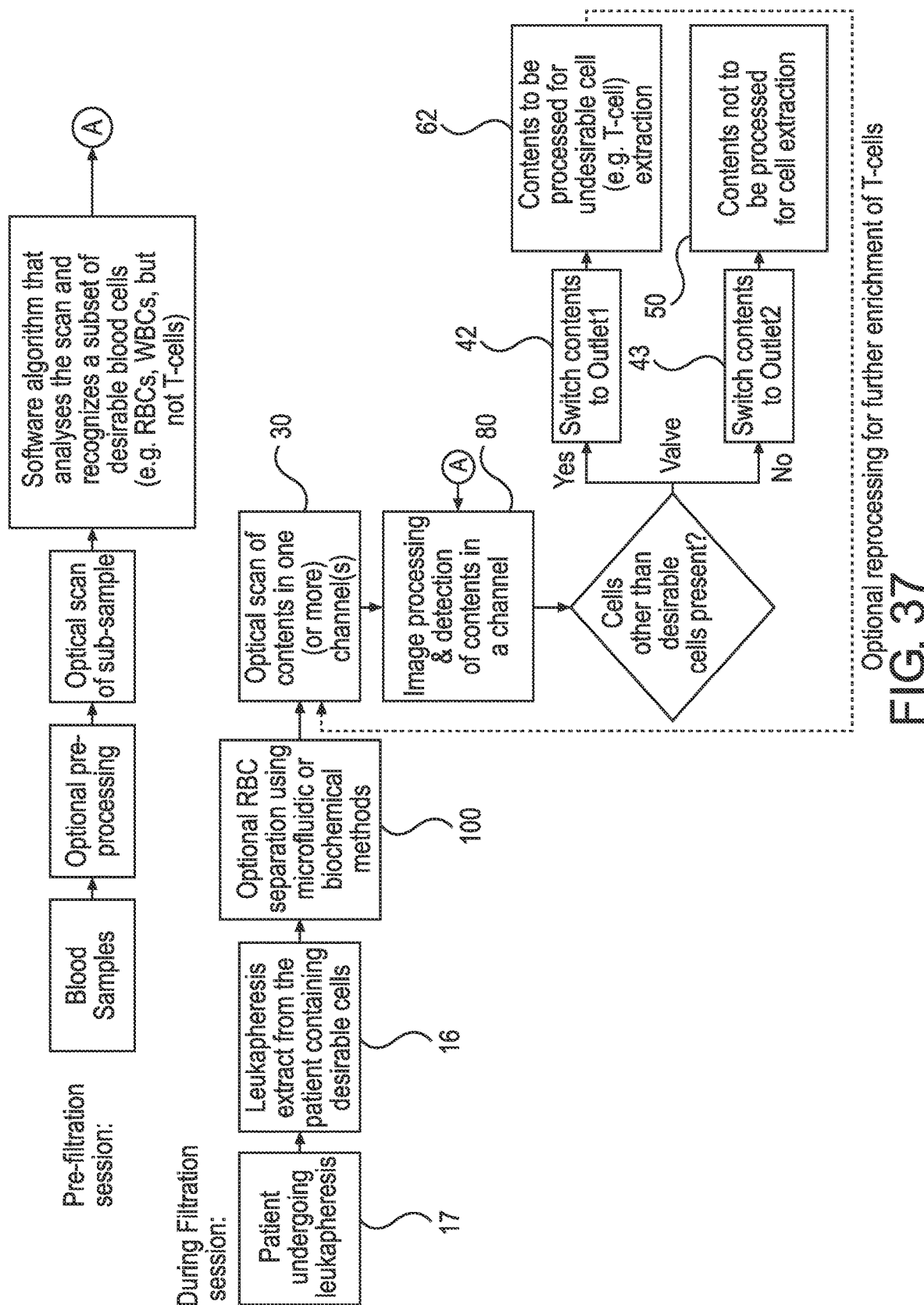
FIG. 37 is a flowchart illustrating a system and method of filtering a biological fluid for use in connection with filtration of subsets of healthy cells in accordance with an example embodiment.

FIG. 37 illustrates an exemplary method of filtering out T-cells from a biological fluid 16 containing other types of healthy cells. It should be appreciated that the biological fluid source 17 may be human or veterinary and may include such biological fluids 16 as blood, lymphatic fluid, cerebrospinal fluid, sweat, urine, pericardial fluid, stools, and saliva.

As shown in FIG. 37, an optional pre-filtration session may be conducted to create a reference data 91 in which a sample of biological fluid 16, from the patient 12 or others, is pre-processed by optically scanning the sample with a scanner 70 and recognizing certain biological fluid constituents 13 such as certain types of cells within the biological fluid 16 using an algorithm run by a control unit 80. The optical scan of the subsample allows for a software algorithm run by the control unit 80 to analyze the scanned data from the subsample and recognize any subsets of healthy blood cells (e.g., red blood cells, white blood cells) while not recognizing certain subsets of healthy blood cells (e.g. T-cells). Such pre-processing may be utilized to create a control group for recognizing different types of cells during the processing phase.

Continuing to reference FIG. 37, it can be seen that in an exemplary embodiment a patient 12 may undergo leukapheresis. The leukapheresis extract from the patient containing healthy cells is channeled through a fluid receiving device 30 such as microfluidic channels, microwell arrays, or droplet generators and the extract is scanned by the scanner 70. The control unit 80 then performs image processing and detection of the contents within the fluid receiving device 30, including use of any pre-processing findings if pre-processing had previously occurred.

The control unit 80 will analyze the results of the scan from the scanner 70 to determine where to route the biological fluid 16. If cells other than recognized healthy cells are present, the biological fluid 16 may be routed along a reprocessing path 62 for the contents to be processed for extraction of any undesirable cells (e.g., T-cells). If only recognized healthy cells are present, the contents may be routed along an isolation path 50 to be discarded or retained for further use without cell extraction.

H. Presorting of Biological Fluids.

Figure 38:
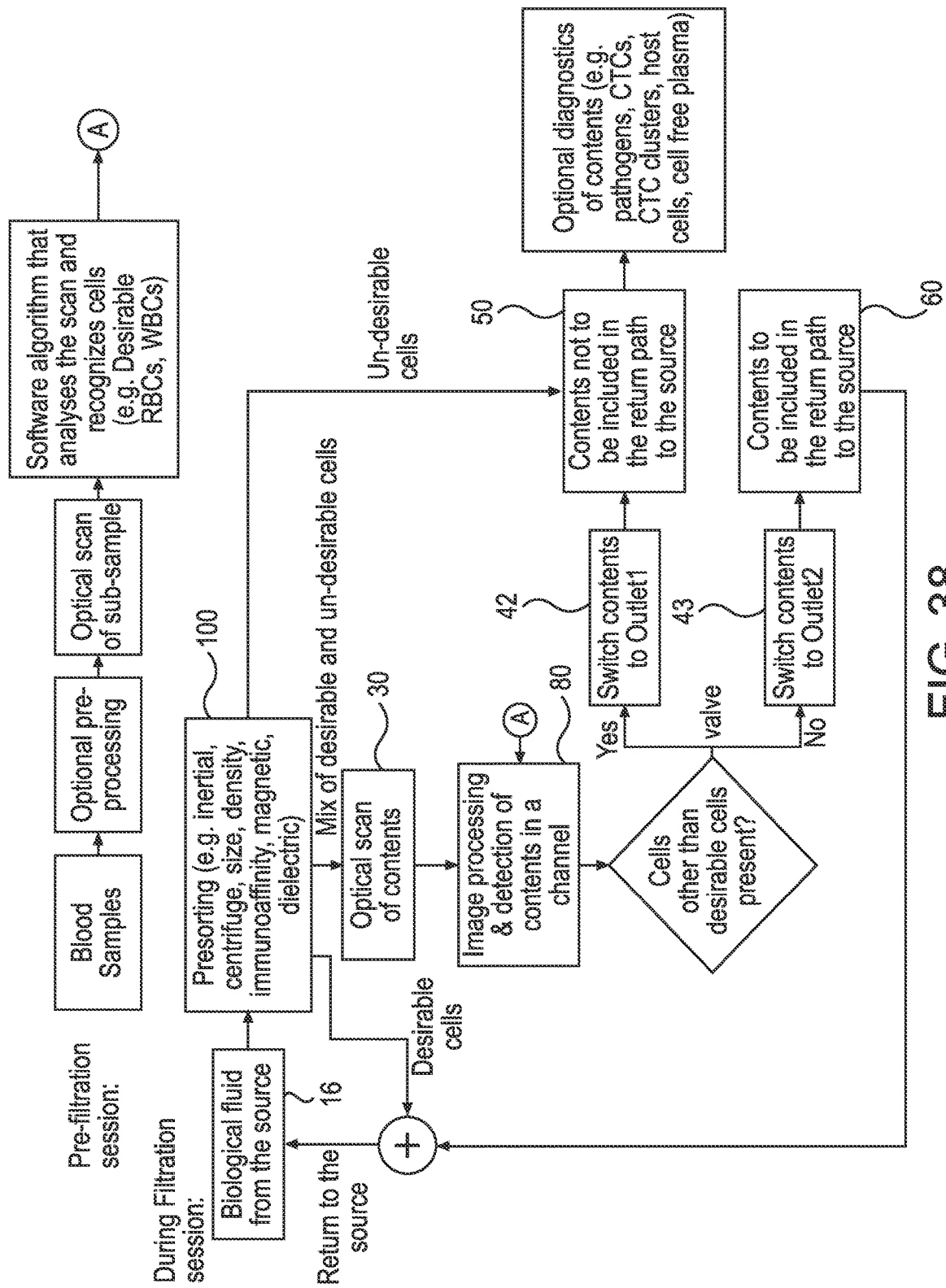
FIG. 38 is a flowchart illustrating a system and method of filtering a biological fluid utilizing a presorting stage in accordance with an example embodiment.

FIG. 38 illustrates an exemplary method of presorting and then optically filtering a portion of a biological fluid 16 of biological fluid constituents 13 such as pathogens or CTCs. As shown in FIG. 38, an optional pre-filtration session may be conducted to create a reference data 91 in which a sample of biological fluid 16, from the patient 12 or others, is pre-processed by optically scanning the sample with a scanner 70 and recognizing the biological fluid constituents 13 such as cells within the biological fluid 16 using an algorithm run by a control unit 80.

Continuing to reference FIG. 38, it can be seen that biological fluid 16 is first drawn from the biological fluid source 17 during a filtration session. The biological fluid 16 may comprise various fluids as discussed herein, such as but not limited to blood, lymphatic fluid, CSF, sweat, urine, pericardial fluid, stools, and saliva. The biological fluid source 17 may comprise a human or an animal. After the biological fluid 16 is drawn from the biological fluid source 17, the biological fluid 16 may be presorted, such as by using a microfluidic separation module 100.

The presorting of the biological fluid 16 may be utilized to separate desirable constituents 15 from the biological fluid 16 prior to further processing. The manner of presorting utilized by the microfluidic separate module 100 may vary in different embodiments, and may include without limitation the use of inertial sorting, centrifugal sorting, microfluidic sorting, and the like. Characteristics utilized during presorting may include size, density, inertial hydrodynamic, antigen binding affinity, motility, centrifugation, electrical charge, electric dipole moment, or magnetism.

The presorting of the biological fluid 16 by the microfluidic sorting module 100 allows for the initial separation of biological fluid constituents 13 without optical scanning. Any such biological fluid constituents 13, such as CTC, may be immediately routed along a return path 60 back to the biological fluid source 17, or may be sequestered along an isolation path 50 for further processing. After the presorting step is completed, a mixture of undesirable constituents 14 and desirable constituents 15 may then be transferred to a fluid receiving device 30 for further processing.

Continuing to reference FIG. 38, it can be seen the mixture of undesirable constituents 14 and desirable constituents 15 is optically scanned on the fluid receiving device 30 by a scanner 70. The control unit 80 then performs image processing and detection to identify the contents and differentiate between undesirable constituents 14 and desirable constituents 15. If undesirable constituents 14 are detected in the sample, the sample is not returned to the biological fluid source 17, but may instead be sent along an isolation path 50 for sequestration and optional diagnostics of the contents to identify pathogens, CTC, CTC-clusters, host cells, cell free plasma, and the like.

Any samples comprising only undesirable constituents 14 after the presorting stage may be immediately directed along an isolation path 50 and not returned to the biological fluid source 17. Such samples may be sequestered along the isolation path 50 for optional diagnostics and/or therapeutics as discussed herein.

Figure 39:
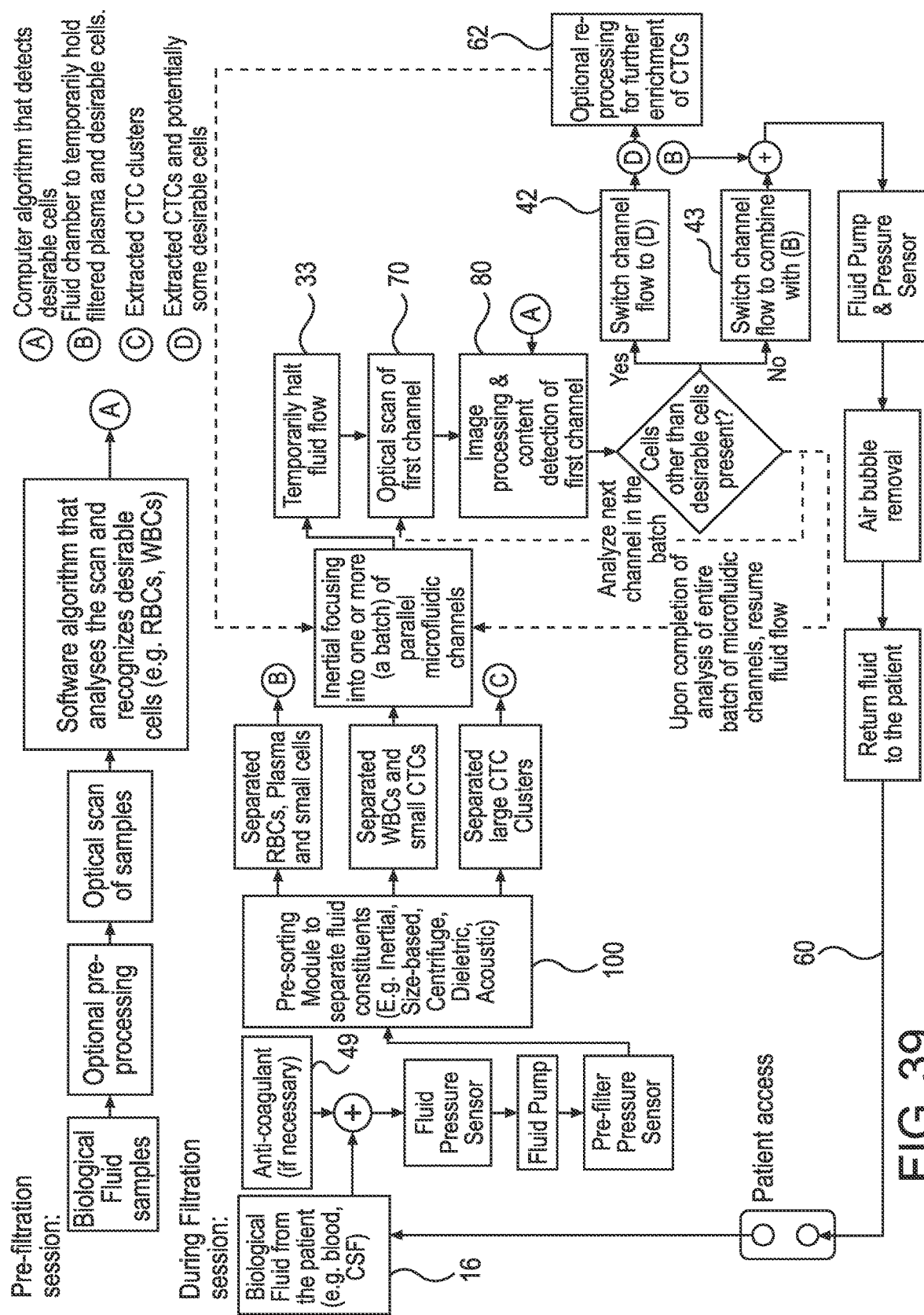
FIG. 39 is a flowchart illustrating a system and method of filtering a biological fluid utilizing a presorting stage and having multiple outlet ports in accordance with an example embodiment.

FIG. 39 illustrates another exemplary method of presorting and then optically filtering a portion of a biological fluid 16 which, by utilizing multiple outlet ports, may be utilized to sequester and separately hold isolated biological fluid constituents 13 such as CTCs, CTC-clusters, white blood cells, cell-free plasma, and the like. The sequestered outputs may then be reprocessed single or multiple times using the systems and methods described herein, without the aphaeretic components, to further enrich the isolation of such biological fluid constituents 13.

As shown in FIG. 39, an optional pre-filtration session may be conducted to create a reference data 91 in which a sample of biological fluid 16, from the patient 12 or others, is pre-processed by optically scanning the sample with a scanner 70 and recognizing the biological fluid constituents 13 such as cells within the biological fluid 16 using an algorithm run by a control unit 80. Biological fluid 16 is first drawn from the patient 12. If necessary, an anti-coagulant may be applied to the biological fluid. A fluid pump may draw the biological fluid 16 through a fluid pressure sensor and pre-filter pressure sensor prior to entering a pre-sorting module. The pre-sorting module utilizes the techniques and/or characteristics described herein, such as but not limited to inertial, size-based, centrifugal, dielectric, and/or acoustic to separate biological fluid constituents 13 from the biological fluid 16. In some embodiments, the use of additional buffers or dilution liquids or reagents may be employed in the pre-sorting module. In such examples, the embodiment might include ports and reservoirs to insert, collect, and/or replenish such fluids.

A first set of biological fluid constituents 13, such as red blood cells, plasma, and small cells, may be transferred to a fluid chamber to temporarily hold filtered plasma and healthy cells. Separated large CTC-clusters may be retained and sequestered for further processing such as diagnostics. Separated white blood cells and small CTCs may be transferred into one or more fluid receiving devices 30 such as microfluidic channels 31 arranged in parallel. Each fluid receiving device 30 is independently scanned, and its contents then undergo image processing and content detection by the control unit 80, which may utilize findings from any optional pre-filtration session.

If undesirable constituents 14 such as cells other than healthy cells are detected, the contents may be re-routed back to the fluid receiving devices 30 by a reprocessing path 62 for further enrichment of CTCs. If no cells other than healthy cells are detected, the contents may be combined with the filtered plasma and healthy cells, pass through a fluid pump and pressure sensor, undergo air bubble removal, and returned to the biological fluid source 17 by the return path 60.

Figure 40:
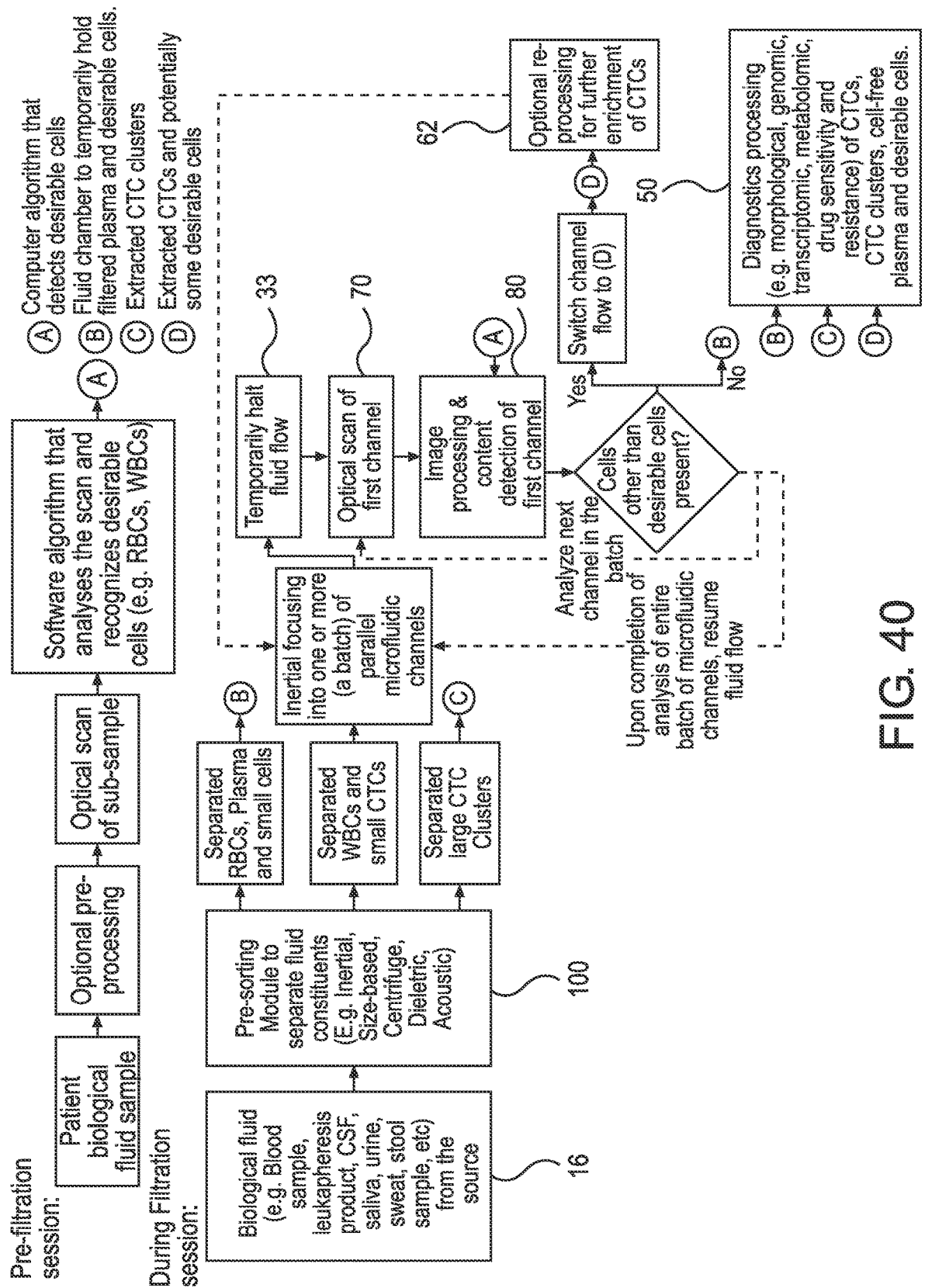
FIG. 40 is a flowchart illustrating a system and method of filtering a biological fluid utilizing a presorting stage for diagnostics in accordance with an example embodiment.

FIG. 40 illustrates yet another method of presorting and then optically filtering a portion of a biological fluid 16. Such embodiments may include the use of diagnostic systems to separate pathogens or CTCs from biological fluid 16 samples for downstream diagnostic (e.g., genomic, transcriptomic, metabolomics, drug sensitive, drug resistance, etc.) characterization. FIG. 40 illustrates such a diagnostic embodiment without a return path 60 back to the biological fluid source 17.

As shown in FIG. 40, an optional pre-filtration session may be conducted to create a reference data 91 in which a sample of biological fluid 16, from the patient 12 or others, is pre-processed by optically scanning the sample with a scanner 70 and recognizing the biological fluid constituents 13 such as cells within the biological fluid 16 using an algorithm run by a control unit 80. At the filtration session, biological fluid 16 is drawn from the source and entered into a pre-sorting module to separate biological fluid constituents 13 (e.g., inertial, size-based, centrifuge, dielectric, acoustic, etc.). Any separated red blood cells, plasma, and small cells are transferred to a fluid chamber to hold plasma and healthy cells. Any separated large CTC-clusters may be sequestered for further processing.

Samples including separated white blood cells and small CTCs may be transferred by inertial focusing into one or more parallel fluid receiving devices 30. Fluid flow is temporarily halted, and each fluid receiving device 30 is scanned by a scanner 70. The control unit 80 conducts image processing and content detection of each such sample in-turn.

If cells other than healthy cells are present, such as extracted CTCs along with potentially some healthy cells, the sample may be rerouted back to the fluid receiving devices 30 by a reprocessing path 62 for further enrichment of CTCs. Enriched contents may be routed along an isolation path 50 for diagnostic processing (e.g., genomic, transcriptomic, metabolomics, drug sensitivity, drug resistance, etc.) along with any previously-separated red blood cells, plasma, small cells, and separated large CTC-clusters.

Figure 41:
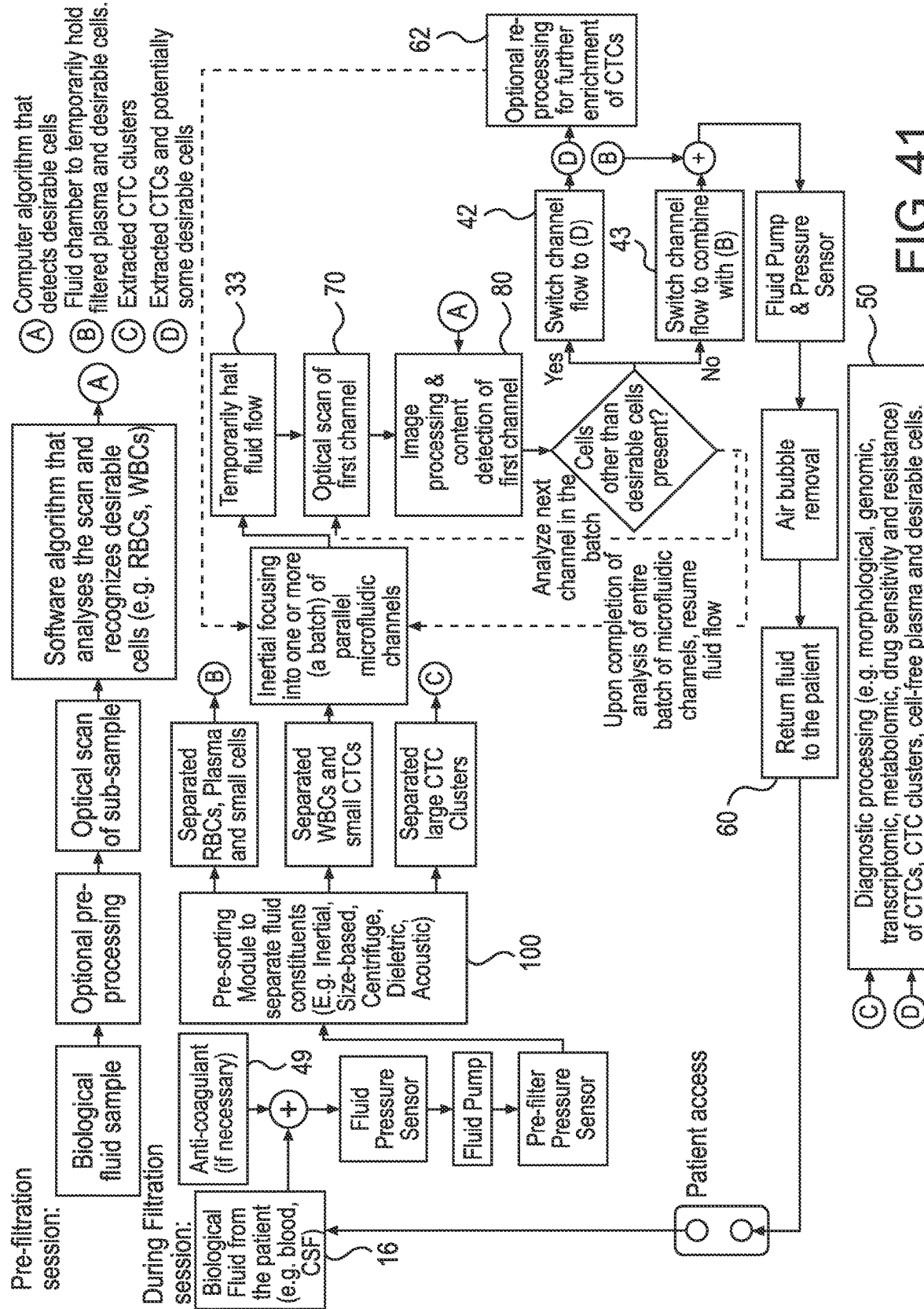
FIG. 41 is a flowchart illustrating a system and method of filtering a biological fluid utilizing a presorting stage for diagnostics with healthy cells being returned in accordance with an example embodiment.

FIG. 41 illustrates another embodiment of a method of presorting and then optically filtering a portion of a biological fluid 16, with healthy cells being returned back to the biological fluid source 17. An optional pre-filtration session may be conducted to create a reference data 91 in which a sample of biological fluid 16, from the patient 12 or others, is pre-processed by optically scanning the sample with a scanner 70 and recognizing the biological fluid constituents 13 such as cells within the biological fluid 16 using an algorithm run by a control unit 80.

During the filtration session, biological fluid 16 is drawn from the biological fluid source 17. Anti-coagulants may be applied if necessary to prevent clotting within the system. The biological fluid 16 is then pumped by a fluid pump past a fluid pressure sensor and a pre-filter pressure sensor. The biological fluid 16 then enters the pre-sorting module to separate biological fluid constituents 13 in any of the manners previously discussed. As with previous embodiments, healthy cells such as separated red blood cells, plasma, and small cells may be transferred to a fluid chamber to be temporarily held. Malignant cells such as separated large CTC-clusters may be transferred along an isolation path 50 to be sequestered for diagnostic processing.

Samples with both healthy and malignant cells, such as separated white blood cells and small CTCs, may be inertial focused into one or more parallel fluid receiving devices 30 such as microfluidic channels 31. Once within the one or more fluid receiving devices 30, such samples will be held in the fluid receiving device 30 as optical scans are performed by one or more scanners 70. In an embodiment in which multiple scanners 70 are utilized, each of the samples May be scanned simultaneously. In an embodiment in which a single scanner 70 is utilized, each of the samples may be held in place while each sample is sequentially scanned.

It should also be appreciated, with this embodiment and with the others described herein, that a single fluid receiving device 30 may be utilized to scan multiple distinct samples at different times. In such embodiments, a first sample will be transferred to the fluid receiving device 30, scanned, and the results will be transferred to the control unit 80. Upon completion of analysis of that sample, fluid flow may be resumed to transfer another sample onto the fluid receiving device 30 for scanning. These steps may be repeated until all of the samples have been scanned.

The results of each optical scan (e.g., images or other cell characteristics) are transferred to the control unit 80 for image processing and content detection. This step may be repeated until all of the samples with both healthy and malignant cells have been scanned and processed as described above. If healthy cells are detected among unhealthy cells (e.g., CTCs), the sample may be returned to the fluid receiving device 30 along a reprocessing path 62 for further scanning and processing. Alternatively or after multiple such scans and enrichment, the sample may be sequestered for diagnostic processing using any of the methods previously discussed herein.

If only healthy cells are detected in a sample (e.g., only white blood cells and no CTCs), the sample may be transferred via a fluid pump and pressure sensor back to the patient 12 or biological fluid source 17 along a return path 60. In some embodiments, any filtered plasma and healthy cells in the fluid chamber May similarly be returned to the biological fluid source 17, either with the white blood cells or separately. Air bubbles will also be removed prior to return to the biological fluid source 17. In this manner, the embodiment shown in FIG. 41 allows for only confirmed healthy cells to be returned to the patient 12, with any other cells (e.g., malignant cells or undesirable cells) being sequestered for disposal or for diagnostic processing.

Figure 42:
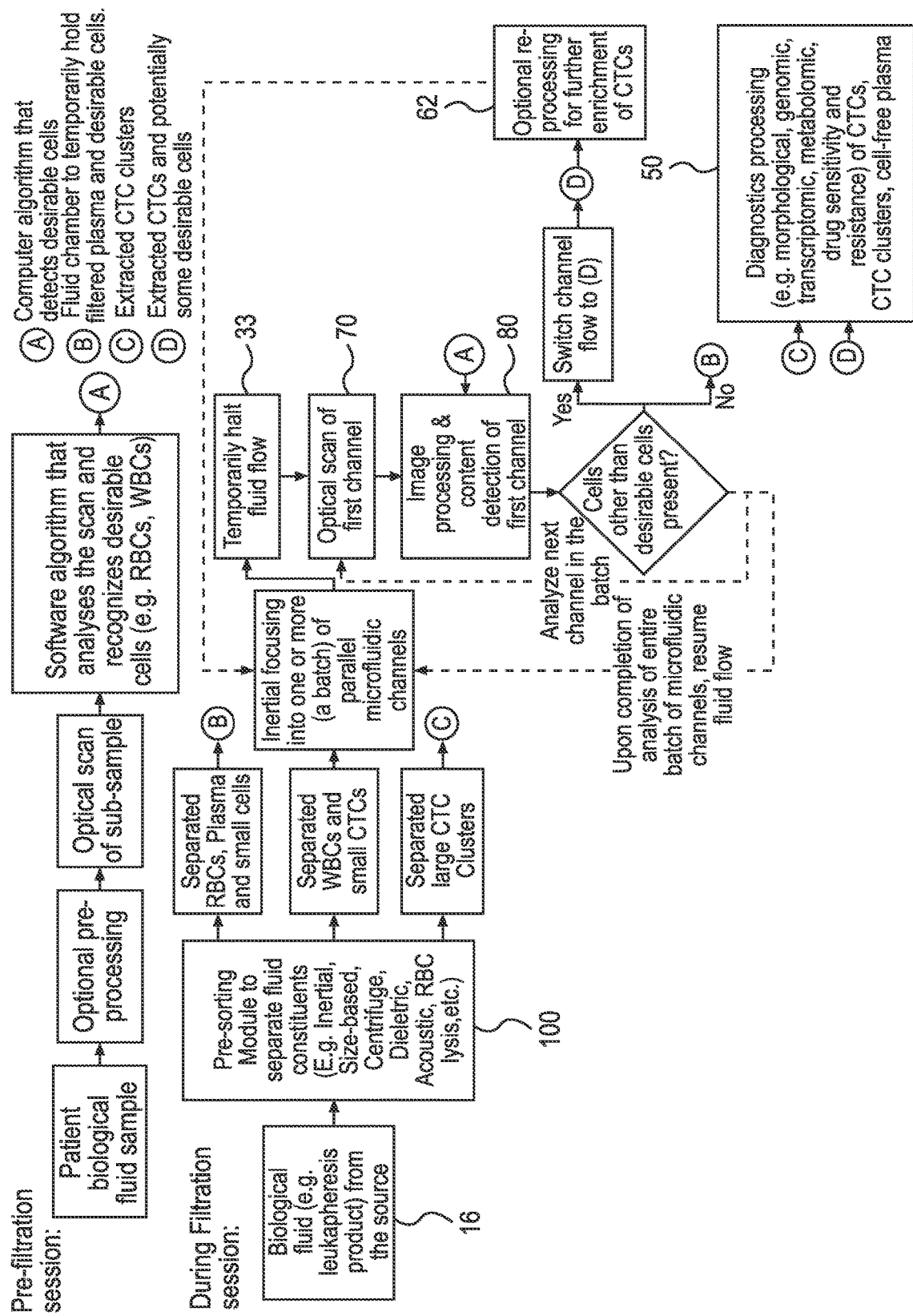
FIG. 42 is a flowchart illustrating a system and method of filtering a biological fluid utilizing a presorting stage for diagnostics with healthy cells being returned in accordance with an example embodiment.

In another exemplary embodiment such as shown in FIG. 42, non-aphaeretic methods may be utilized for the removal of tumor cell contaminants from autologous stem-cell transplant products. Autologous stem cell transplants are generally used in patients 12 who need to undergo high doses of chemotherapy and radiation to cure their disease. These treatments can be toxic and thus damage the bone marrow. An autologous stem cell transplant helps to replace the damaged bone marrow, but it is often reported that the process to collect stem cells from the patient may lead to contamination of such products with tumor cells. Using the method shown in FIG. 42, the biological fluid filtration system 10 may be used to prevent or remove such contamination of stem cells.

As shown in FIG. 42, a pre-filtration session may be conducted to recognize healthy cells. During the filtration session, biological fluid 16 such as leukapheresis product from the biological fluid source 17 is transferred to a presorting module to separate fluid constituents by any of the methods described herein. As with the other embodiments, the pre-sorting may separate healthy cells such as red blood cells, plasma, and small cells which are transferred to a fluid chamber for transplantation. Malignant cells such as large CTC-clusters may be sequestered for diagnostic processing using any of the methods previously described.

With respect to the remaining samples containing both healthy and malignant or undesirable cells, inertial focusing may be utilized to transfer such samples onto one or more fluid receiving devices 30. Each sample is then scanned (either simultaneously using multiple fluid receiving devices 30 in parallel or sequentially using a single fluid receiving device 30 or multiple fluid receiving devices 30 in series) and the results transferred to the control unit 80 for image processing and content detection.

If cells other than healthy cells are detected, such samples may be rerouted back to the fluid receiving device 30 along a reprocessing path 62 for further processing or may be sequestered for diagnostic processing along an isolation path 50 using any of the methods described herein. If only healthy cells are detected, such samples may be transferred to the fluid chamber with the healthy cells from the presorting to be transplanted back to the patient 12.

Figure 43:
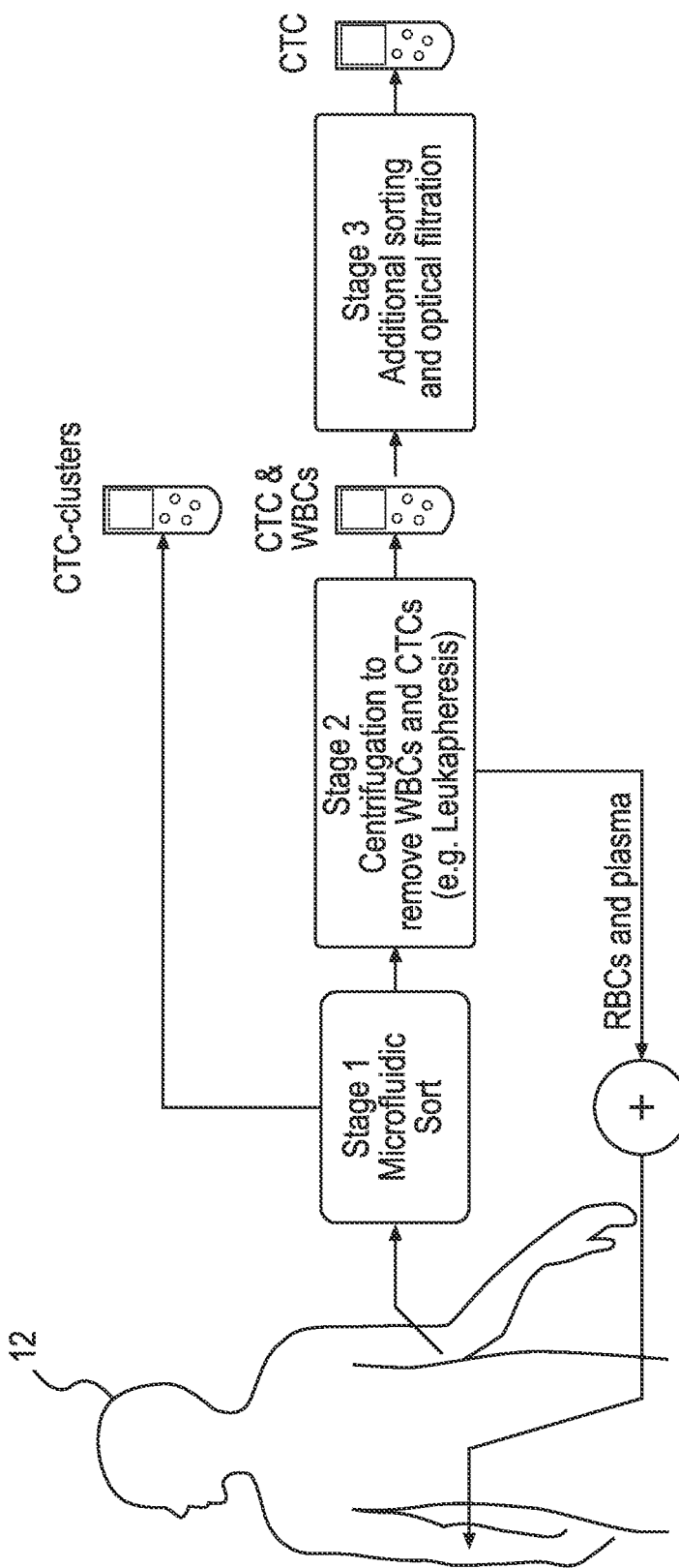
FIG. 43 is a block diagram illustrating a system and method of filtering a biological fluid utilizing multiple pre-sorting stages in accordance with an example embodiment.

FIG. 43 illustrates an embodiment in which multiple pre-sorting techniques are utilized in conjunction with optical filtration in a biological fluid filtration system 10. Biological fluids 16 are drawn from a biological fluid source 17 such as an animal or human. A passive inertial sort may be utilized to separate any CTC-clusters which may be sequestered for disposal or diagnostics. After the initial inertial sort, centrifugation may be utilized to remove white blood cells and CTCs (e.g., leukapheresis).

During leukapheresis, some red blood cells and plasma may be returned to the patient 12. The leukapheresis product containing white blood cells and CTCs may be transferred to a third stage for optical filtration using the methods described herein to separate the CTCs for diagnostic processing. Thus, the biological fluid 16 is pre-filtered across multiple stages prior to optical filtration. As a further example, blood could first be filtered using microfluidic inertial mechanisms to sort out large CTC-clusters. The remainder undergoes therapeutic apheresis to separate white blood cells and CTCs. That mix of cells is then filtered using the optical filtration techniques discussed herein.

I. Body-Worn Aphaeretic Optical Filtration Device.

While the various embodiments previously discussed are typically conducted in clinical or lab settings, certain embodiments may allow for the systems and methods described herein to be utilized in a body-worn configuration outside of a clinical or lab setting.

Figure 44A:
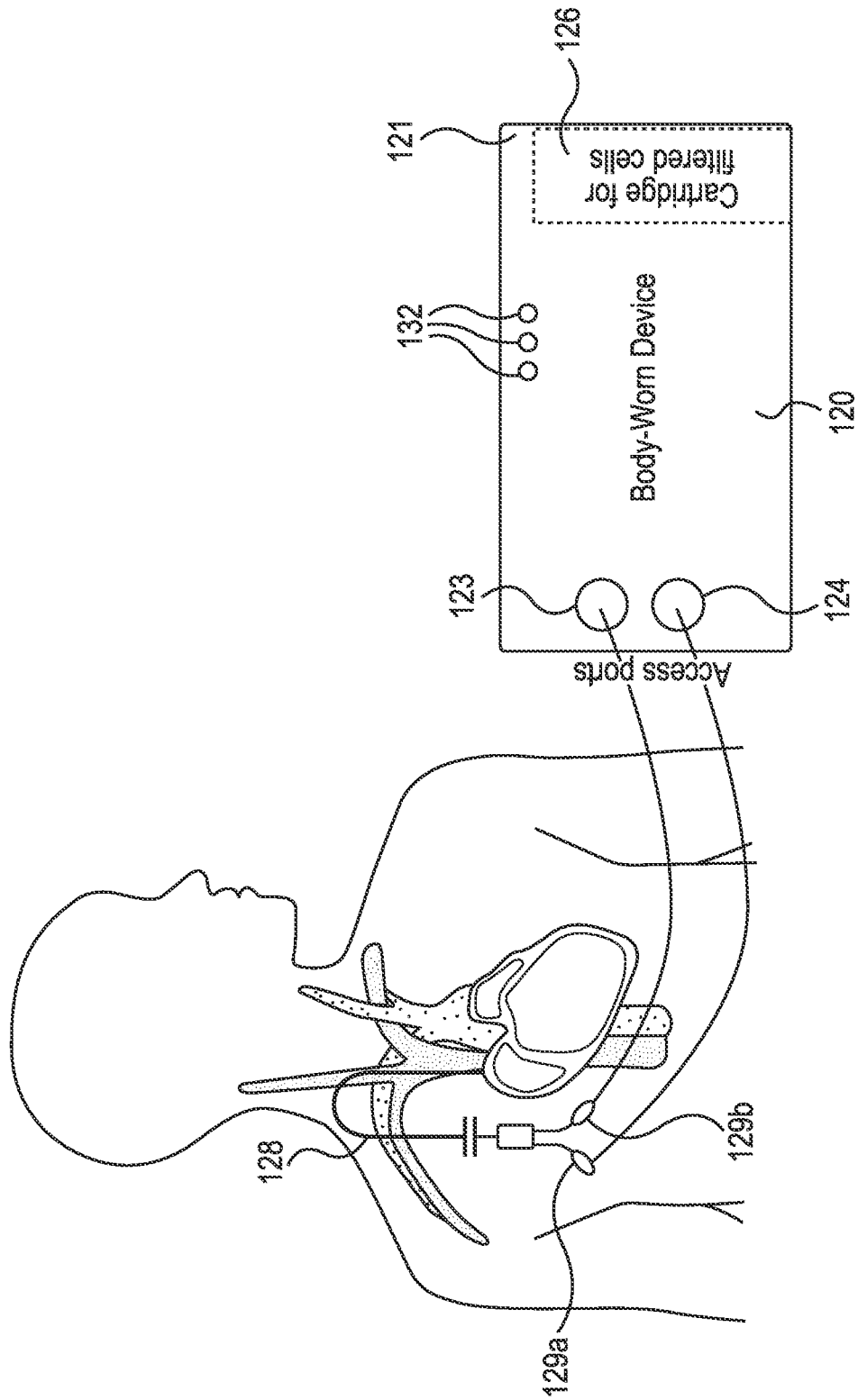
FIG. 44A is a block diagram illustrating a body-worn device of a biological fluid filtration system worn on a patient in accordance with an example embodiment.
Figure 44B:
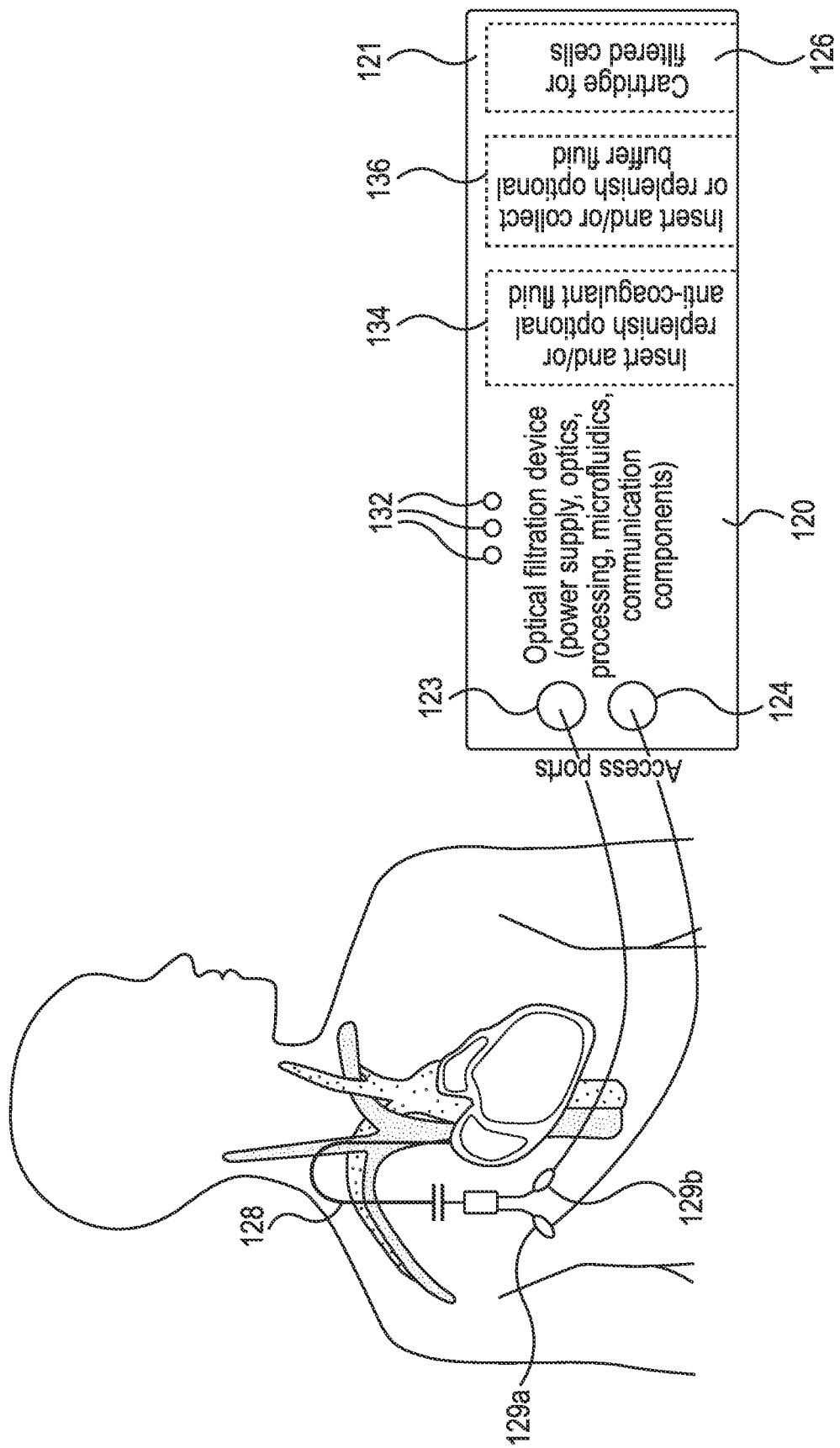
FIG. 44B is a block diagram illustrating a body-worn device of a biological fluid filtration system including anti-coagulant and buffer fluid worn on a patient in accordance with an example embodiment.
Figure 45:
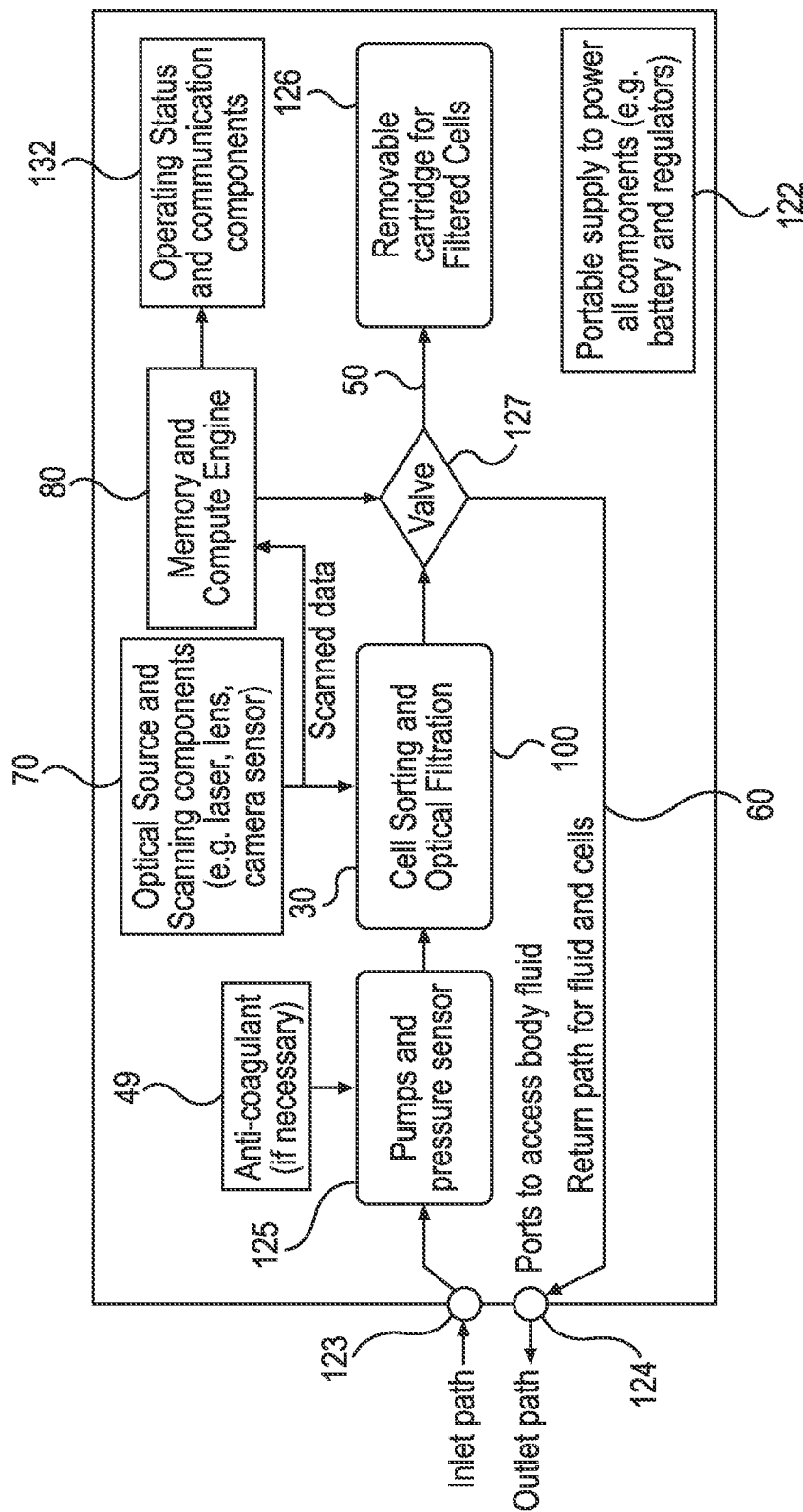
FIG. 45 is a block diagram illustrating a body-worn device of a biological fluid filtration system in accordance with an example embodiment.

FIGS. 44A, 44B, and 45 illustrate an exemplary embodiment of such a body-worn device 120. The body-worn device 120 may utilize optical components, including one or more fluid receiving devices 30 and one or more scanners 70, to filter undesirable constituents 14 from various biological fluids 16, such as blood, lymphatic fluid, cerebrospinal fluid, sweat, urine, pericardial fluid, stools, and saliva. The biological fluid source 17 may be veterinary or human.

The body-worn device 120 will generally comprise a housing 121 which houses all of the power, optical, microfluidic, computational, and communication components necessary for the patient 12 utilizing the body-worn device 120 to freely move about. The body-worn device 120 will generally include a power source 122 for powering the various components of the body-worn device 120. The power source 122 may comprise various types of batteries, including disposable and rechargeable batteries. In some embodiments, the power source 122 may comprise solar cells.

The body-worn device 120 may also include various indicators 132 adapted to convey various information to the user of the body-worn device 120. For example, indicators 132 may be utilized to indicate the power status (on or off) of the body-worn device 120, the charge remaining in the power source 122, the remaining volume available in the cartridge 126 (e.g., whether the cartridge is full or nearing full), and the like. The indicators 132 may be visual (e.g., lights) and/or audible (e.g., alarms). For example, an audible and/or visual alarm may be activated when the cartridge 126 is nearing full, or if the power source 122 is running out of charge.

FIG. 44B illustrates an exemplary embodiment of a body-worn device 120 which includes an anti-coagulant insert 134 which includes anti-coagulant which is applied to the biological fluid 16 within the body-worn device 120 to prevent clotting or coagulation of the biological fluid 16 within the body-worn device 120 as discussed herein. A removable anti-coagulant insert 134 of such anti-coagulant may be removably connected to the body-worn device 120 such that the anti-coagulant within the anti-coagulant insert 134 may be easily replenished as-needed. Also shown in FIG. 44B is a buffer fluid insert 136 which may be utilized to collect or replenish optional buffer fluids. Such buffer fluids such as dilution fluids may be utilized for pre-sorting within the body-worn device 120 as discussed herein.

As shown in FIG. 45, the body-worn device 120 will generally comprise an inlet 123 and an outlet 124. The inlet 123 and outlet 124 of the body-worn device are generally adapted to be connected to intravenous (IV) or catheter ports 129a, 129b of a catheter 128 which is inserted into the body of the patient 12 to receive a biological fluid 16 from a biological fluid source 17. It should be appreciated that the catheter 128 may be installed at various locations on a patient's 12 body, and thus FIGS. 44A and 44B should not be construed as limiting in that regard. The body-worn device 120 may be worn adjacent to the catheter entering the body, or more distant from that position. Thus, the length of the catheter 128 may vary widely in different embodiments.

In some embodiments, the catheter 128 may be fluidly connected to the vascular system of a patient 12 such that the vascular system of the patient 12 acts as a biological fluid source 17 for a biological fluid 16 comprised of blood. In other embodiments, the catheter 128 may be fluidly connected to the nervous system of a patient 12 such that the nervous system of the patient 12 acts as a biological fluid source 17 for a biological fluid 16 comprised of cerebrospinal fluid. In other embodiments, the catheter 128 may be fluidly connected to the lymphatic system of a patient 12 such that the lymphatic system of the patient 12 acts as a biological fluid source 17 for a biological fluid 16 comprised of lymphatic fluid.

By way of example, biological fluid 16 comprised of blood may be accessed through arteriovenous grafts, fistulas, or catheters 128 commonly used in aphaeretic treatments such as dialysis. Access to other types of biological fluid 16 such as cerebrospinal fluid could be through the lumbar, peritoneum, or the ventricles in the skull. Thus, it should be appreciated that the catheter 128 may be positioned at various locations on the body of the patient 12, such as but not limited to the head, arms, chest, legs, hands, feet, and the like.

Continuing to reference FIG. 45, it can be seen that the body-worn device 120 may comprise one or more pumps 125 for controlling flow of the biological fluid 16 entering and exiting the body-worn device 120. The pump 125 may include a pressure sensor for monitoring the pressure of the biological fluid 16. The pump 125 may be configured to run continuously or only at certain times or depending upon certain conditions. The pump 125 may be operated by the control unit 80.

As an example, the pump 125 may activate to draw a sample comprising a set volume of biological fluid 16 onto the fluid receiving device 30. Upon the set volume of biological fluid 16 being transferred to the fluid receiving device 30, the pump 125 may deactivate during the scanning process. After scanning the sample of the biological fluid 16, the pump 125 may activate again so as to direct the scanned sample of the biological fluid 16 either to a removable cartridge 126 or back to the biological fluid source 17 via the outlet 124. In some embodiments, the pump 125 may be adapted to automatically deactivate under certain conditions, such as upon pressure being detected as being above or below certain thresholds.

The biological fluid 16 will generally be routed from the inlet 123 into a microfluidic fluid receiving device 30 such as is described herein. It should be appreciated that multiple fluid receiving devices 30 may be utilized in the body-worn device 120 in certain embodiments, either in parallel or in series. When the biological fluid 16 is in the fluid receiving device 30, the scanner 70 will scan the contents of the fluid receiving device 30. An anti-coagulant may be applied to the biological fluid 16 prior to entering the fluid receiving device 30 so as to prevent the biological fluid 16 from coagulating while in the body-worn device 120.

One or more scanners 70 are directed towards the fluid receiving device 30 to scan the biological fluid 16 within the fluid receiving device 30. The scanner 70 will generally be communicatively connected to a control unit 80. The control unit 80 may be located within the housing 121 of the body-worn device 120, such as by use of a microprocessor, microcontroller, system-on-a-chip, or the like. In some embodiments, the scanner 70 may be communicatively connected to a remote control unit 80, such as through use of a communications network. By way of example, the scanner 70 may be communicatively connected to a control unit 80 by Bluetooth, Wi-Fi, radio waves, or various other communications methods known in the art.

The results of the optical scan of the biological fluid 16 within the body-worn device 120 by the scanner 70 are generally transferred to the control unit 80 for processing and detection of the biological fluid constituents 13. The data from the scanner 70 is compared to the reference data 91 and analyzed by the control unit 80 to classify the biological fluid constituents 13 within the biological fluid 16. One or more valves 127 may be utilized to direct the biological fluid 16 along at least two different paths depending upon the analysis of the biological fluid 16 by the control unit 80.

If only healthy, desirable constituents 15 are detected, the one or more valves 127 may direct the biological fluid 16 along a return path 60 to be returned to the biological fluid source 17. More specifically, the biological fluid 16 may exit the body-worn device 120 through its outlet 124 and returned to the biological fluid source 17 by the catheter 128.

If there are undesired constituents 14 or undesired constituents such as malignant cells, the one or more valves 127 may direct the biological fluid 16 along an isolation path 50 to a cartridge 126. The cartridge 126 may be removable and, in some embodiments, may be disposable. The cartridge 126 generally includes a cavity within which the biological fluid 16 may be stored and sequestered.

The cartridge 126 is generally removably connected to the housing 121 of the body-worn device 120. However, in some embodiments, the cartridge 126 may instead be fixedly connected to the housing 121 and instead include an access port through which the biological fluid 16 may be drained from the cartridge 126 as-needed. Thus, the valve(s) 127 of the body-worn device 120 will generally have one inlet and a pair of outlets. The inlet of the valve(s) 127 is fluidly connected to the fluid receiving device 30. A first outlet of the valve(s) 127 is fluidly connected to the cartridge 126 and a second outlet of the valve(s) 127 is fluidly connected to the outlet 124 of the body-worn device 120.

The cartridge 126, which may be replaceable and/or disposable, May include built-in sensors to identify the protein expression of the cells. Data from such built-in sensors may be transferred to the control unit 80 for further processing. Thus, the filtered contents of the cartridge may be diagnostically profiled by the control unit 80.

Figure 46:
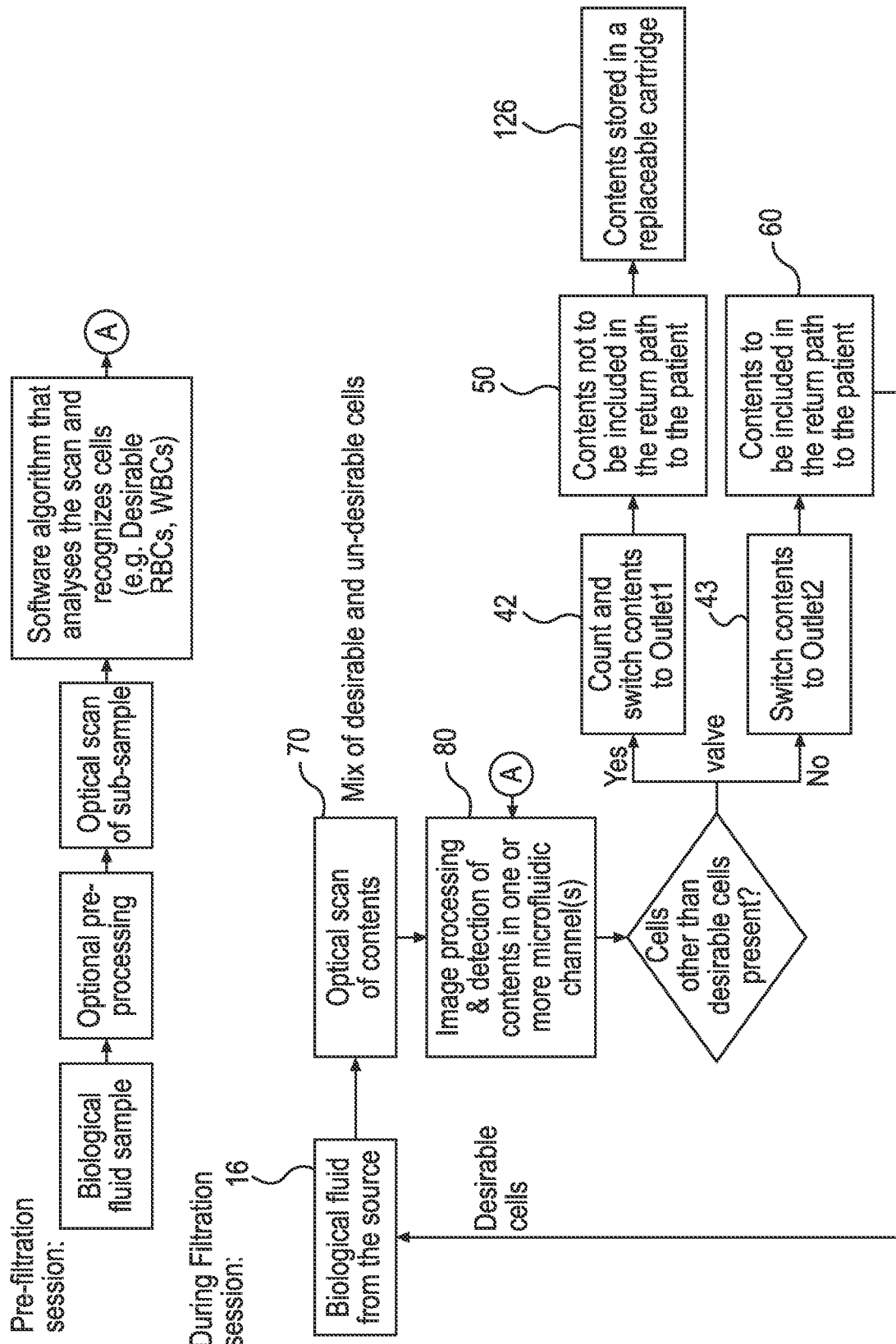
FIG. 46 is a flowchart illustrating the usage of a body-worn device of a biological fluid filtration system in accordance with an example embodiment.

FIG. 46 illustrates an exemplary method of filtering a biological fluid 16 utilizing a body-worn device 120. Prior to filtration, the catheter 128 will generally be inserted within the patient 12 and fluidly connected to the biological fluid source 17. The catheter 128 will be fluidly connected to the inlet 123 of the body-worn device 120 and, in some embodiments, to the outlet 124 of the body-worn device 120. Thus, the catheter 128 may include a pair of intravenous (IV) or catheter ports 129a, 129b, such as an outlet catheter port 129a and an inlet catheter port 129b. In such embodiments, the outlet catheter port 129a is fluidly connected to the outlet 124 of the catheter 128 and the inlet catheter port 129b is fluidly connected to the inlet 123 of the catheter 128 such as shown in FIGS. 44A and 44B.

Biological fluid 16 is drawn from the biological fluid source 17 through the catheter 128, entering the body-worn device 120 through its inlet 123. Anti-coagulant may be applied to the biological fluid 16 as-needed from the anti-coagulant insert 134. The biological fluid 16 is drawn into the fluid receiving device 30 by the pump 125, which may be controlled by the control unit 80. The scanner 70 then scans the biological fluid 16 within the fluid receiving device 30, and the resulting data is transferred to the control unit 80 for analysis and detection of the biological fluid constituents 13 within the biological fluid 16.

The manner by which the biological fluid 16 is scanned by the scanner 70 and analyzed by the control unit 80 may vary as described herein. If a pre-filtration session was performed, the data collected therefrom may be utilized by the control unit 80 in detecting and identifying the biological fluid constituents 13 of the biological fluid 16.

In some embodiments, the control unit 80 may be configured to maintain a 2 count of detected biological fluid constituents 13, including healthy cells, malignant cells, and unidentified cells. The control unit 80 may also be configured to keep track of the total count of cells analyzed, the total volume of biological fluid 16 analyzed, cells detected per volume of biological fluid 16, and other data.

Any biological fluid 16 samples scanned by the scanner 70 and determined by the control unit 80 to include undesirable constituents 14 are directed by the valve(s) 127 along an isolation path 50 into the cartridge 126. Any biological fluid 16 samples scanned by the scanner 70 and determined by the control unit 80 to include only healthy, desirable constituents 15 is instead routed by the valve(s) 127 along a return path 60 out of the body-worn device 120 via its outlet 124 to be returned to the biological fluid source 17 by the catheter 128.

Figure 47:
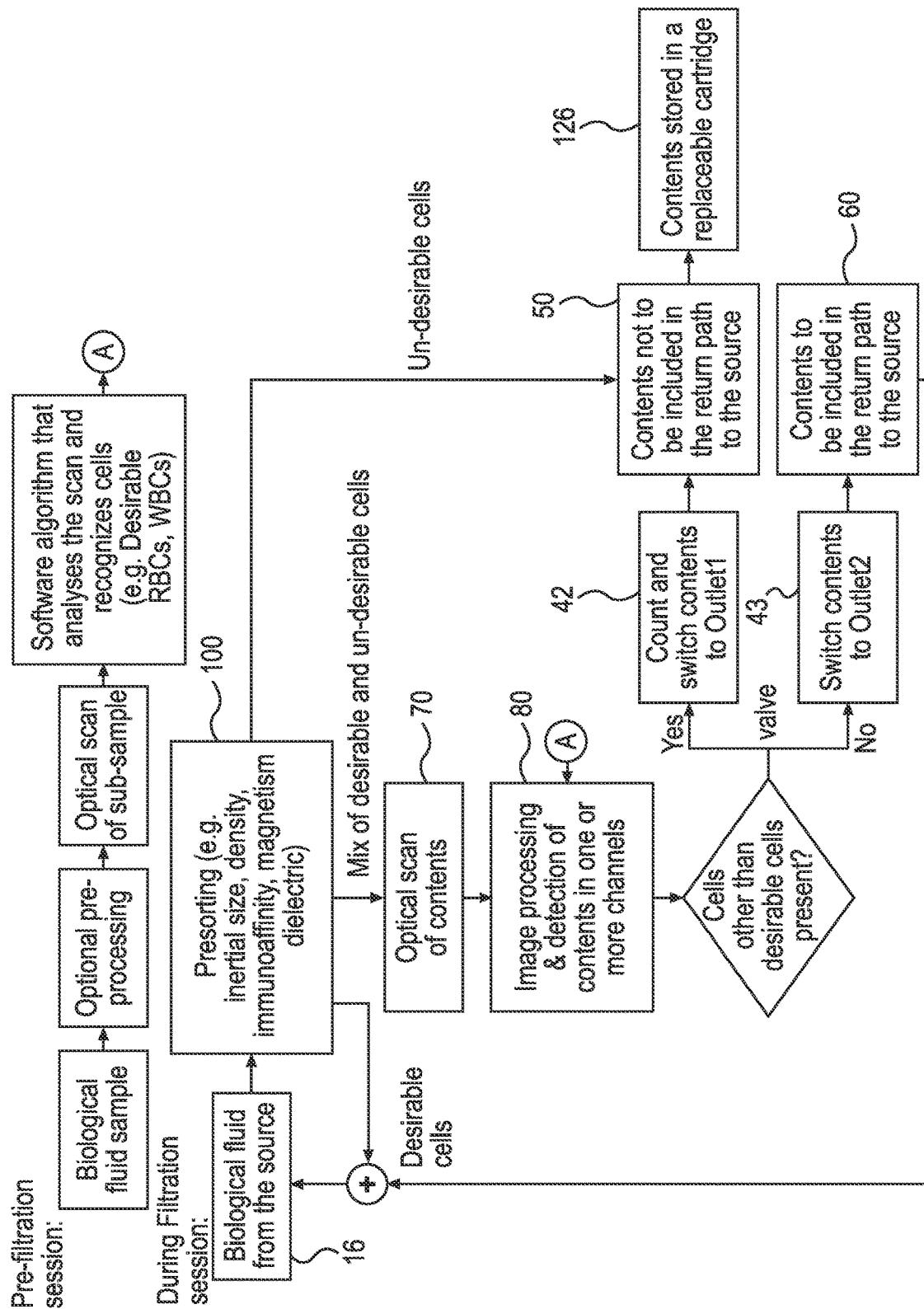
FIG. 47 is a flowchart illustrating the usage of a body-worn device with a pre-sorting stage of a biological fluid filtration system in accordance with an example embodiment.

FIG. 47 illustrates a method of filtering a biological fluid 16 with a body-worn device 120 including a presorting stage. As shown in FIG. 47, the biological fluid 16 is drawn from the biological fluid source 17 into the body-worn device 120 via its inlet 123 to enter a pre-sorting stage. The presorting stage sorts the biological fluid 16 by various methods described herein (e.g., inertial, size, density, immunoaffinity, magnetic, dielectric). In some embodiments, the presorting stage may include a miniature centrifuge within the body-worn device 120. In some embodiments, the pre-sorting stage may utilize a buffer fluid insert 136 from which buffer fluids and/or dilution fluids may be retrieved for presorting.

After the presorting stage, any desirable constituents 15 may be returned along a return path 60 through the outlet 124 of the body-worn device 120 to the biological fluid source 17 via the catheter 128. Any undesirable constituents 14, or unhealthy cells, may be transferred to the cartridge 126 along an isolation path 50. Any sample of biological fluid 16 after the presorting stage which includes a mixture of recognized fluid constituents 13 and undesirable constituents 14, such as a mixture of healthy cells and unhealthy cells, are transferred to the fluid receiving device 30 to be optically scanned by the scanner 70 and processed by the control unit 80 in the manners described elsewhere herein.

Figure 48:
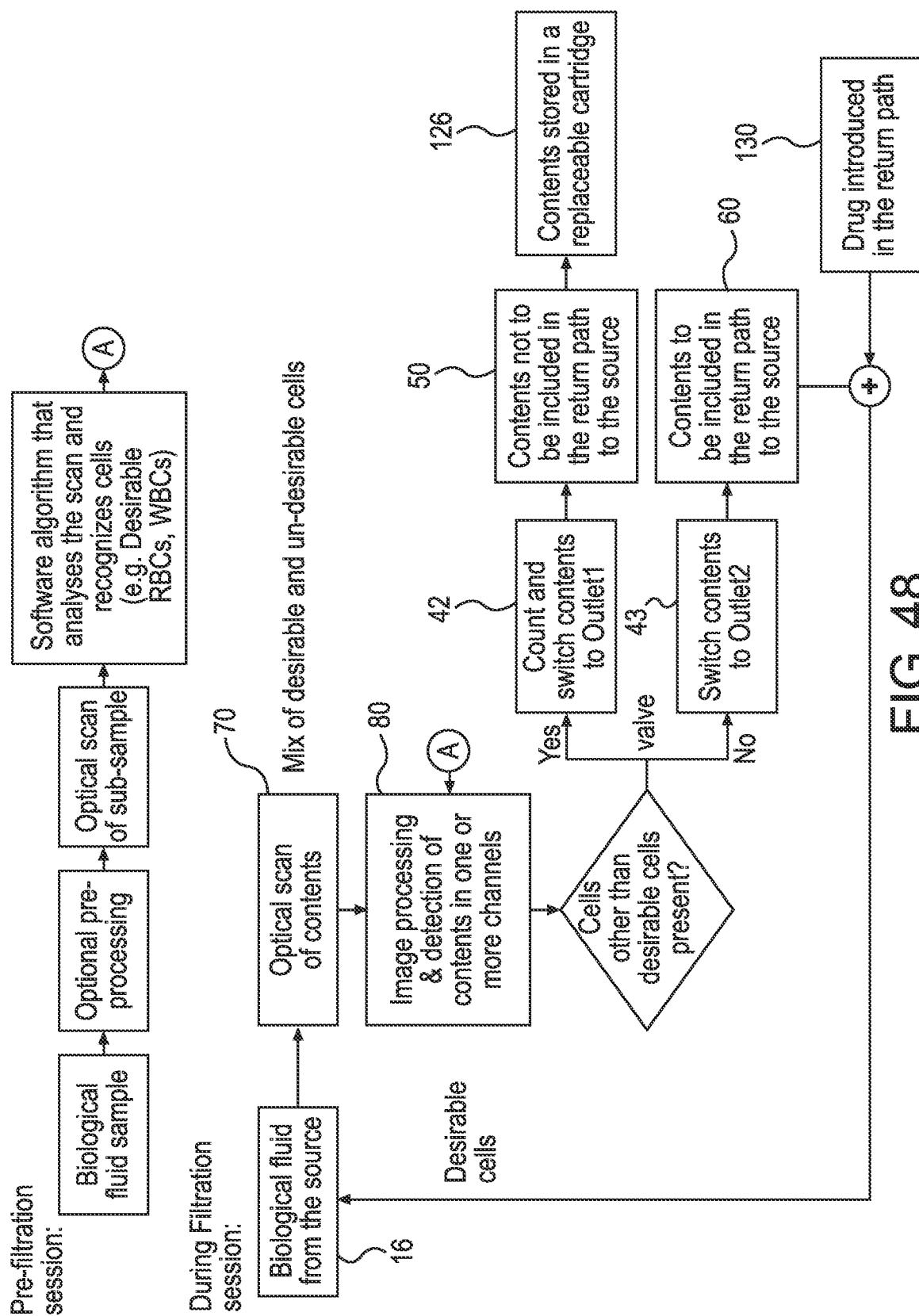
FIG. 48 is a flowchart illustrating the usage of a body-worn device with drug infuser in the return path of a biological fluid filtration system in accordance with an example embodiment.

FIG. 48 illustrates a method of filtering a biological fluid 16 within a body-worn device 120 which includes a drug infuser 130 in the return path 60. As shown in FIG. 48, a drug infuser 130 may be positioned along the return path 60 between the valve(s) 127 and the outlet 124 of the body-worn device 120. Drugs or treatments may be infused by the drug infuser 130 with the filtered biological fluid 16 prior to returning to the biological fluid source 17 through the outlet 124 of the body-worn device 120 via the catheter 128. Various drugs or treatments may be utilized, and the body-worn device 120 may be configured such that the drugs or treatments may be routinely re-filled or switched as-needed. In other example embodiments, the body-worn device 120 may employ additional buffers or dilution fluids to presort the biological fluid 16. Additionally, in some embodiments, the body-worn device 120 may employ anti-coagulants to prevent clotting.

Figure 53:
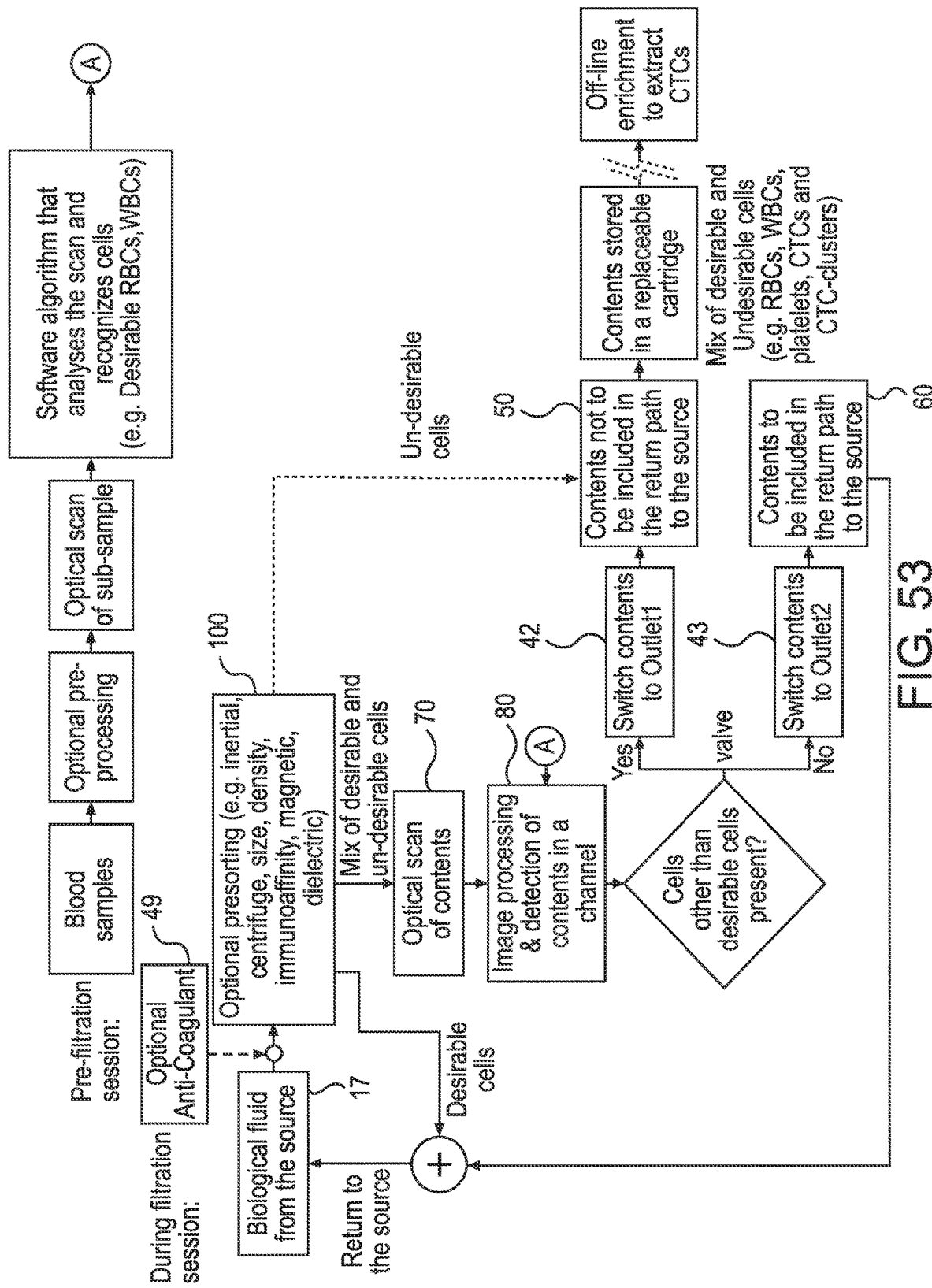
FIG. 53 is a block diagram illustrating the usage of a body-worn device to filter and sequester small samples of blood containing CTCs and CTC-clusters of a biological fluid filtration system in accordance with an example embodiment.

FIG. 53 illustrates an exemplary method utilized for a multi-stage body-worn filtration system in which the body-worn device 120 could utilize optical filtration methods to filter and sequester samples of biological fluids 16 (e.g., blood) that contain CTCs and CTC-clusters. Such samples may be stored in a replaceable cartridge 126 that may then be further processed to enrich and extract CTCs and CTC-clusters.

As shown in FIG. 53, biological fluid 16 from a biological fluid source 17 may be treated with optional anti-coagulant 49 prior to entering a microfluidic separation module 100 for optional presorting. Any undesirable constituents 14 are immediately transferred to an isolation path 50. Any samples containing both undesirable constituents 14 and desirable constituents 15 are transferred to a fluid receiving device 30 and scanned by a scanner 70. The resulting scanned data 90 is processed by the control unit 80. If any undesirable constituents 14 are detected, the sample may be transferred along an isolation path 50 to be stored in a cartridge 126 for off-line enrichment to extract CTCs. If only desirable constituents are detected, the sample may be returned to the biological fluid source 17 by a return path 60.

Figure 44C:
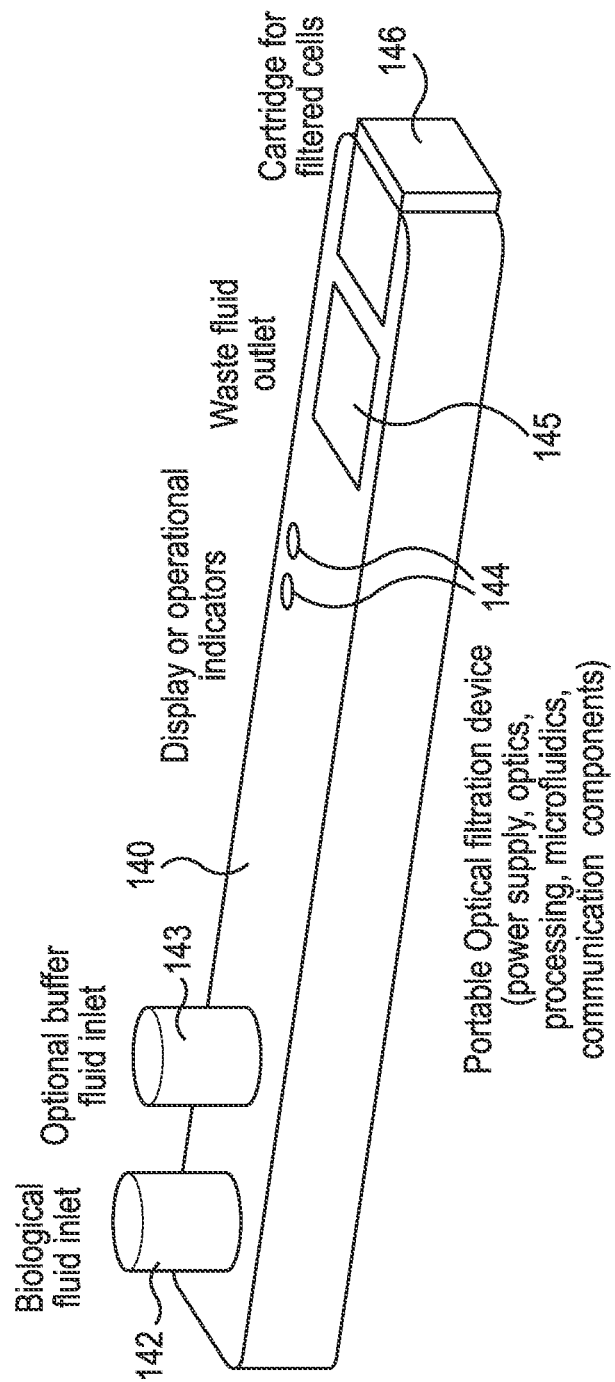
FIG. 44C is a perspective view of a portable filtration device of a biological fluid filtration system in accordance with an example embodiment.

FIG. 44C illustrates an exemplary portable device 140 which is portable (as opposed to body-worn) and may be utilized in a non-aphaeretic setting (e.g., to process cerebrospinal fluid, saliva, or urine to extract unhealthy cells such as CTCs). As shown in FIG. 44C, the portable device 140 will generally include a biological fluid inlet 142 through which biological fluid 16 may be introduced into the portable device 140. An optional buffer fluid inlet 143 may be utilized to introduce various buffer or dilation fluids for presorting of the biological fluid 16. The buffer fluid may be replaced or replenished as needed. Such an embodiment may also include anti-coagulants if utilized to process fluids such as blood.

Continuing to reference FIG. 44C, the portable device 140 may include indicators 144 (e.g., audible or visual) which provide various information about the operability of the portable device 140 (e.g., on/off, flow blockage, etc.). Internally to the portable device 140, a fluid receiving device 30 and scanner 70 are provided for scanning the biological fluid 16 within the portable device 140. Although not shown, the portable device 140 will generally include an internal power source, though the portable device 140 may be externally powered (e.g., by a wall socket) in some embodiments. The portable device 140 may include its own internal control unit or may be communicatively connected to a remote control unit for processing scanned data 90.

As shown in FIG. 44C, the portable device 140 may include a waste fluid outlet 145 through which waste fluids and other disposables may be removed from the portable device 140. The portable device 140 will also generally include a removable cartridge 146 which stores any filtered cells. The cartridge 146 may be emptied and replaced as-needed to process additional biological fluids 16.

J. Closed-Loop Filtration, Treatment, and Monitoring.

Figure 49:
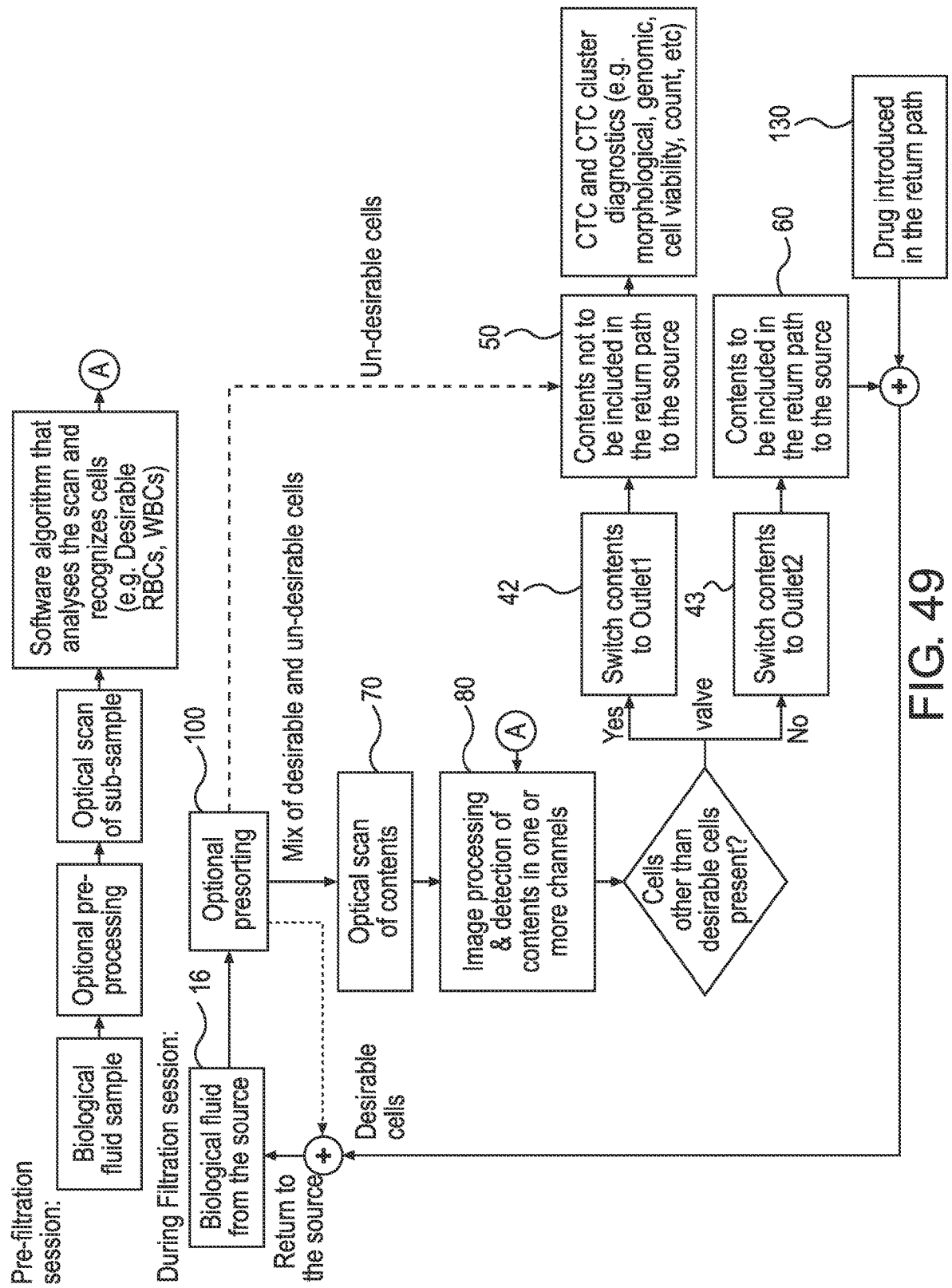
FIG. 49 is a block diagram illustrating a closed-loop filtering, monitoring, and testing system of a biological fluid filtration system in accordance with an example embodiment.
Figure 50:
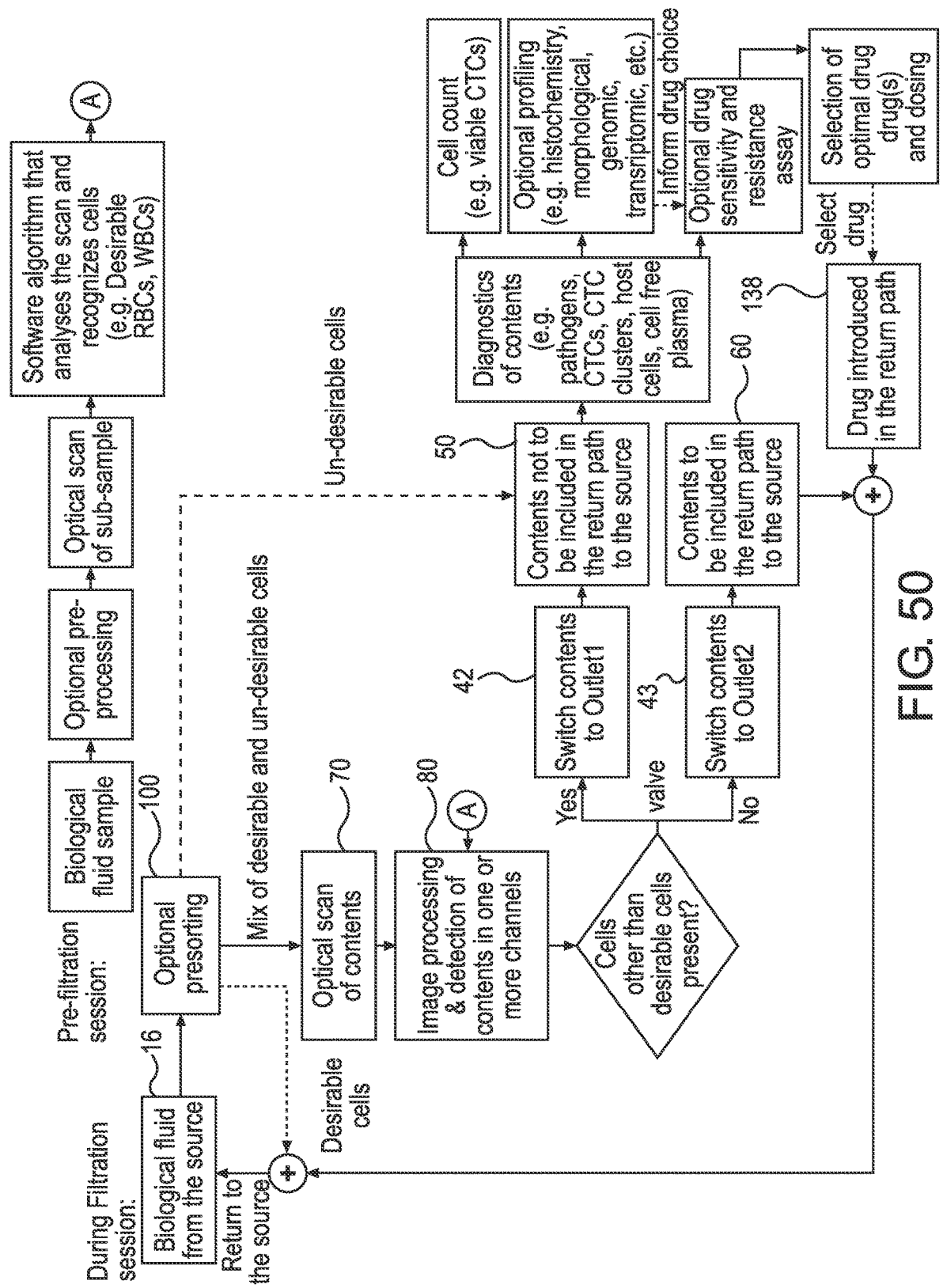
FIG. 50 is a block diagram illustrating a closed-loop filtering, monitoring, and testing system of a biological fluid filtration system utilizing drug choice optimization in accordance with an example embodiment.

FIGS. 49 and 50 illustrate an exemplary embodiment of utilizing a biological fluid filtration system 10 for closed-loop filtration, treatment, and monitoring of undesirable constituents 14 such as harmful cells. In such an embodiment, undesirable constituents 14 such as CTCs or CTC-clusters are filtered using the optical filtration methods and systems described herein, with a drug or treatment (e.g., chemotherapeutic agents, combination of drugs, immunotherapy treatments, etc.) being introduced in the return path 60 to check for its therapeutic effect.

In an example embodiment, the ratio of undesirable constituents 14 within a certain volume of biological fluid 16 may be monitored continuously or sporadically to determine any changes post-administration of a certain drug or treatment. A decreasing ratio of undesirable constituents 14 such as viable (living) CTCs within a biological fluid 16 during aphaeresis may be an indication that a certain drug or treatment is effective.

For example, various optical scanning methods described herein (e.g., digital holographic microscopy) may be utilized to count undesirable constituents 14 per given volume of processed biological fluid 16. In some embodiments, staining or fluorescence may be utilized. As with the other systems and methods described herein, the closed-loop filtration, treatment, and monitoring may be utilized in connection with humans or animals.

FIG. 49 illustrates an exemplary method of filtering, monitoring, and treating harmful cells within a biological fluid 16. As with the other systems and methods described herein, a pre-filtration session may be performed to improve the accuracy of the control unit 80 in analyzing the biological fluid 16 and identifying any biological fluid constituents 13. Data from the pre-filtration session may be utilized in whole or in part in development of the reference data 91 which is used by the control unit 80 to analyze biological fluid 16 and identify any biological fluid constituents 13 as discussed herein. The reference data 91 could include images and/or data of biological fluid constituents 13 from the same patient or from other individuals.

As shown in FIG. 49, biological fluid 16 is drawn from a biological fluid source 17. Presorting may be applied as discussed herein, with any undesirable constituents 14 being sequestered along an isolation path 50 immediately after presorting. The remaining sample of biological fluid 16 is then optically scanned by the scanner 70 and the resulting data undergoes analysis by the control unit 80 to identify any biological fluid constituents 13.

Any samples of biological fluid 16 containing anything other than desirable constituents 15 are transferred along the isolation path 50 to be sequestered along any undesirable constituents 14 from the presorting (if performed). All such undesirable constituents 14 are monitored such as by counting the number of viable CTCs or other harmful cells per volume of processed biological fluid 16.

FIG. 50 illustrates an exemplary method of filtering, monitoring, and treating harmful cells within a biological fluid 16 which includes presorting of cells prior to optical scanning, diagnostic profiling, and ex vivo drug testing of undesirable constituents 14 to identify an optimal drug or treatment to be administered in the return path 60. In an exemplary embodiment, a drug or treatment may be tested on filtered cells by measuring changes to their cellular properties using optical techniques (e.g., digital holographic microscopy).

As an example embodiment, prior to drug administration, a portion of the filtered cells may be processed for genomic data which aids in identifying suitable drug targets. Those drugs are tested, potentially at various concentrations, on the remaining portion of the filtered cells to determine which drug or treatment has the most intended therapeutic effect so as to validate the optimal drug or treatment choice. Subsequently, the optimal drug or treatment is then introduced in the return path 60.

With reference to FIG. 50, it can be seen that a biological fluid 16 is drawn from a biological fluid source 17, pre-sorted, scanned, and analyzed as described herein. Contents which are sequestered along the isolation path 50, such as undesirable constituents 14, undergo diagnostics such as cell counting (e.g., of viable CTCs), profiling (e.g., histochemistry, genomic transcriptomic, etc.), and the like. The diagnostics are utilized to determine potential drugs or treatments.

After determining potential drugs or treatments based on diagnostics of undesirable constituents 14 sequestered after presorting and optical filtration, optional drug sensitivity and resistance assay may be performed. Based upon the results of the assay, optimal drugs or treatments, including dosing, may be selected. Such optimal drugs or treatments are then introduced in the return path 60 to be returned to the biological fluid source 17.

Such an embodiment may be utilized to process multiple biological fluids 16 from a biological fluid source 17 at the same time. Different types of filtered cells may be held separately so that their counts, diagnostic profiling, and drug testing may be conducted separately. Optical scanning could include single or multiple parallel fluid receiving devices 30. In some embodiments, the foregoing methods may be performed on a sample of biological fluid 16.

K. Methods of Biological Fluid Filtration.

Generally, the methods of biological fluid filtration are directed to the removal of undesirable constituents 14 which may comprise, for example, disease-related biological or chemical entities, from a biological fluid 16 by optically inspecting the constituents 13 in the biological fluid 16 and filtering those that are not recognized to be among the desirable constituents 15 of the biological fluid 16. The methods of biological fluid filtration may be applied in a therapeutic context, a diagnostic context, or both, as described herein.

Generally, the methods involve directing a biological fluid 16 to a fluid receiving device 30, optically scanning the biological fluid 16 within the fluid receiving device 30 by a scanner 70 to generate the scanned data 90 of the biological fluid 16, comparing the scanned data 90 of the biological fluid 16 with the reference data 91 by the control unit 80; returning the biological fluid 16 to the biological fluid source 17 if the scanned data 90 of the biological fluid 16 includes only desirable constituents 15 exhibiting criteria that sufficiently match with any of the desirable constituents 15 of the reference data 91 by the control unit 80; and isolating the biological fluid 16 from the biological fluid source 17 if the scanned data 90 of the biological fluid 16 includes one or more constituents not exhibiting criteria that sufficiently match with any of the desirable constituents 15 of the reference data 91 by the control unit 80. The biological fluid filtration system 10 described herein may be used to carry out the methods.

In one embodiment, the method of biological fluid filtration includes pre-processing of the biological fluid 16 to separate particular cellular constituents of the biological fluid 16 for promotion to the fluid receiving device 30, as described above. Methods may also optionally include additional filtration processes, including antigen based filtration, described above.

In an alternative embodiment, the method includes pre-processing of a fluid sample of the biological fluid source 17 to obtain the reference data 91 differentiating cell image data characteristics of desirable constituents 15 to more precisely tailor the reference data 91 the biological fluid system, including any heterogeneity among its desirable constituents 15. Such pre-processing may rely upon machine learning and/or artificial intelligence models in order to more accurately and efficiently differentiate between undesirable constituents 14 and desirable constituents 15.

In an alternative embodiment, the reference data 91 is developed based on relevant normative subpopulation data concerning the desirable constituents 15 of the biological fluid system.

L. Non-Aphaeretic Filtration Methods.

It should be appreciated that, while many of the embodiments described herein utilize aphaeretic systems, additional embodiments may be non-aphaeretic. One such exemplary embodiment is shown in FIG. 42, in which a non-aphaeretic implementation is utilized for the removal of tumor cell contaminants from analogous stem-cell transplant products. Another exemplary embodiment is shown in FIG. 44C, in which a portable device 140 may be utilized for non-aphaeretic filtration.

As shown in FIG. 42, biological fluid 16 comprised of a leukapheresis product may be collected from a biological fluid source 17. Pre-sorting may be performed by a microfluidic separation module 100 so as to separate the leukapheresis product into three primary divisions: (1) separated red blood cells, plasma, and small cells; (2) separated white blood cells and small CTCs; and (3) separated large CTC-clusters. In some embodiments, pre-sorting may involve the use of chemical agents and/or buffer solutions for red blood cell and platelet separation or lysis.

The first division, comprised of separated red blood cells, plasma, and small cells, may be transferred to a fluid chamber to hold filtered plasma and healthy cells for transplantation. The third division, comprised of large CTC-clusters, May be transferred for diagnostic processing (e.g., genomic, transcriptomic, metabolomics, drug sensitivity and resistance) of CTCs, CTC-clusters, and cell-free plasma.

With respect to the second division, comprised of separated white blood cells and small CTCs, such contents may be inertial focused into one or more parallel fluid receiving devices 30 (e.g., microfluidic channels 31, microwell arrays 32, and/or droplet generators 34). Such contents may be scanned simultaneously or sequentially by the scanner 70. The control unit 80 will then analyze each sample to determine if cells other than healthy cells are present (e.g., undesirable constituents 14).

If no cells other than healthy cells are present in a given sample, that sample may be transferred to a fluid chamber along with the first division of separated red blood cells, plasma, and small cells. If cells other than healthy cells are present in a given sample, that sample may be further enriched (e.g., by returning to be reprocessed by a reprocessing path 62) or may be sequestered along with the third division of separated large CTC-clusters for diagnostic processing.

M. Operation of Illustrative Embodiments.

The systems and methods described herein may be utilized for therapeutic purposes, diagnostic purposes, or both. It should be appreciated that the methods and systems used to isolate biological fluids 16 containing undesirable constituents 14 may vary in different embodiments. Further, the methods and systems utilized for processing the isolated biological fluids 16 containing undesirable constituents 14 may vary in different embodiments depending upon whether such isolated biological fluids 16 are to be used for therapeutic purposes, diagnostic purposes, or some combination of both.

i. Therapeutic Systems and Methods.

As shown throughout the figures and discussed herein, the systems and methods described herein may be utilized for various therapeutic purposes. For example, therapeutic embodiments in which the undesirable constituents 14 are CTCs or CTC-clusters may be useful to reduce metastatic disease. As another example, therapeutic embodiments in which the undesirable constituents 14 are pathogens may be useful to treat infection, including sepsis.

ii. Aphaeretic Scanning and Filtration of Whole Blood Fluid with CTCs on a Microfluidic Channel Platform with Reference Image Dataset of Sampled Blood from Representative Individuals Other than the Patient.

Figure 12:
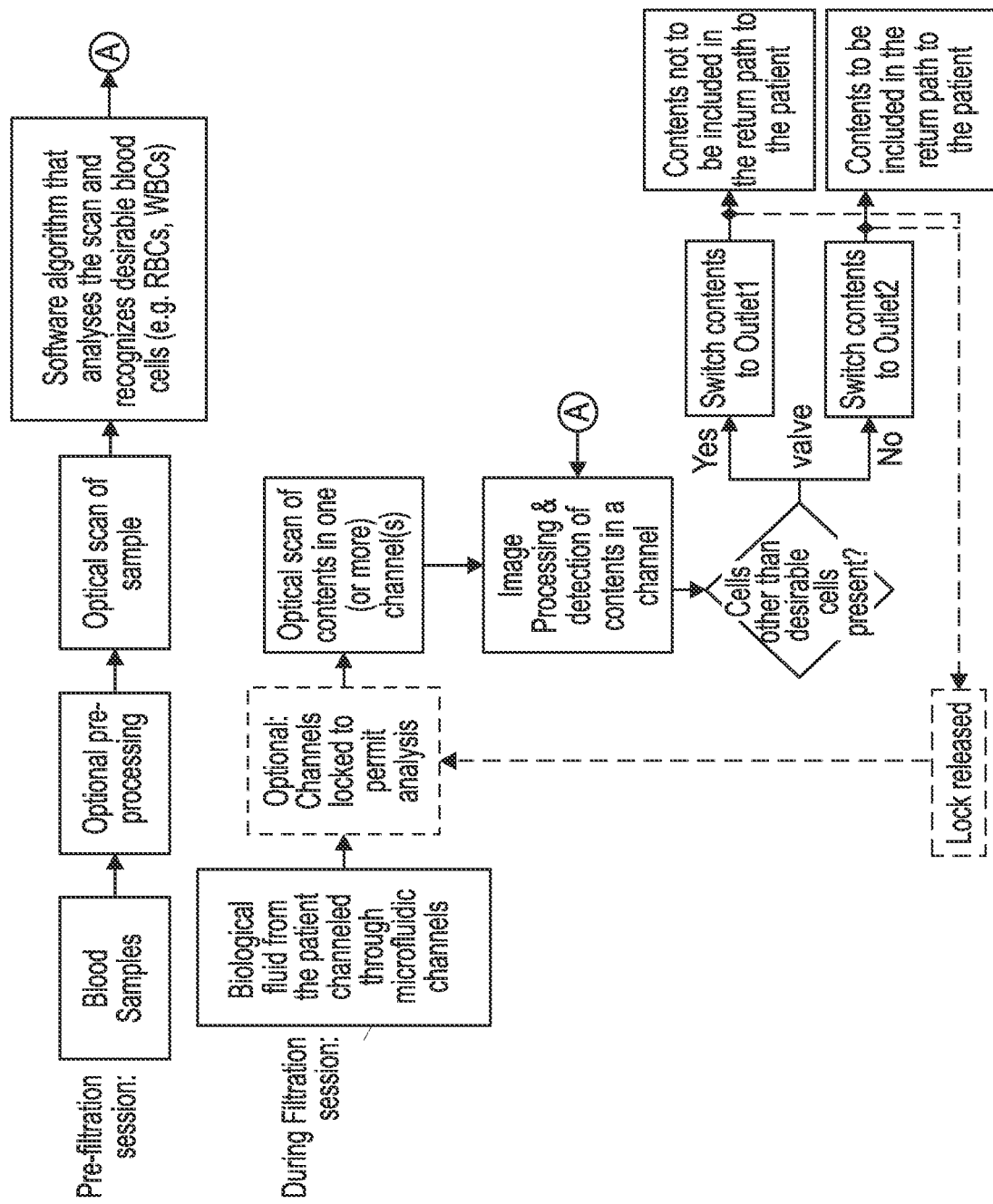
FIG. 12 is a block diagram of an aphaeretic system and method of removing undesirable constituents using microfluidic channels in accordance with an example embodiment.
Figure 13:
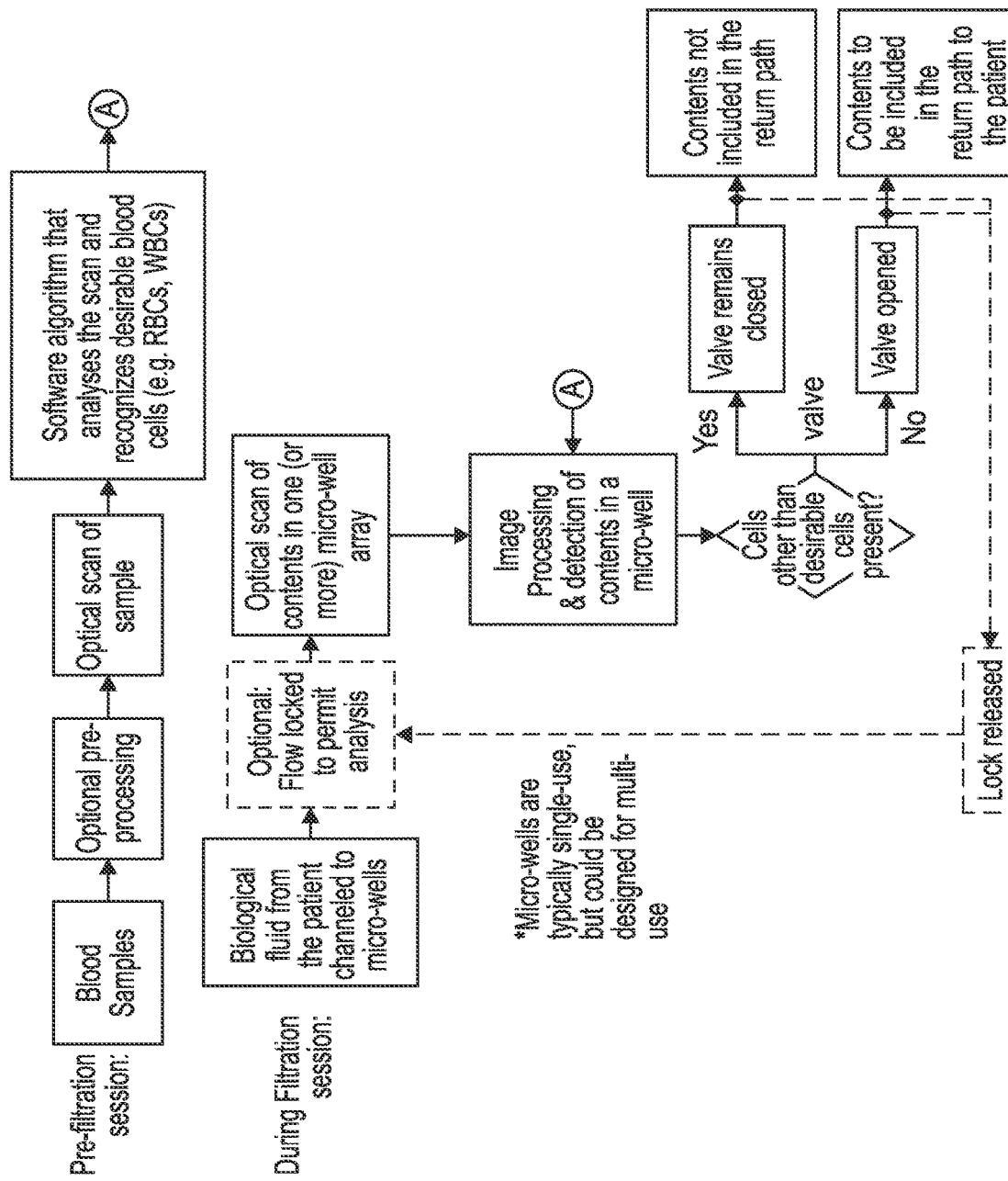
FIG. 13 is a block diagram of an aphaeretic system and method of removing undesirable constituents using microwell arrays in accordance with an example embodiment.

One illustrative embodiment is a system and method for aphaeretic scanning and filtration of whole blood to remove CTCs from a patient's circulatory system. As illustrated in FIGS. 12 and 27, whole blood is pumped from a patient 12 via a receiver path 20 to a fluid receiving device 30 comprising a batch of parallel microfluidic channels 31. Each channel 31 is optically scanned by a scanner 70 using DIC Microscopy, DHM or other appropriate imaging techniques to derive a scanned data 90 of the cells for each microfluidic channel 31.

The scanned data 90 is transferred to a control unit 80, which utilizes an image processing software program comprising an algorithm 82 designed to recognize healthy blood cells (i.e., erythrocytes, leukocytes and platelets) in the scanned data 90. More particularly, the algorithm 82 is designed to recognize patterns in the reference data 91 characteristic of each type of healthy blood cell and process each scanned data 90 transferred to the control unit 80 to determine whether those patterns are recognized in discreet image data obtained for each cell.

In an exemplary embodiment, the reference data 91 is obtained through DIC Microscopy, digital holographic microscopy, or other appropriate imaging techniques of blood samples taken from a representative sample of individuals other than the patient. Raw data is computer-processed to identify patterns in the images and/or data that reflect characteristics of each type of healthy blood cell, including, for example, cell size, shape, texture, phase deviations, solidity and luminance. Data reflecting those patterns is uploaded to the control unit 80 and stored to memory as the reference data 91.

With reference to FIG. 29, if all cells in a scanned microfluidic chamber are recognized by the algorithm 82 as healthy blood cells, then the image processing software program generates a first control signal instruction 83 to the control unit 80 to relay a control signal to the valve 40 to route channel contents to the return path 60. If, on the other hand, one or more of cells of the scanned microfluidic chamber 31 are not recognized by the algorithm 82, then the image processing software program generates a second control signal instruction 84 to the control unit 80 to relay a control signal 81 to the valve 40 to route channel contents to the isolation path 50. Filtered blood in the return path 60 is pumped back to the patient's circulatory system. CTC-rich fluid routed to the isolation path 50 is sequestered and optionally stored for further processing for diagnostic or therapeutic purposes.

iii. Aphaeretic Filtration of Leukocyte-Rich Blood Fluid with Small CTCs on a Microfluidic Channel Platform with Reference Image Dataset of Sampled Blood from Representative Individuals Other Than the Patient.

Figure 21:
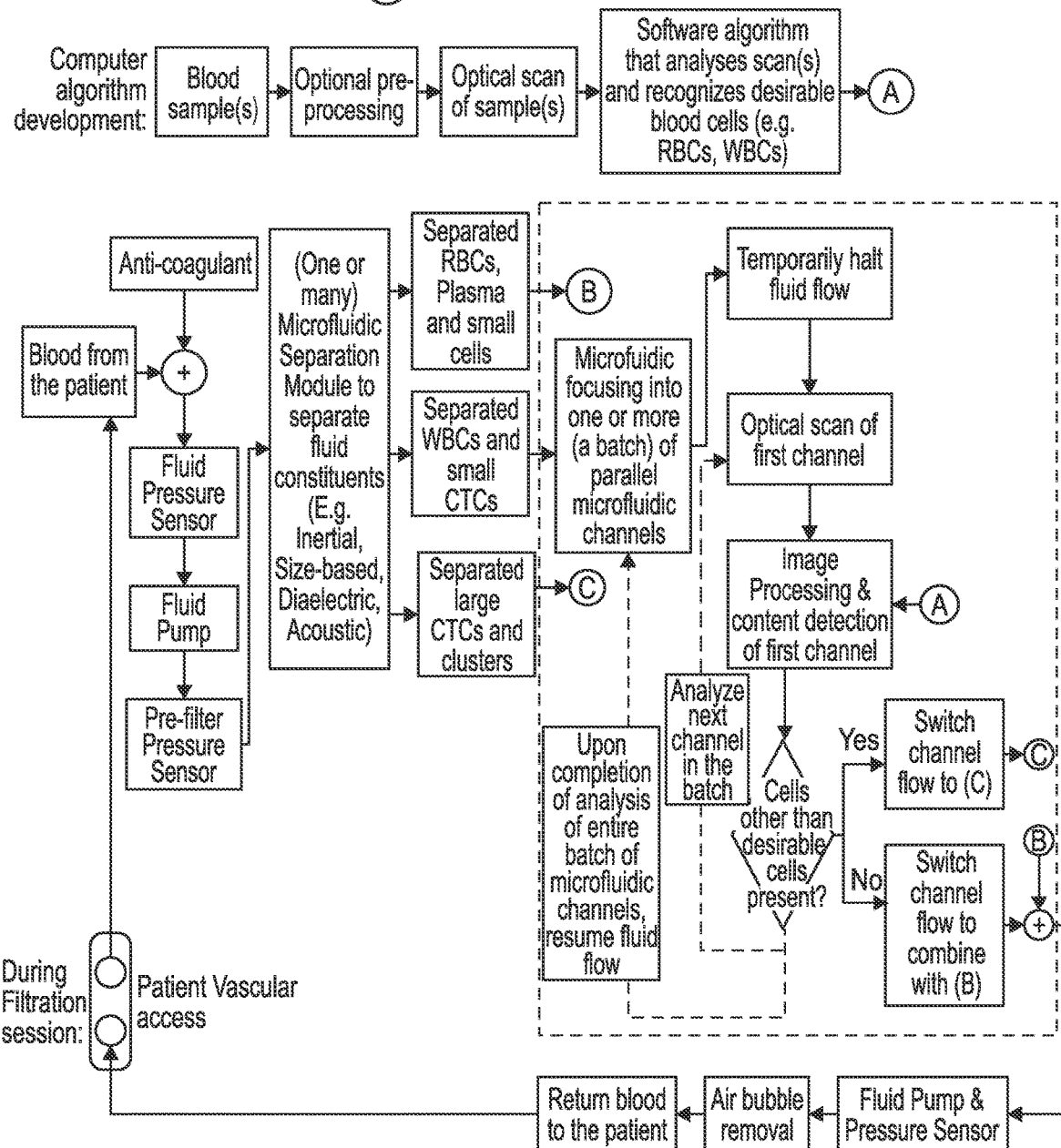
FIG. 21 is a block diagram of an aphaeretic system and method for removal of undesirable CTCs and CTC-clusters using blood samples from representative individuals other than the patient to obtain a reference data in accordance with an example embodiment.
Figure 22:
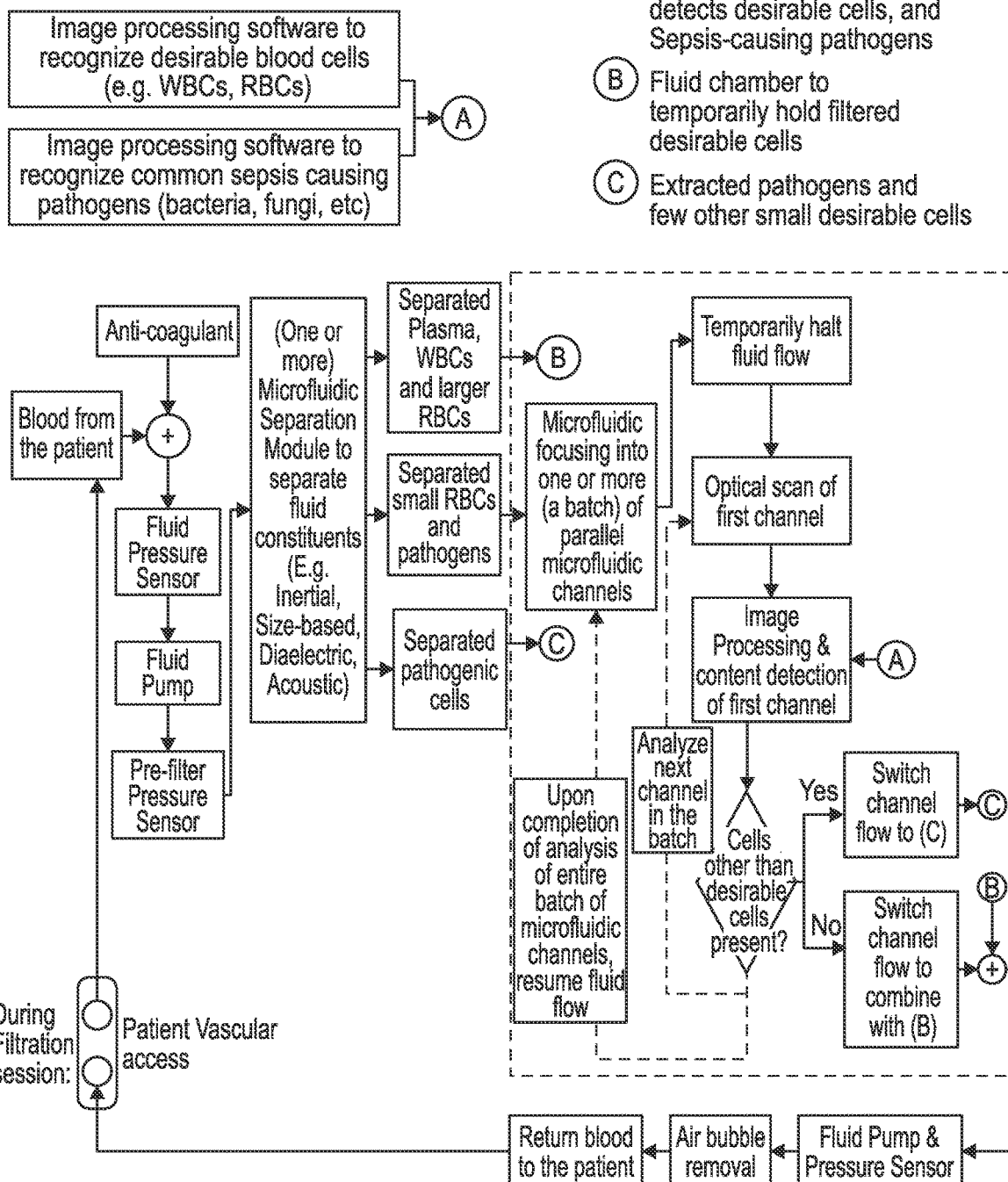
FIG. 22 is a block diagram of an aphaeretic system and method incorporating image data of pathogens into a reference data in accordance with an example embodiment.
Figure 23:
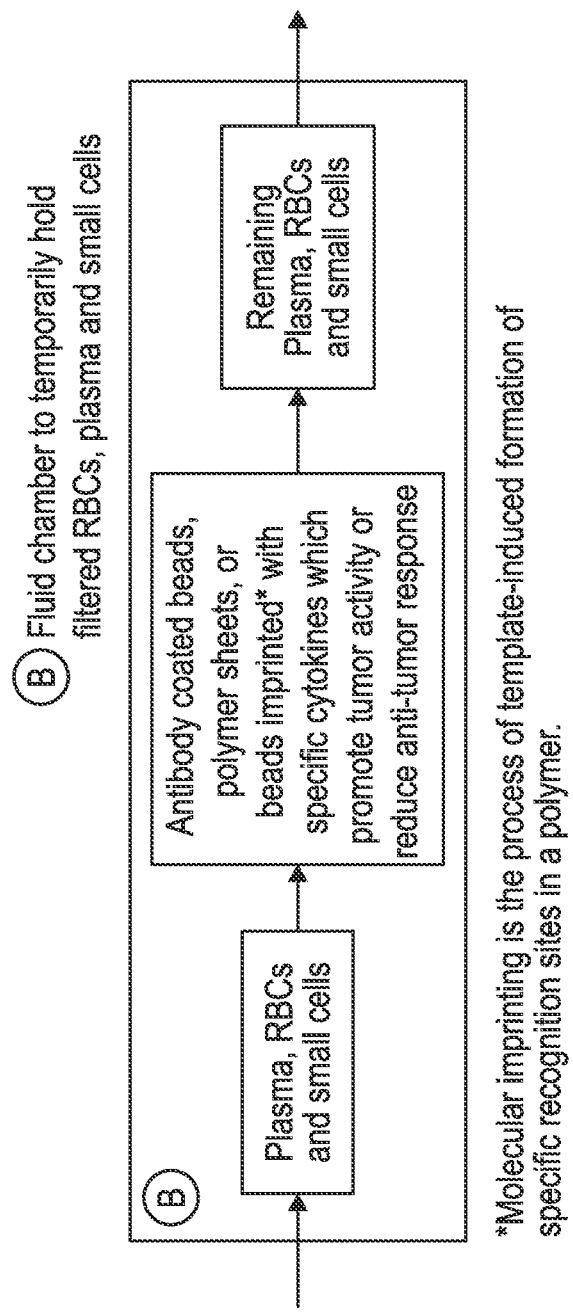
FIG. 23 is a block diagram of filtration of cytokines from blood component fluid in accordance with an example embodiment.
Figure 24:
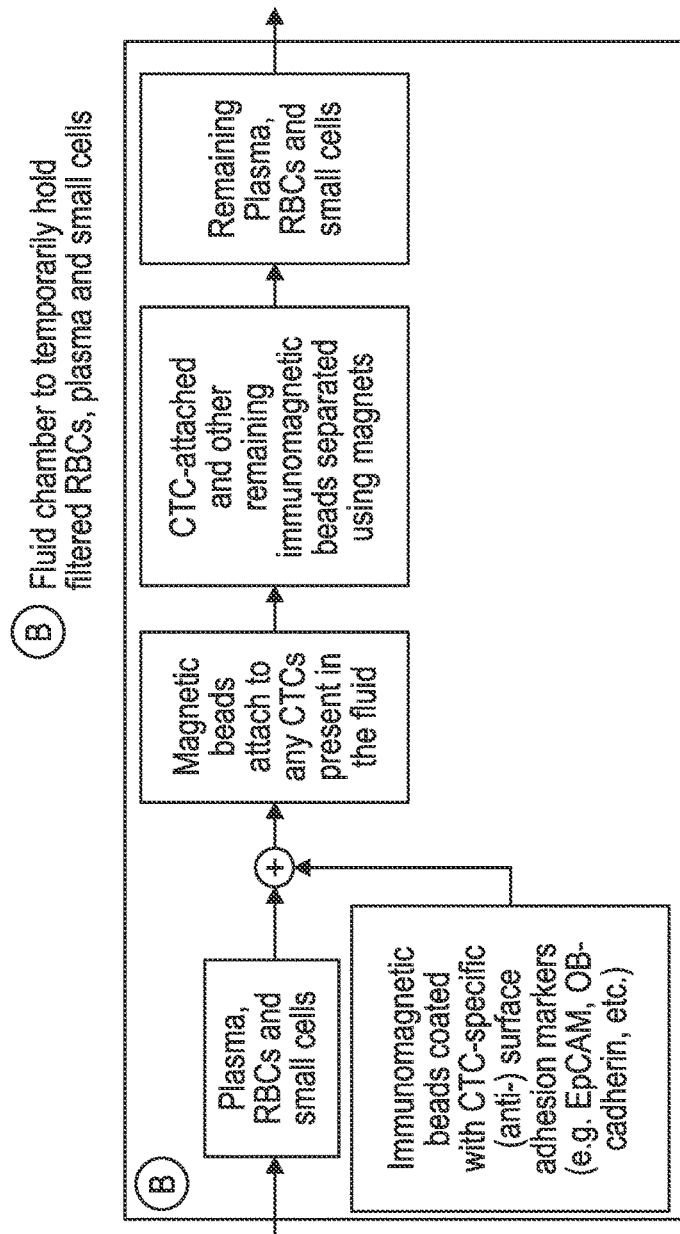
FIG. 24 is a block diagram of immunomagnetic filtration of CTCs from blood component fluid in accordance with an example embodiment.
Figure 25:
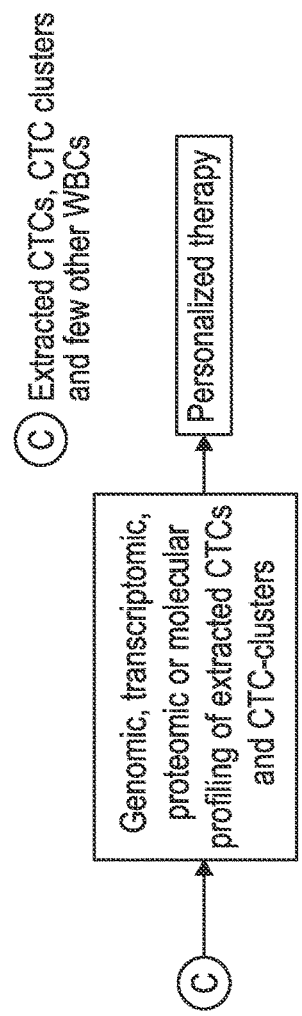
FIG. 25 is a block diagram of molecular and genetic profiling of undesirable CTCs removed from blood in accordance with an example embodiment.
Figure 26:
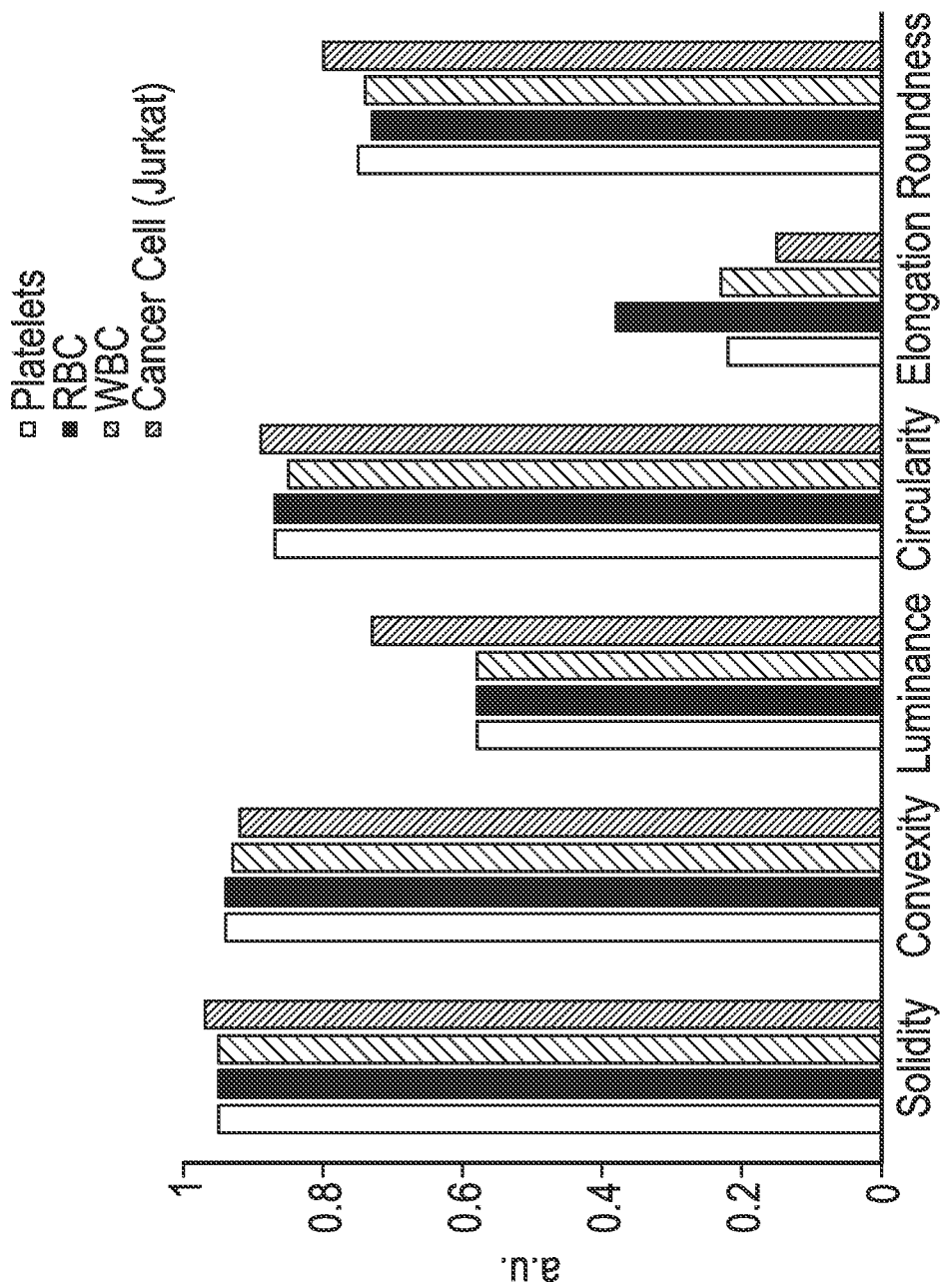
FIG. 26 is a graphical display of cell characteristics based on image data of cells.

One illustrative embodiment is a system and method for aphaeretic scanning and filtration of Leukocyte-Rich Blood Fluid to remove CTCs from a patient's circulatory system. In this example, which is illustrated in FIGS. 21 and 27, whole blood is pumped from the patient 12 into a receiver path 20 that directs flow of the whole blood to a microfluidic separation module 100, which pre-sorts whole blood using appropriate sorting techniques, e.g., Dean flow fractionation or dielectric sorting, into three components: (1) fluid containing primarily healthy erythrocytes (RBCs) and platelets, (2) fluid largely containing a mixture of leukocytes (WBCs) and small CTCs, and (3) fluid containing large CTCs and CTC-clusters. The fluid containing a mixture of leukocytes and CTCs are promoted to fluid receiving device 30 comprising a batch of parallel microfluidic channels 31. Each channel is optically scanned using DIC Microscopy, DHM, or other appropriate imaging techniques to derive a scanned data 90 of the cells for each microfluidic channel 31.

The scanned data 90 is transferred to a control unit 80, which follows an image processing software program comprising an algorithm 82 designed to recognize healthy blood cells in the scanned data 90. More particularly, the algorithm 82 is designed to recognize a pattern in a reference data 91 characteristic of healthy blood cells and process each scanned data 90 transferred to the control unit 80 to determine whether that pattern is recognized in discreet image data obtained for each cell. In the example, the reference data 91 is obtained through DIC Microscopy or DHM of blood samples taken from a representative sample of individuals other than the patient.

With reference to FIG. 29, if all cells in a scanned microfluidic channel 31 are recognized by the algorithm 82 as healthy blood cells, then the image processing software program generates a first control signal instruction 83 to the control unit 80 to relay a control signal 81 to the valve 40 to route channel contents to the return path 60. If, on the other hand, one or more of cells of the scanned microfluidic channel are not recognized by the algorithm 82, then the image processing software program generates a second control signal instruction 84 to the control unit 80 to relay a control signal to the valve 40 to route channel contents to the isolation path 50. Leukocytes routed to the return path 60 are then recombined with the pre-sorted RBCs, plasma and platelets and pumped back to the patient's circulatory system. CTC-rich fluid routed to the isolation path 50 is sequestered and optionally stored for further processing for diagnostic or therapeutic purposes.

iv. Aphaeretic Scanning and Filtration of Whole Blood Fluid with CTCs on a Microfluidic Channel Platform with Reference Image Data of Sampled Blood from Patient.

One illustrative embodiment is a system and method or aphaeretic scanning and filtration of whole blood to remove CTCs from a patient's circulatory system. As illustrated in FIGS. 12 and 28, whole blood is pumped from a patient 12 via a receiver path 20 to a fluid receiving device 30 comprising a batch of parallel microfluidic channels 31. Each channel 31 is optically scanned by a scanner 70, such as by using DIC Microscopy, DHM, or other appropriate imaging techniques, to derive a scanned data 90 of the cells for each microfluidic channel 31.

The scanned data 90 is transferred to a control unit 80, which follows an image processing software program comprising an algorithm 82 designed to recognize healthy blood cells in the scanned data 90. In the example, the reference data 91 is obtained through DIC Microscopy, DHM, or other appropriate imaging techniques of blood samples taken from the patient 12 prior to the filtration session. The algorithm 82 is designed to recognize patient-specific patterns in the reference data 91 characteristic of each type of healthy blood cell and process each scanned data 90 transferred to the control unit 80 to determine whether those patterns are recognized in discrete image data obtained for each cell.

With reference to FIG. 29, if all cells in a scanned microfluidic channel 31 are recognized by the algorithm 82 as healthy blood cells, then the image processing software program generates a first control signal instruction 83 to the control unit 80 to relay a control signal to the valve 40 to route channel contents to the return path 60 If, on the other hand, one or more of cells of the scanned microfluidic channel are not recognized by the algorithm 82, then the image processing software program generates a second control signal instruction 84 to the control unit 80 to relay a control signal to the valve 40 to route channel contents to the isolation path 50. Filtered blood in the return path 60 is pumped back to the patient's circulatory system. CTC-rich fluid routed to the isolation path 50 is sequestered and optionally stored for further processing for diagnostic or therapeutic purposes.

v. Aphaeretic Filtration of Leukocyte-Rich Blood Fluid with Small CTCs on a Microfluidic Channel Platform with Reference Image Data of Sampled Blood from Patient.

Figure 17:
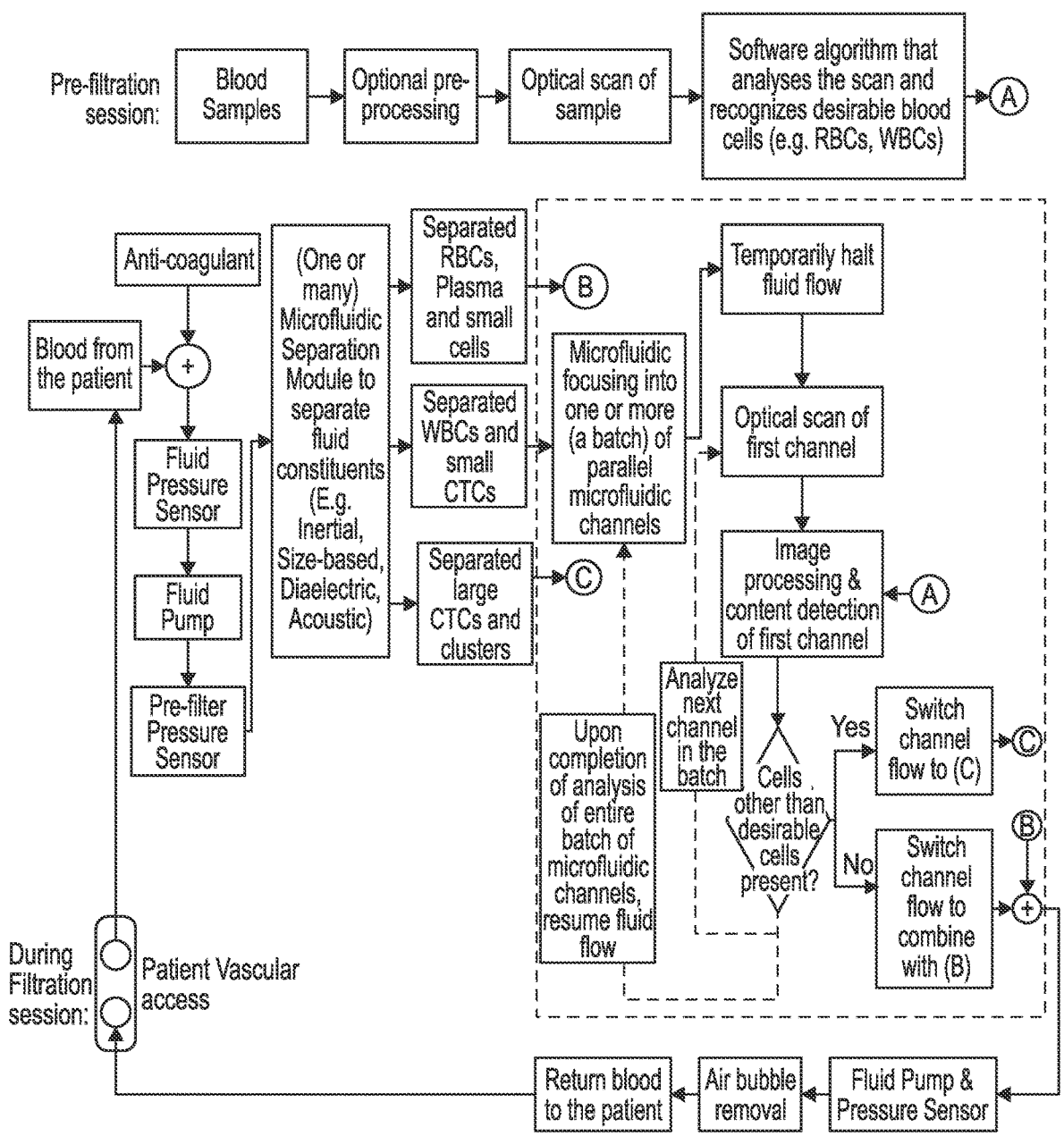
FIG. 17 is a block diagram of an aphaeretic system and method of removing undesirable CTCs from blood in accordance with an example embodiment.
Figure 18:
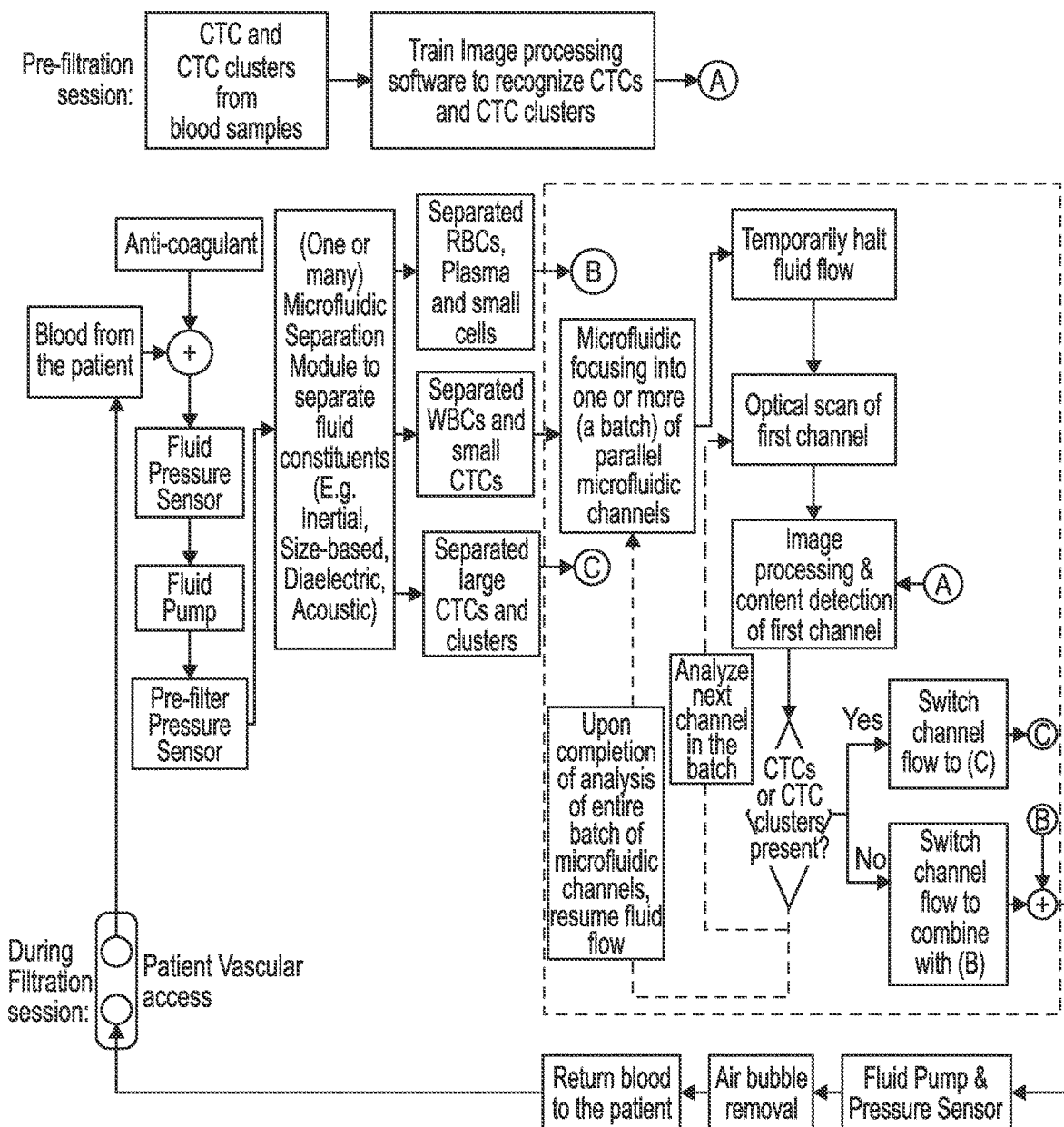
FIG. 18 is a block diagram of an aphaeretic system and method incorporating image data of CTCs and CTC-clusters into a reference data in accordance with an example embodiment.
Figure 19:
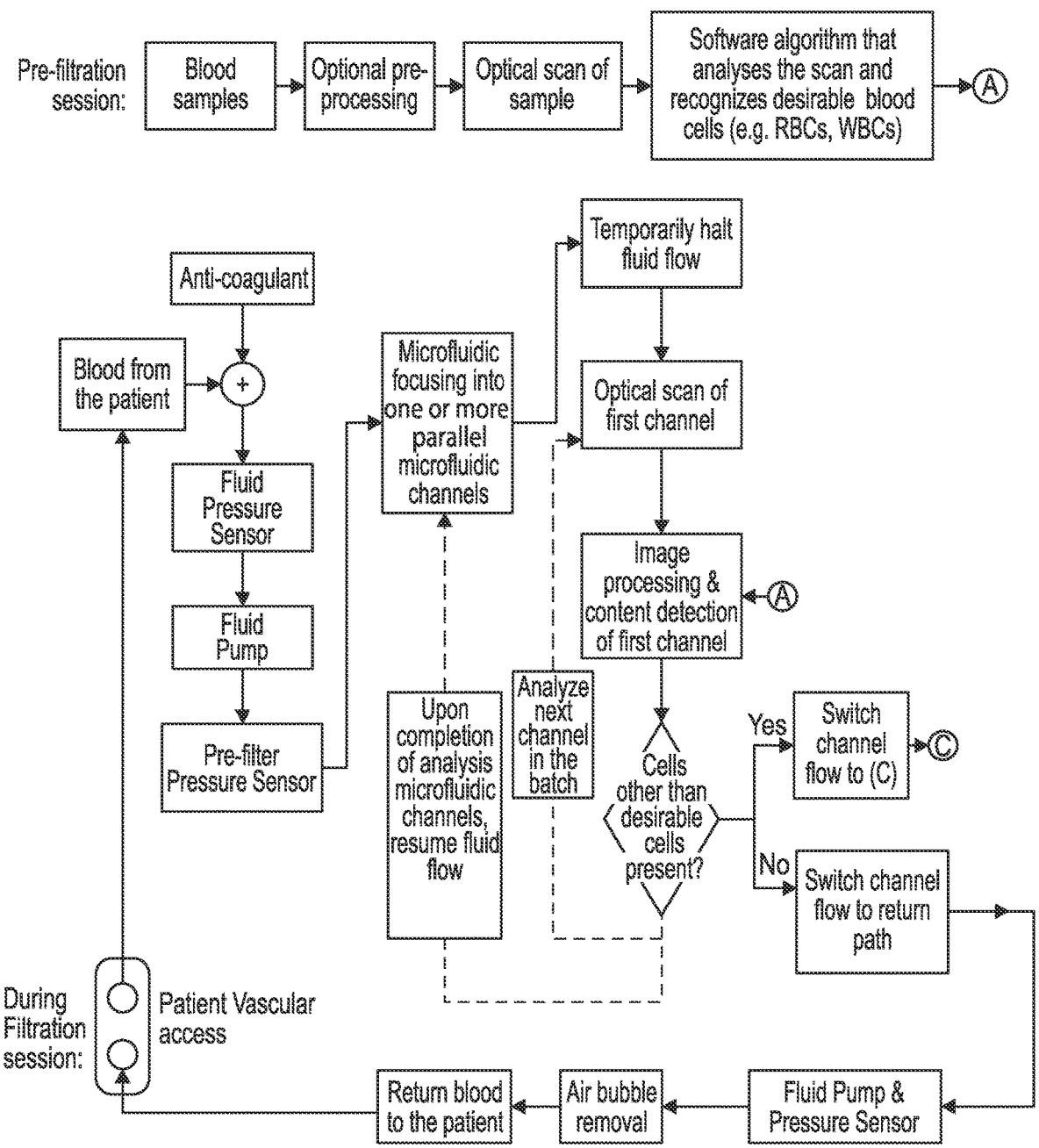
FIG. 19 is a block diagram of an aphaeretic system and method of removing undesirable CTCs from whole blood fluid in accordance with an example embodiment.

One illustrative embodiment is a system and method for aphaeretic scanning and filtration of leukocyte-rich blood fluid to remove CTCs from a patient's circulatory system. In this example, as illustrated in FIGS. 17 and 28, whole blood is pumped from the patient into a receiver path 20 that directs flow of the whole blood to a microfluidic separation module 100, which pre-sorts whole blood using appropriate sorting techniques, e.g., Dean flow fractionation or dielectric sorting, into three components: (1) fluid containing primarily healthy erythrocytes (RBCs) and platelets, (2) fluid largely containing a mixture of leukocytes (WBCs) and small CTCs, and (3) fluid containing large CTCs and CTC-clusters. The fluid containing a mixture of leukocytes and CTCs are promoted to fluid receiving device 30 comprising a batch of parallel microfluidic channels 31. Each channel is optically scanned by a scanner 70 which may, for example, use DIC Microscopy, DHM, or other appropriate imaging techniques to derive a scanned data 90 of the cells for each microfluidic channel 31.

The scanned data 90 is transferred to a control unit 80, which follows an image processing software program comprising an algorithm 82 designed to recognize healthy blood cells in the scanned data 90. In the example, a reference data 91 is obtained through DIC Microscopy, DHM, or other appropriate imaging techniques of blood samples taken from the patient prior to the filtration session. The algorithm 82 is designed to recognize a pattern in the reference data 91 characteristic of the patient's healthy cells and process each scanned data 90 transferred to the control unit 80 to determine whether that pattern is recognized in discreet image data obtained for each cell.

With reference to FIG. 29, if all cells in a scanned microfluidic channel 31 are recognized by the algorithm 82 as healthy cells, then the image processing software program generates a first control signal instruction 83 to the control unit 80 to relay a control signal 81 to the valve 40 to route channel contents to the return path 60. If, on the other hand, one or more of cells of the scanned microfluidic channel are not recognized by the algorithm 82, then the image processing software program generates a second control signal instruction 84 to the control unit 80 to relay a control signal 81 to the valve 40 to route channel contents to the isolation path 50. Leukocytes routed to the return path 60 are then recombined with the pre-sorted RBCs, plasma and platelets and pumped back to the patient's circulatory system. CTC-rich fluid routed to the isolation path 50 is sequestered and optionally stored for further processing for diagnostic or therapeutic purposes.

vi. Aphaeretic Scanning and Filtration of Whole Blood Fluid with Pathogens on a Microfluidic Channel Platform.

Figure 15:
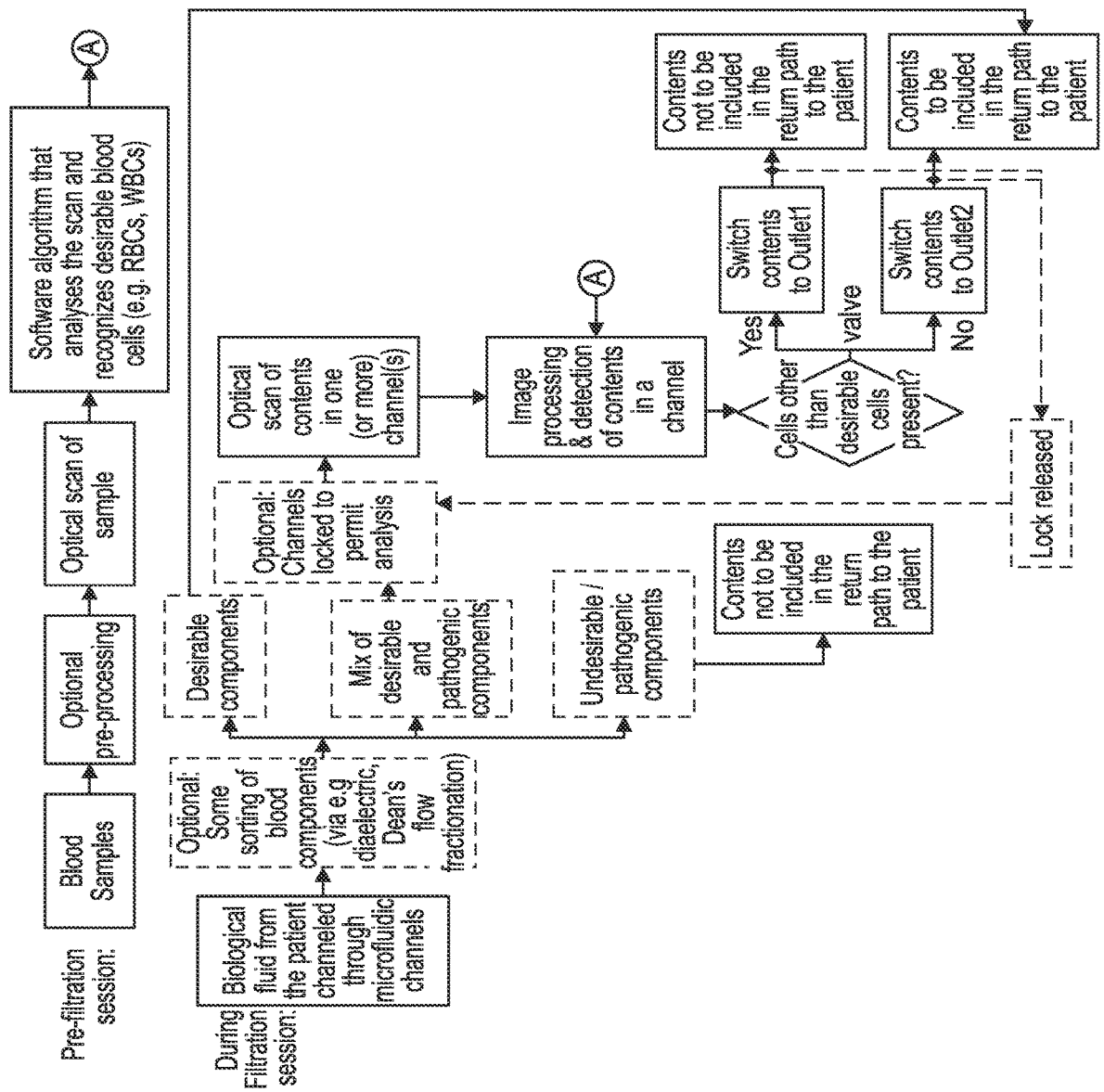
FIG. 15 is a block diagram of an aphaeretic system and method of removing undesirable pathogens from component blood fluid in accordance with an example embodiment.

An illustrative embodiment is a system and method for aphaeretic scanning and filtration of whole blood to remove pathogens from a patient's circulatory system. As shown in FIGS. 15 and 27-28, whole blood is pumped from a patient 12 via a receiver path 20 to a fluid receiving device 30 comprising a batch of parallel microfluidic channels 31. Each channel is optically scanned using DIC Microscopy, DHM, or other appropriate imaging techniques to derive a scanned data 90 of the cells for each microfluidic channel 31.

The scanned data is transferred to a control unit 80, which utilizes an image processing software program comprising an algorithm 82 designed to recognize healthy blood cells in the scanned data 90. More particularly, the algorithm 82 is designed to recognize patterns in reference image data of the reference data 91 characteristic of each type of healthy blood cell and process each scanned data 90 transferred to the control unit 80 to determine whether those patterns are recognized in discreet image data obtained for each cell. The reference data 91 is obtained through DIC Microscopy, DHM, or other appropriate imaging techniques of either samples taken from the patient's blood or samples taken from a representative sample of individuals other than the patient.

With reference to FIG. 29, if all cells in a scanned microfluidic channel 31 are recognized by the algorithm 82 as healthy blood cells, then the image processing software program generates a first control signal instruction 83 to the control unit 80 to relay a control signal 81 to the valve 40 to route channel contents to the return path 60. If, on the other hand, one or more of cells of the scanned microfluidic channel 31 are not recognized by the algorithm, then the image processing software program generates a second control signal instruction 84 to the control unit 80 to relay a control signal 81 to the valve 40 to relay a control signal to the valve 40 to route channel contents to the isolation path 50. Filtered blood in the return path 60 is pumped back to the patient's circulatory system. Pathogen-infected fluid in the isolation path 50 is sequestered and optionally stored for further processing for diagnostic or therapeutic purposes vii. Aphaeretic Filtration of Pre-Sorted Blood Fluid with Pathogens on Microfluidic Channel Platform.

An illustrative embodiment is a system and method for aphaeretic filtration of Pre-Sorted Blood Fluid to remove pathogens from a patient's circulatory system. In this example, as shown in FIGS. 15 and 27-28, whole blood is pumped from the patient 12 into a receiver path 20 that directs flow of the whole blood to a microfluidic separation module 100, which pre-sorts whole blood using appropriate sorting techniques, e.g., Dean flow fractionation or dielectric sorting, into three components: (1) fluid containing only healthy blood cells, (2) fluid containing a mixture of healthy blood cells and pathogens, and (3) fluid containing only pathogens. The fluid containing a mixture of blood cells and pathogens are promoted to a fluid receiving device 30 comprising a batch of parallel microfluidic channels 31. Each channel is optically scanned using by a scanner 70 which uses DIC Microscopy, DHM, or other appropriate imaging techniques to derive a scanned data 90 of cells for each channel.

The scanned data 90 is transferred to a control unit 80, which utilizes an recognize healthy blood cells in the scanned data 90. More particularly, the algorithm 82 is designed to recognize a patterns in a reference data 91 characteristic of each type of healthy blood cell and process each scanned data 90 transferred to the control unit to determine whether that pattern is recognized in discreet image data obtained for each cell. The scanned data 90 may be obtained through DIC Microscopy, DHM, or other appropriate imaging techniques of either samples taken from the patient's blood or samples taken from a representative sample of individuals other than the patient.

With reference to FIG. 29, if all cells in a scanned microfluidic channel 31 are recognized by the algorithm as healthy blood cells, then the image processing software program generates a first control signal instruction 83 to the control unit 80 to relay a control signal 81 to a valve 40 to route the channel's contents to the return path 60. If, on the other hand, one or more of cells of the scanned channel 31 are not recognized by the algorithm 82, then the image processing software program generates a second control signal instruction 84 to the control unit 80 to relay a control signal 81 to the valve 40 to route the channel's contents to the isolation path 50. Blood cells routed to the return path 60 are then recombined with the pre-sorted healthy blood cells and pumped back to the patient's circulatory system. Pathogen-infected fluid routed to the isolation path 50, along with the pre-sorted fluid containing only pathogens, are sequestered and optionally stored for further processing for diagnostic or therapeutic purposes.

viii. Aphaeretic Scanning and Filtration of Whole Blood Fluid with CTCs on a Microwell Array.

An illustrative embodiment is a system and method for aphaeretic scanning and filtration of whole blood to remove CTCs from a patient's circulatory system using a microwell array 32. As shown in FIGS. 8-11, and 27-28, whole blood is pumped from a patient 12 via a receiver path 20 to a fluid receiving device 30 comprising a microwell array 32. Each microwell of the microwell array 32 is optically scanned with a scanner 70 using DIC Microscopy, DHM, or other appropriate imaging techniques to derive a scanned data 90 of the cells for each microwell of the microwell array 32. Micro-wells may be periodically disrupted, such as by shaking or stirring, and multiple scans taken, to ensure that the scanned data 90 captures the entirety of the contents of the microwells.

The scanned data 90 is transferred to a control unit 80, which utilizes an image processing software program comprising an algorithm 82 designed to recognize healthy blood cells in the scanned data 90. More particularly, the algorithm is designed to recognize patterns in reference image data of the reference data 91 characteristic of each type of healthy blood cell and process each scanned data 90 transferred to the control unit 80 to determine whether those patterns are recognized in discreet image data from the reference data 91 obtained for each cell. The reference data 91 is obtained through DIC Microscopy, DHM, or other appropriate imaging techniques of blood samples taken from either from a sample of blood from the patient 12 or a representative sample of individuals other than the patient 12.

With reference to FIG. 29, if all cells in a scanned microwell of the microwell array 32 are recognized by the algorithm as healthy blood cells, then the image processing software program generates a first control signal instruction 83 to the control unit 80 to relay a control signal 81 to the valve 40 at the base of the microwell to route the contents of the microwell to the return path 60 If, on the other hand, one or more of cells of the scanned microwell are not recognized by the algorithm, then the image processing software program generates a second control signal instruction 84 to the control unit 80 to relay a control signal 81 to the valve 40 to route the contents of the microwell to the isolation path 50. Filtered blood in the return path 60 is pumped back to the patient's circulatory system. CTC-rich fluid routed to the isolation path 50 is sequestered and optionally stored for further processing for diagnostic or therapeutic purposes. In some example embodiments, pipettes could be utilized to extract contents of a microwell. In other embodiments, multiple wells in an array could share a single valve 40.

ix. Aphaeretic Filtration of Leukocyte-Rich Blood Fluid with Small CTCs on a Microwell Array.

An illustrative embodiment is a system and method for aphaeretic scanning and filtration of leukocyte-rich blood fluid to remove CTCs from a patient's circulatory system using a microwell array 32. With reference to FIGS. 8-10 and 27-28, whole blood is pumped from the patient 12 into a receiver path 20 that directs flow of the whole blood to a microfluidic separation module 100, which pre-sorts whole blood using appropriate sorting techniques, e.g., Dean flow fractionation or dielectric sorting, into three components: (1) fluid containing only healthy erythrocytes (RBCs) and platelets, (2) fluid largely containing a mixture of leukocytes (WBCs) and small CTCs, and (3) fluid containing large CTCs and CTC-clusters. The fluid containing a mixture of leukocytes and CTCs are promoted to a fluid receiving device 30 comprising a microwell array 32. Each microwell is optically scanned by a scanner 70, which may use DIC Microscopy, DHM, or other appropriate imaging techniques to derive a scanned data 90 of the cells for each microwell.

The scanned data 90 is transferred to a control unit 80, which utilizes an image processing software program comprising an algorithm 82 designed to recognize healthy blood cells in the scanned data 90. More particularly, the algorithm 82 is designed to recognize a pattern in a reference data 91 characteristic of healthy blood cells and process each scanned data 90 transferred to the control unit 80 to determine whether that pattern is recognized in discreet image data obtained for each cell. The reference data 91 is obtained through DIC Microscopy of a sample of the patient's blood or blood samples taken from a representative sample of individuals other than the patient 12.

With reference to FIG. 29, if all cells in a scanned microwell are recognized by the algorithm 82 as healthy blood cells, then the image processing software program generates a first control signal instruction 83 to the control unit 80 to relay a control signal 81 to the valve 40 to route the contents of the microwell to the return path 60. If, on the other hand, one or more of cells of the scanned microwell are not recognized by the algorithm 82, then the image processing software program generates a second control signal instruction 84 to the control unit 80 to relay a control signal 81 to the valve 40 to route the contents of the microwell to isolation path 50. Leukocytes routed to the return path 60 are then recombined with the pre-sorted RBCs, plasma and platelets and pumped back to the patient's circulatory system. CTC-rich fluid routed to the isolation path 50 is sequestered and optionally stored for further processing for diagnostic or therapeutic purposes. In some example embodiments, pipettes could be utilized to extract contents of a microwell. In other embodiments, multiple wells in an array could share a single valve 40.

x. Aphaeretic Filtration of Leukocyte-Rich Blood Fluid with Small CTCs on a Microfluidic Channel Platform with Reference Image Data for CTCs.

Figure 20:
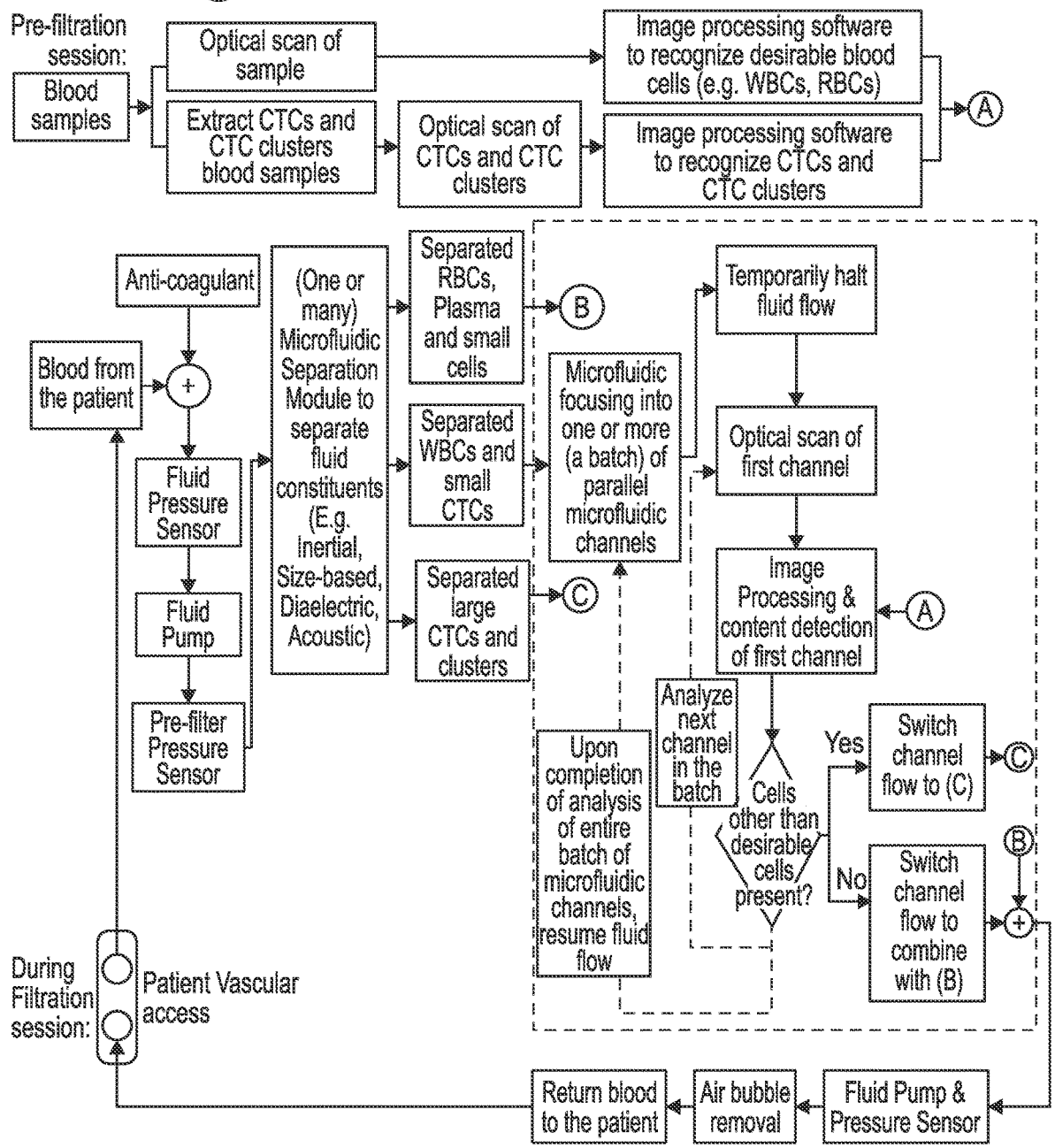
FIG. 20 is a block diagram of an aphaeretic system and method of incorporating image data of CTCs and CTC-clusters into a reference data in accordance with an example embodiment.

An illustrative embodiment is a system and method for aphaeretic scanning and filtration of Leukocyte-Rich Blood Fluid to remove CTCs from a patient's circulatory system using reference data 91 of healthy blood cells and CTCs. With reference to FIG. 20, a biological fluid 16 comprised of whole blood is pumped from the patient 12 into a receiver path 20 that directs flow of the whole blood to a microfluidic separation module 100, which pre-sorts whole blood using appropriate sorting techniques, e.g., Dean flow fractionation or dielectric sorting, into three components: (1) fluid containing only healthy erythrocytes (RBCs) and platelets, (2) fluid largely containing a mixture of leukocytes (WBCs) and small CTCs, and (3) fluid containing large CTCs and CTC-clusters. The fluid 16 containing a mixture of leukocytes and CTCs are promoted to a fluid receiving device 30 comprising a batch of parallel microfluidic channels 31. Each channel 31 is optically scanned with a scanner 70 using DIC Microscopy, DHM, or other appropriate imaging techniques to derive a scanned data 90 of the cells for each microfluidic channel 31.

The scanned data 90 is transferred to a control unit 80, which utilizes an recognize healthy blood cells and CTCs in the scanned data 90. More particularly, the algorithm 82 is designed to recognize a pattern in a reference data 91 characteristic of healthy blood cells and CTCs and process each scanned data 90 transferred to the control unit 80 to determine whether that pattern is recognized in discreet image data obtained for each cell. The reference data 91, including image data of recognized CTCs, is obtained through DIC Microscopy, DHM, or other methods of blood samples containing CTCs taken from either from a sample of blood from the patient or a representative sample of individuals other than the patient. Image data from the reference data 91 may also include scanned images of CTCs appropriately cultured in medium or other fluids.

With reference to FIG. 29, if all cells in a scanned microwell are recognized by the algorithm 82 as all healthy blood cells, then the image processing software program generates a first control signal instruction 83 to the control unit 80 to relay a control signal 81 to the valve 40 to route the contents of the channel to the return path 60. If, on the other hand, one or more of cells of the scanned microwell are recognized as CTCs or not recognized by the algorithm 82, then the image processing software program generates a second control signal instruction 84 to the control unit 80 to relay a control signal 81 to valve 40 to route the contents of the channel to isolation path 50. Leukocytes routed to the return path 60 are then recombined with the pre-sorted RBCs, plasma and platelets and pumped back to the patient's circulatory system. CTC-rich fluid routed to the isolation path 50 is sequestered and optionally stored for further processing for diagnostic or therapeutic purposes.

xi. Aphaeretic Scanning and Filtration of Whole Blood Fluid with CTCs on a Microfluidic Channel Platform with Reference Image Data for CTCs for Validation.

An illustrative embodiment is a system and method for aphaeretic scanning and filtration of whole blood to remove CTCs from a patient's 12 circulatory system using reference image data from a reference data 91 for both healthy blood cells and CTCs. With reference to FIG. 20, whole blood is pumped from a patient 12 via a receiver path 20 to a fluid receiving device 30 comprising a batch of parallel microfluidic channels 31. Each channel is optically scanned by a scanner using DIC Microscopy, DHM, or other appropriate imaging techniques to derive a scanned data 90 of the cells for each microfluidic channel 31.

The scanned data 90 is transferred to a control unit 80, which utilizes an image processing software program comprising an algorithm 82 designed to recognize healthy blood cells in the scanned data 90 and a certifying algorithm 85 designed to recognize CTCs in the scanned data 90. In the example, a reference data 91 is obtained through DIC Microscopy, DHM, or other appropriate imaging techniques of a sample of blood samples containing CTCs taken from either from a sample of blood from the patient 12 or a representative sample of individuals other than the patient 12. Image data of the reference data 91 may also include scanned images of CTCs appropriately cultured in medium or other fluids.

With reference to FIG. 29, the algorithm 82 is designed to recognize patterns in the reference data 91 characteristic of CTCs and each type of healthy blood cell and process each scanned data 90 transferred to the control unit 80 to determine whether those patterns are recognized in discreet image data obtained for each cell and generate one of two control signal instruction to the control unit: a first control signal instruction 83 routing the channel's contents to the return path 60 if every cell in the channel is recognized as a healthy blood cell, and a second control instruction 84 routing the channel's contends determined to contain CTCs to the isolation path 50 if one or more cells in the channel is not recognized as a healthy blood cell.

The certifying algorithm 85 is designed to generate a certification output before a first control instruction 83 can be executed by the control unit 80. The certifying algorithm 85 is designed to recognize a pattern in the reference data 91 characteristic of the CTCs and verify that the CTC pattern is not recognized in the scanned data 90 on which a generated first control signal instruction 83 is based. If the verification condition is met, the certifying algorithm 85 generates a certification output and the control unit 80 is given a go instruction to execute the first control signal instruction 83. If the verification condition is not met, the certifying algorithm 85 generates an error output, prompting the image processing software program to replace the first control signal instruction 83 with a second control signal instruction 84 executed by the control unit 80. Filtered blood in return path is pumped back to the patient's circulatory system.

CTC-rich fluid routed to the isolation path 50 is sequestered and may optionally be further processed for diagnostic or therapeutic purposes.

In some embodiments, the biological fluid 16 within the fluid receiving device 30 may be scanned multiple times to verify that the biological fluid 16 within the fluid receiving device 30 is indeed healthy prior to returning to the biological fluid source 17 via the return path 60. In such an embodiment, after an initial scan of the biological fluid 16 by the scanner 70 fails to detect any undesirable constituents 14, the biological fluid 16 will be re-scanned, either by the same scanner 70 or by a different scanner 70 in embodiments with multiple scanners 70, to verify and confirm the absence of any undesirable constituents 14 within the biological fluid 16. The number of times that the biological fluid 16 is scanned in such a verification algorithm may vary in different embodiments.

xii. Aphaeretic Filtration of Leukocyte-Rich Blood Fluid with Small CTCs on a Microfluidic Channel Platform with Reference Image Data for CTCs for Validation.

An illustrative embodiment is a system and method for aphaeretic scanning and filtration of Leukocyte-Rich Blood Fluid to remove CTCs from a patient's circulatory system using reference image data from a reference data 91 of healthy blood cells and CTCs. With reference to FIGS. 20 and 27-28, biological fluid 16 comprised of whole blood is pumped from the patient 12 into a receiver path 20 that directs flow of the whole blood to a microfluidic separation module 100, which pre-sorts whole blood using appropriate sorting techniques, e.g., Dean flow fractionation or dielectric sorting, into three components: (1) fluid containing primarily healthy erythrocytes (RBCs) and platelets, (2) fluid largely containing a mixture of leukocytes (WBCs) and small CTCs, and (3) fluid containing large CTCs and CTC-clusters. The fluid containing a mixture of leukocytes and CTCs are promoted to a fluid receiving device 30 comprising a batch of parallel microfluidic channels 31. Each channel is optically scanned by a scanner 70 using DIC Microscopy, DHM, or other appropriate imaging techniques to derive a scanned data 90 of the cells for each microfluidic channel 31.

The scanned data 90 is transferred to a control unit 80, which utilizes an recognize healthy blood cells in the scanned data 90 and a certifying algorithm 85 designed to recognize CTCs in the scanned data 90. In the example, a reference data 91 is obtained through DIC Microscopy, DHM, or other appropriate imaging techniques of blood samples containing CTCs taken from either from a sample of blood from the patient 12 or a representative sample of individuals other than the patient 12. The reference data 91 may also include scanned images of CTCs appropriately cultured in medium or other fluids.

With reference to FIG. 29, the algorithm 82 is designed to recognize patterns in the reference data 91 characteristic of healthy blood cells and process each scanned data 90 transferred to the control unit 80 to determine whether those patterns are recognized in discreet image data obtained for each cell and generate one of two control signal instruction to the control unit: a first control signal instruction 83 to route channel contents to the return path 60 if every cell in the channel is recognized as healthy blood cell, and a second control instruction 84 to route channel contends determined to contain CTCs to the isolation path 50 if one or more cells in the channel is not recognized as a healthy blood cell. The certifying algorithm 85 is designed to generate a certification output before a first control instruction can be executed by the control unit 80.

The certifying algorithm 85 is designed to recognize a pattern in the reference data 91 characteristic of CTCs and verify that the CTC pattern is not recognized in a scanned data 90 on which a generated first control signal instruction 83 is based. If the verification condition is met, the certifying algorithm 85 generates a certification output and the control unit 80 is given a go instruction to execute the first control signal instruction 83. If the verification condition is not met, the certifying algorithm generates an error output, prompting the image processing software program to replace the first control signal instruction 83 with a second control signal instruction 84 executed by the control unit 80. Filtered blood in return path is pumped back to the patient's circulatory system. CTC-rich fluid routed to the isolation path 50 is sequestered and may optionally be further processed for diagnostic or therapeutic purposes.

In some embodiments, the biological fluid 16 within the fluid receiving device 30 may be scanned multiple times to verify that the biological fluid 16 within the fluid receiving device 30 is indeed healthy prior to returning to the biological fluid source 17 via the return path 60. In such an embodiment, after an initial scan of the biological fluid 16 by the scanner 70 fails to detect any undesirable constituents 14, the biological fluid 16 will be re-scanned, either by the same scanner 70 or by a different scanner 70 in embodiments with multiple scanners 70, to verify and confirm the absence of any undesirable constituents 14 within the biological fluid 16. The number of times that the biological fluid 16 is scanned in such a verification algorithm may vary in different embodiments.

xiii. Aphaeretic Scanning and Filtration of Blood with CTCs on a Microfluidic Channel Platform Including Reference Image Data to Limit False Positives.

An illustrative embodiment is a system and method for aphaeretic scanning and filtration of blood fluid to remove undesirable CTCs or pathogens from a patient's circulatory system using reference image data that includes recognized patterns for optic artifacts and designated pathogens not intended for filtration to limit erroneous second control signal instructions 84 based on false positives.

In the example, as shown in FIGS. 16 and 27-28, reference data 91 for healthy blood cells is obtained through DIC Microscopy, DHM, or other appropriate imaging techniques, as described herein. The reference data 91 also includes image data of known optic artifacts and scanned data 90 of known non-target blood borne pathogens. The image processing software program of the control unit 80 of this embodiment comprises an algorithm 82 designed to recognize patterns in the reference data 91 characteristic of each type of healthy blood cell and to recognize data patterns of optic artifacts and designated pathogens in reference data 91 to avoid interpreting these data patterns as undesirable CTCs.

In operation, blood fluid on the fluid receiving device 30 is optically scanned, as described herein, to obtain a scanned data 90 of the cells in the scanned biological fluid 16. The scanned data 90 is transferred to the control unit 80, and the algorithm 82 processes the scanned data 90 to determine whether patterns for healthy blood cells, optic artifacts, and designated pathogens in the 19 reference data 91 is recognized in discreet image data of the scanned data 90 for each cell. As with other embodiments, the image processing software program generates a first control signal instruction 83 if all cells are recognized by the algorithm 82, or a second control signal instruction 84 if one or more cells is not recognized. Because recognized pattern data of optic artifacts and designated pathogens is incorporated into the reference data 91, the presence of optic artifacts in the scanned data 90 or of non-target pathogens in the scanned biological fluid will not cause algorithm 82 to trigger the second control signal instruction 84.

It is preferable to maximize the amount of healthy blood cells returned to the patient 12 and, relatedly, to limit the amount of healthy blood cells lost during filtration. The biological fluid filtration system 10 operates most efficiently when scanned cells routed to the return path based on a first control signal instruction 83 are all healthy blood cells and when scanned cells routed to the isolation path 50 based on a first control signal instruction 83 comprise at least one undesirable CTC that triggered the instruction. Image data from optical artifacts or blood borne pathogens are often picked up by optic scans, and so have the potential to trigger a first control signal instruction 83. The present embodiment mitigates this issue by adding image data from optical artifacts or designated pathogens to the reference data 91 recognized algorithm 82.

xiv. Diagnostic System and Methods.

As shown throughout the figures and discussed herein, the systems and methods described herein may be utilized for various diagnostic purposes. For example, undesirable constituents 14 may be sequestered and subject to a variety of in vitro diagnostic tools for purposes of identification, prognosis, and/or treatment determinations, within a number of methodological categories, including microscopy, immunology-based assaying, culturing, in vitro testing, drug sensitivity and resistance testing, and genomic testing.

xv. Scanning and Filtration of Blood Sample for Diagnosis of a Pathogenic Infection.

FIG. 14 is a block diagram of a diagnostic system and method of an embodiment adapted to remove undesirable, indeterminate pathogens from a biological fluid 16 and processing the removed pathogens for diagnostics.

In the example, a blood sample is loaded into the fluid receiving device 30, which comprises a batch of parallel microfluidic channels 31 adapted to receive the blood sample. Each channel 31 is optically scanned by a scanner 70 using DIC Microscopy, DHM, or other appropriate imaging techniques to derive a scanned data 90 of the cells for each microfluidic channel 31.

The scanned data 90 is transferred to a control unit 80 which follows an image processing software program comprising an algorithm 82 designed to recognize healthy blood cells in the scanned data 90. In the example, reference data 91 is obtained through DIC Microscopy, DHM, or other appropriate imaging techniques of blood samples taken from the patient 12 or from a representative sample of individuals other than the patient 12 prior to the diagnostic session. The algorithm 82 is designed to recognize a pattern in the reference data 91 and process each scanned data 90 transferred to the control unit 80 to determine whether that pattern is recognized in discreet image data from the scanned data 90 obtained for each cell.

If all cells in a scanned microfluidic channel 31 are recognized by the algorithm 82 as healthy blood cells, the control unit 80 causes the valve 40 to direct contents of the channel 31 for disposal. If, on the other one or more of cells of the scanned microfluidic channel 31 are not recognized by the algorithm 82, the control unit 80 causes the valve 40 to direct the fluid 16 for collection and diagnostic processing.

The control unit 80 is also adapted collect and store catalogued image data for a group of catalogued pathogens, and the algorithm 82 is further adapted to recognize patterns in the reference data 91 characteristic of catalogued pathogens, and process a scanned data 90 to search those patterns in the scanned data 90, and identify any catalogued pathogen whose pattern is recognized in the scanned data 90. The control unit 80 is further adapted to store scanned data 90 to the catalogued image data, assign the scan image data to a catalogued pathogen whose pattern is recognized in the scan image data or to a pathogen later identified in further diagnostic procedures, and the algorithm 82 is further adapted to recognize the scanned data 90 for use in connection in with diagnostic procedures.

xvi. Scanning and Filtration of Blood Sample for Diagnosis of a Cancer.

FIG. 14 also illustrates an embodiment diagnostic system and method adapted to remove undesirable indeterminate CTCs or CTC-clusters from a biological fluid 16 and process the removed CTCs or CTC-clusters for diagnostics. Such an embodiment could be utilized to detect the presence of cancer in an individual.

In the example, a blood sample is loaded into the fluid receiving device 30, which comprises a batch of parallel microfluidic channels 31 adapted to receive the blood sample. Each channel 31 is optically scanned by a scanner 70 using DIC Microscopy, DHM, or other appropriate imaging techniques to derive a scanned data 90 of the cells for each microfluidic channel 31.

The scanned data 90 is transferred to a control unit 80 which utilizes an image processing software program comprising an algorithm 82 designed to recognize healthy blood cells in the scanned data 90. In the example, a reference data 91 is obtained through DIC Microscopy, DHM, or other appropriate imaging techniques of blood samples taken from the patient 12 or from a representative sample of individuals other than the patient 12 prior to the diagnostic session. The algorithm 82 is designed to recognize a pattern in the reference data 91 characteristic of healthy blood cells and process each scanned data 90 transferred to the control unit 80 to determine whether that pattern is recognized in discreet image data from the scanned data 90 obtained from each cell.

If all cells in a scanned microfluidic channel 31 are recognized by the algorithm 82 as healthy blood cells, the control unit 80 causes the valve 40 to direct contents of the channel 31 for disposal. If, on the other hand, one or more of cells of the scanned microfluidic channel 31 are not recognized by the algorithm 82, the control unit 80 causes the valve 40 to direct the fluid 16 for collection and diagnostic processing.

The control unit 80 is also adapted collect and store catalogued image data for a group of catalogued CTCs, and the algorithm 82 is further adapted to recognize patterns in the reference data 91 characteristic of catalogued CTCs, and process a scanned data 90 to search those patterns in the scanned data 90, and identify any catalogued CTCs whose pattern is recognized in the scanned data 90. The control unit 80 is further adapted to store scan image data to the scanned data 90, assign the scanned data 90 to a catalogued CTC whose pattern is recognized in the scanned data 90 or to a CTC identified in further diagnostic procedures, e.g., PCR, and the algorithm 82 is further adapted to recognize the scanned data 90 for use in connection with diagnostic procedures.

xvii. Scanning and Filtration of Leukapheresis Extract.

FIG. 32 illustrates an exemplary embodiment of scanning and filtering a 7 leukapheresis extract from a patient 12 undergoing leukapheresis. As shown in FIG. 32, biological fluid 16 comprised of a leukapheresis extract from the patient 12 containing healthy cells and tumor cells is extracted from the patient 12. The leukapheresis extract may be presorted using a microfluidic separation module 100 in which healthy cells (e.g., utilizing RBC lysis, microfluidic sorting, etc.) are separated from the leukapheresis extract.

The remaining sample of the leukapheresis extract after presorting is directed into a fluid receiving device 30 (e.g., microfluidic channels 31, microwell arrays 32, and/or droplet generators 34) and then scanned by the scanner 70. The scanned data 90 from the scanner 70 is transferred to the control unit 80 which, utilizing a reference data 91, detects the contents of the leukapheresis extract.

If cells other than healthy cells are detected within the scanned leukapheresis extract sample, the sample may be optionally returned by a reprocessing path 62 for further enrichment of non-healthy cells. Such samples may also be processed for diagnostics. If only healthy cells are detected within the scanned leukapheresis extract sample, the sample may be directed along an isolation path 50 and not be processed for diagnostics.

FIG. 37 illustrates another exemplary method of scanning and filtering a leukapheresis extract. As shown in FIG. 37, the presorting stage comprised of a microfluidic separation module 100 may be utilized for optional red blood cell and platelet separation using microfluidic or biochemical methods. After scanning by the scanner 70 on the fluid receiving device 30, any samples containing unrecognized cells may be processed for extraction of such unrecognized cells (e.g., T-cell extraction) and may optionally be reprocessed by redirecting back to the fluid receiving device 30 via a reprocessing path 62. Any samples containing only recognized healthy cells may be directed along an isolation path 50 not to be processed for cell extraction.

xviii. Scanning and Filtration of Stem Cell Extract.

FIG. 33 illustrates an exemplary embodiment of scanning and filtering a stem cell extract from a patient 12 undergoing procedures for removal of stem cells. As shown in FIG. 33, biological fluid 16 comprised of a stem cell extract is extracted from the patient 12 containing healthy cells and any tumor cells. The stem cell extract may optionally be directed to a microfluidic separation module 100 for separation of red blood cells and platelets using microfluidic or biochemical methods.

The remaining stem cell extract after the optional presorting stage is directed to the fluid receiving device 30 in which it is optically scanned by a scanner 70. The scanned data 90 from the scanner 70 is transferred to the control unit 80 which, utilizing a reference data 91, detects the contents of the stem cell extract.

If cells other than healthy cells (e.g., tumor cells, pathogens, etc.) are detected in the stem cell extract sample, the sample may be optionally directed along a reprocessing path 62 for optional reprocessing for further enrichment of non-healthy cells. Any such stem cell extract samples (whether further enriched or not) may then be processed for diagnostics. Stem cell extract samples containing only healthy cells (e.g., not including tumor cells or pathogens) may be directed along an isolation path 50 to be utilized for stem cell transplant.

xix. Scanning and Filtration of Dialyzed Blood.

Figure 51:
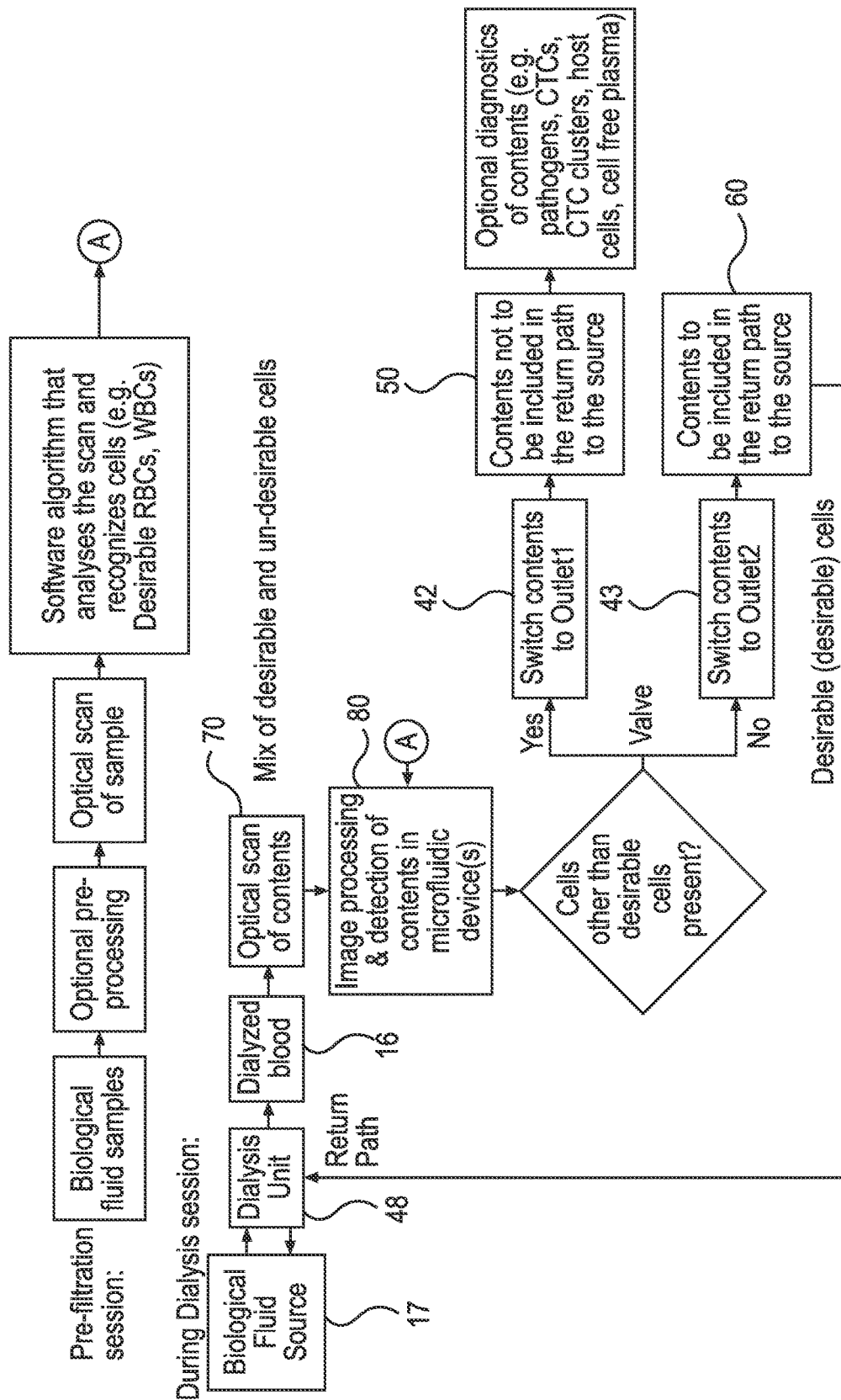
FIG. 51 is a block diagram illustrating a biological fluid filtration system being connected to a dialysis unit in accordance with an example embodiment.

12 FIG. 51 illustrates an exemplary embodiment of scanning and filtering dialyzed blood from a dialysis unit 48. In such an embodiment, the optical filtration unit is connected to a dialysis unit 48 (i.e., a dialysis machine), where blood (either pre- or post-dialysis) is sent to the optical filtration unit and healthy blood is returned back to the dialysis unit 48.

As shown in FIG. 51, biological fluid 16 from the biological fluid source 17 is first undergoes dialysis within a dialysis unit 48. The resulting biological fluid 16 which has undergone dialysis (e.g., dialyzed blood) is then transferred to a fluid receiving device 30 and optically scanned by a scanner 70. The resulting scanned data 90 is processed by the control unit 80. If only desirable constituents 15 are detected, the sample may be returned back to the dialysis unit 48 by a return path 60. If undesirable constituents 14 are detected, the sample may be isolated along an isolation path 50 and are not returned to the dialysis unit 48. Optionally, diagnostics may be performed on the contents (e.g., pathogens, CTCs, CTC-clusters, host cells, cell free plasma, etc.) that have been isolated.

xx. Scanning and Filtration of Blood Bag Contents.

Figure 52:
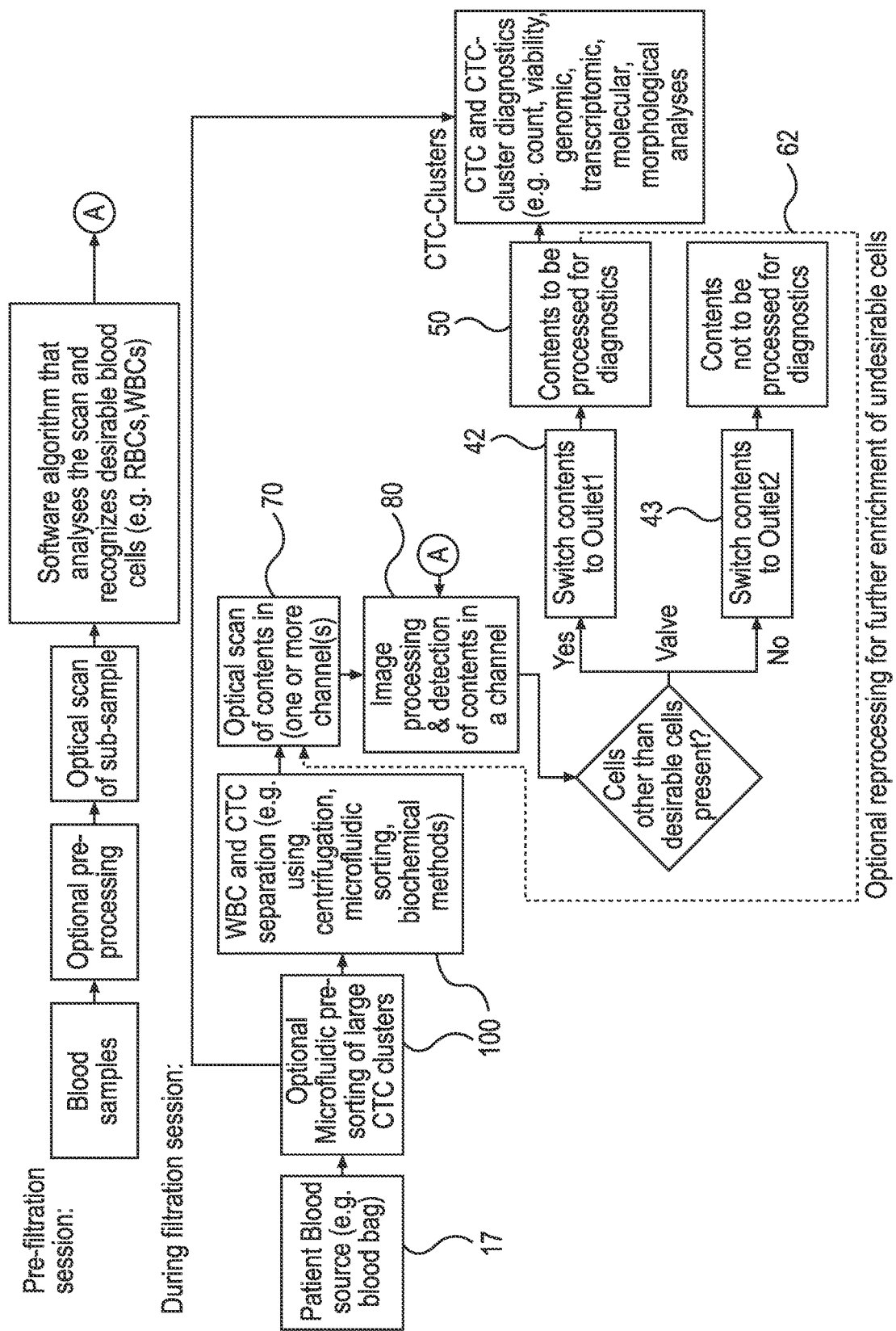
FIG. 52 is a block diagram illustrating a biological fluid filtration system being connected to a blood bag in accordance with an example embodiment.

FIG. 52 illustrates an exemplary embodiment of scanning a biological fluid 16 comprised of blood from a biological fluid source 17 comprised of a blood bag. In such an embodiment, the contents of a blood bag from a patient 12 are processed to filter CTCs and CTC-clusters. The remaining contents may then be separated using a variety of methods (e.g., microfluidic, centrifugation, biochemical, etc.) to separate white blood cells and CTCs. Those cells may then be processed via optofluidic filtration techniques described herein to separate CTCs.

As shown in FIG. 52, a biological fluid source 17 comprised of a blood bag may be utilized. The biological fluids 16 within the blood bag may be transferred to a microfluidic separation module 100 for presorting of large CTC-clusters. Any such separated large CTC-clusters may be transferred along an isolation path 50 for diagnostics (e.g., count, viability, genomic, transcriptomic, molecular, morphological analyses).

The microfluidic separation module 100 may also separate white blood cells and CTCs by using various methods such as centrifugation, microfluidic sorting, biochemical methods, etc.). Other methods such as RBC-lysis could also be used to separate red blood cells from the blood. Additional buffers or reagents could also be utilized in the presorting process. The resulting presorted contents are then transferred to a fluid receiving device 30 to be optically scanned by a scanner 70. The resulting scanned data 90 is processed by the control unit 80 for detection and identification of the contents of the biological fluid 16.

Any samples including undesirable constituents 14 may be transferred along a reprocessing path 62 to be reprocessed or may be isolated along an isolation path for CTC and CTC-cluster diagnostics (e.g., count, viability, genomic, transcriptomic, molecular, morphological analyses). Any samples which include only desirable constituents 15 may be isolated separately and not processed for diagnostics.

N. EXAMPLE EMBODIMENTS

An example embodiment of a biological fluid filtration system 10 may comprise a receiver path 20 adapted to receive a biological fluid 16 from a biological fluid source 17. A fluid receiving device 30 is fluidly connected to the receiver path 20 so as to receive the biological fluid 16 from the receiver path 20.

A valve 40 may comprise an inlet 41 and a first outlet 42, wherein the inlet 41 of the valve 40 is fluidly connected to the fluid receiving device 30. An isolation path 50 may comprise an inlet end, wherein the inlet end of the isolation path 50 is connected to the first outlet 42 of the valve 40. A scanner 70 may be oriented toward the fluid receiving device 30, with the scanner 70 being adapted to optically scan constituents 13 of the biological fluid 16 within the fluid receiving device 30 so as to derive a scanned data 90 of the constituents 13. A control unit 80 may be communicatively connected to the scanner 70 so as to receive the scanned data 90 from the scanner 70, wherein the control unit 80 is operatively connected to the valve 40.

The control unit 80 is adapted to compare the scanned data 90 to a reference data 91. The reference data 91 may comprise images and/or characteristics of desirable constituents 15 such as healthy cells. The control unit 80 is adapted to switch the valve 40 so as to direct the biological fluid 16 to the biological fluid source 17 by a return path 60 if the scanned data 90 includes only desirable constituents 15 meeting the criteria of desirable constituents 15. The control unit 80 is adapted to switch the valve 40 so as to direct the biological fluid 16 to the isolation path 50 if the scanned data 90 of the biological fluid 16 includes one or more undesirable constituents 14 not meeting the criteria of desirable constituents 15. In another exemplary embodiment of a biological fluid filtration system 10, the reference data 91 includes image data representative of desirable constituents 15.

In another exemplary embodiment of a biological fluid filtration system 10, the reference data 91 further comprises criteria of optic artifacts, and the control unit 80 is adapted to switch the valve 40 so as to direct the biological fluid 16 to the biological fluid source 17 by the return path 60 if the scanned data 90 of the biological fluid 16 includes only desirable constituents 15 meeting the criteria of optic artifacts or the criteria of desirable constituents 15.

In another exemplary embodiment of a biological fluid filtration system 10, the reference data 91 further comprises recognized criteria of designated pathogens. The control unit 80 is adapted to switch the valve 40 so as to direct the biological fluid 16 to the biological fluid source 17 by the return path 60 if the scanned data 90 of the biological fluid 16 includes only desirable constituents 15 meeting the criteria of designated pathogens or the criteria of desirable constituents 15.

The reference data 91 may include image data and/or characteristics representative of healthy blood constituents. The reference data 91 may include image data and/or characteristics representative of erythrocytes, leukocytes, thrombocytes, and the like.

In another exemplary embodiment, the biological fluid filtration system 10, comprises a microfluidic separation module 100, wherein the microfluidic separation module 100 is adapted to receive blood from the receiver path 20, generate a primarily leukocyte-rich fluid by separating leukocytes from other desirable constituents 15 of the blood, and advance the leukocyte-rich fluid with any undesirable components to the fluid receiving device 30. It should also be appreciated that, in embodiments in which a biological fluid 16 other than blood is being scanned, the components which are separated during presorting will by definition be comprised of different components than with blood. For example, in embodiments in which the biological fluid 16 is comprised of saliva, urine, cerebrospinal fluid, lymphatic fluids, or leukapheresis extracts, other constituents of the biological fluid 16 may be separated than the exemplary components (leukocytes, etc.) of blood. As another example, other components of the biological fluid 16 may be separated in sepsis-like use cases.

The one or more undesirable constituents 14 may be comprised of circulating tumor cells and pathogens. The fluid receiving device 30 may be comprised of one or more microfluidic channels 31. The fluid receiving device 30 may be comprised of a plurality of microwells, such as a plurality of microwells arranged in a microwell array 32. The scanner 70 may be adapted to scan each of the plurality of microwells of the microwell array 32.

The fluid receiving device 30 may be comprised of a microfluidic droplet generator 34. In such an embodiment, a droplet generator 34 may be utilized to encapsulate cells 18 into droplets 39, with each of the droplets 39 being scanned by the scanner 70. The droplet generator 34 may include a dispersed phase channel 35 and one or more continuous phase channels 36 which converge at a juncture 37 in which the cells 18 are encapsulated into the droplets 39. The droplets 39 including the encapsulated cells 18 may then be routed through a scanning channel 38 in which each such droplet 39 or groups of droplets 39 are scanned by the scanner 70.

The valve 40 may comprise a plurality of well valves 40 in one-to-one fluid communication with the plurality of microwells of the microwell array 32. The control unit 80 is operatively connected to the well valve 40 of each of the plurality of microwells of the microwell array 32. In some example embodiments, pipettes could be utilized to extract contents of a microwell. In other embodiments, multiple wells in an array 32 could share a single valve 40.

In another exemplary embodiment of a biological fluid filtration system 10, the fluid receiving device 30 is comprised of a microfluidic channel 31. In some embodiments, the fluid receiving device 30 is comprised of a plurality of microfluidic channels 31. The plurality of microfluidic channels 31 may be arranged in parallel or in series. The scanner 70 may be adapted to scan each of the plurality of microfluidic channels 31. The valve 40 may comprise a plurality of channel valves 40 in one-to-one fluid communication with the plurality of microfluidic channels 31. The control unit 80 may be operatively connected to the channel valve 40 of each of the plurality of microfluidic channels 31. The valve 40 may comprise a second outlet 43 in fluid communication with the return path 60.

The return path 60 may comprise a return channel that is fluidly connected 7 to the biological fluid source 17 such that filtered biological fluid 16 may be returned to the patient 12. In some embodiments, a drug infuser 130 may be fluidly connected to the return path 60 so as to introduce various drugs or treatments in the return path 60 to treat the patient 12. The drug infuser 130 may comprise a reservoir containing a volume of a drug or treatment that is fluidly connected to the return path 60. The drug infuser 130 may utilize valves, pumps, sensors, and the like to control the dosage infused within the return path 60.

In some embodiments, a reprocessing path 62 may be included so as to allow reprocessing of biological fluids 16 multiple times. In such an embodiment, the reprocessing path 62 may be fluidly connected back to the fluid receiving device 30 such that processed biological fluid 16 may be redirected back to the fluid receiving device 30 for additional processing. It should be appreciated that the reprocessing path 62 may be included in addition to the return path 60, such that certain samples of biological fluid 16 may be returned to the patient 12, and certain other samples of biological fluid 16 may instead be returned to the fluid receiving device 30 for additional scanning.

In another exemplary embodiment, a method of filtering a biological fluid 16 using the biological fluid filtration system 10 comprises the steps of: directing the biological fluid 16 to the fluid receiving device 30; optically scanning the biological fluid 16 within the fluid receiving device 30 by the scanner 70 to generate the scanned data 90 of the biological fluid 16; comparing the scanned data 90 of the biological fluid 16 with the reference data 91 by the control unit 80; returning the biological fluid 16 to the biological fluid source 17 if the scanned data 90 includes only desirable constituents 15 meeting the criteria of desirable constituents 15; and isolating the biological fluid 16 from the biological fluid source 17 if the scanned data 90 of the biological fluid 16 includes one or more undesirable constituents 14 not meeting the criteria of desirable constituents 15.

The method may comprise a therapeutic method and the biological fluid source 17 may comprise an individual patient 12 having a wide range of conditions, such as but not limited to cancer or infection with various pathogens. The method may further comprise obtaining a sample of biological fluid 16 of the individual patient 12, wherein the reference data 91 is generated from the sample.

In another exemplary embodiment, the method may further comprise obtaining samples of biological fluid 16 of one or more individuals other than the individual patient 12, wherein the reference data 91 is generated from the samples of biological fluid 16 of the one or more individuals other than the individual patient 12. The method may further comprise the step of performing diagnostics on the undesirable constituents 14.

In another exemplary embodiment, a method of filtering a biological fluid 16 comprises the steps of: receiving the biological fluid 16 from a biological fluid source 17 by a receiver path 20; transferring the biological fluid 16 from the receiver path 20 to a fluid receiving device 30; optically scanning the biological fluid 16 within the fluid receiving device 30 by a scanner 70 so as to create a scanned data 90 of the biological fluid 16; comparing the scanned data 90 of the biological fluid 16 with a reference data 91 by a control unit 80, wherein the reference data 91 comprises criteria including images and/or morphological parameters of desirable constituents 15; returning the biological fluid 16 to the biological fluid source 17 by a return path 60 if the scanned data 90 of the biological fluid 16 includes only desirable constituents 15 meeting the criteria of desirable constituents 15; and isolating the biological fluid 16 from the biological fluid source 17 by an isolation path 50 if the scanned data 90 of the biological fluid 16 includes one or more undesirable constituents 14 not meeting the criteria of desirable constituents 15. The reference data 91 may include data representative of desirable constituents 15.

In another exemplary embodiment of the method of filtering a biological fluid 16 using the biological fluid filtration system 10, the reference data 91 includes criteria of optic artifacts, and further steps may be performed comprising returning the biological fluid 16 to the biological fluid source 17 by a return path 60 if the scanned data 90 of the biological fluid 16 includes only desirable constituents 15 meeting the criteria of optic artifacts or the criteria of desirable constituents 15, and isolating the biological fluid 16 from the biological fluid source 17 by an isolation path 50 if the scanned data 90 of the biological fluid 16 includes one or more undesirable constituents 14 not meeting the criteria of optic artifacts or the criteria of desirable constituents 15.

In another exemplary embodiment of the method of filtering a biological fluid 16 using the biological fluid filtration system 10, the reference data 91 includes criteria including images and/or morphological parametric data representative of designated pathogens, and further steps may be performed comprising returning the biological fluid 16 to the biological fluid source 17 by a return path 60 if the scanned data 90 of the biological fluid 16 includes only desirable constituents 15 meeting the criteria of optic artifacts/pathogens or the criteria of desirable constituents 15, and isolating the biological fluid 16 from the biological fluid source 17 by an isolation path 50 if the scanned data 90 of the biological fluid 16 includes one or more undesirable constituents 14 not meeting the criteria of optic artifacts/pathogens or the criteria of desirable constituents 15.

The reference data 91 may include image data or morphological characteristics representative of healthy blood constituents. By way of example and without limitation, the reference data 91 may include data representative of erythrocytes, leukocytes, or thrombocytes.

In another exemplary embodiment of the method of filtering a biological fluid 16 using the biological fluid filtration system 10, the method may further comprise the steps of: sorting the biological fluid 16 from the receiver path 20 to separate leukocytes from other desirable constituents 15 of the biological fluid 16 to generate a leukocyte-rich fluid, and transferring the leukocyte-rich fluid to the fluid receiving device 30. The one or more undesirable constituents 14 may be comprised of circulating tumor cells, clusters thereof, or various other pathogens.

In another exemplary embodiment of the method of filtering a biological fluid 16 using the biological fluid filtration system 10, each of the plurality of microwells of the microwell array 32 may comprise a well valve 40 having a first port fluidly connected to the isolation path 50 and a second port fluidly connected to the return path 60. In other embodiments, each of the plurality of microwells of the microwell array 32 is fluidly connected via a well valve 40 having a single port, with the port being fluidly and selectively connected to both the return path 60 and the isolation path 50.

The control unit 80 may be operatively connected to the well valve 40 of each of the plurality of microwells of the microwell array 32. The fluid receiving device 30 may be comprised of a microfluidic channel 31 or a plurality of microfluidic channels 31. The plurality of microfluidic channels 31 may be arranged in a parallel series. The scanner 70 may be adapted to scan each of the plurality of microfluidic channels 31. In some example embodiments, pipettes could be utilized to extract contents of a microwell. In other embodiments, multiple wells in an array could share a single valve 40.

In another exemplary embodiment of the method of filtering a biological fluid 16 using the biological fluid filtration system 10, each of the plurality of microfluidic channels 31 may comprise a channel valve 40 having a first port fluidly connected to the isolation path 50 and a second port fluidly connected to the return path 60. The control unit 80 may be operatively connected to the channel valve 40 of each of the plurality of microfluidic channels 31.

In another exemplary embodiment, a method of filtering a biological fluid 16 comprises the steps of: receiving the biological fluid 16 from a biological fluid source 17; separating the biological fluid 16 into a first portion, a second portion, and a third portion, the first portion comprising only desirable constituents 15, the second portion comprising a mix of undesirable and desirable constituents 14, 15, and the third portion comprising only undesirable constituents 14; returning the first portion of the biological fluid 16 to the biological fluid source 17 by a return path 60; isolating the third portion of the biological fluid 16 from the biological fluid source 17 by an isolation path 50; transferring the second portion of the biological fluid 16 to a fluid receiving device 30; optically scanning the second portion of the biological fluid 16 within the fluid receiving device 30 by a scanner 70 so as to create a scanned data 90 of the second portion of the biological fluid 16; comparing the scanned data 90 of the second portion of the biological fluid 16 with a reference data 91 by a control unit 80, the reference data 91 comprising criteria of desirable constituents 15; returning the second portion of the biological fluid 16 to the biological fluid source 17 by the return path 60 if the scanned data 90 of the biological fluid 16 includes only desirable constituents 15 meeting the criteria of desirable constituents 15; and isolating the second portion of the biological fluid 16 from the biological fluid source 17 by the isolation path 50 if the scanned data 90 of the biological fluid 16 includes one or more constituents 13 not meeting the criteria of desirable constituents 15. The step of separating the biological fluid 16 may be comprised of dielectric sorting, Dean flow fractionation, or hemodynamic properties.

In another exemplary embodiment of the method of filtering a biological fluid 16 using the biological fluid filtration system 10, multiple scanners 70 may be used simultaneously to optically scan the fluid receiving device 30. In such an embodiment, different areas, such as different microwells of a microwell array 32, different microfluidic channels 31, or different droplets 39 of a droplet generator 34, may be optically scanned by a plurality of scanners 70 rather than a singular scanner 70.

In another exemplary embodiment of the method of filtering a biological fluid 16 using the biological fluid filtration system 10, the fluid receiving device 30 may be scanned multiple times by the scanner 70 before transfer to the return path 60. Such an embodiment will utilize multiple scans to ensure and verify that the biological fluid 16 being scanned does not include any undesirable constituents 14 prior to be released to the return path 60. Such an embodiment will reduce the risks of inaccurate scans by verifying through multiple scans prior to releasing the biological fluid 16.

Unless otherwise defined, all technical and scientific terms used herein have the same meaning as commonly understood by one of ordinary skill in the art to which this invention belongs. Although methods and materials similar to or equivalent to those described herein can be used in the practice or testing of the biological fluid filtration system, suitable methods and materials are described above. All patent applications, patents, and printed publications cited herein are incorporated herein by reference in their entireties, except for any definitions, subject matter disclaimers or disavowals, and except to the extent that the incorporated material is inconsistent with the express disclosure herein, in which case the language in this disclosure controls. The biological fluid filtration system may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. A biological fluid filtration system, comprising:
    a fluid receiving device adapted to receive a biological fluid;
    a valve comprising an inlet, a first outlet, and a second outlet, wherein the inlet of the valve is fluidly connected to the fluid receiving device;
    a scanner configured to scan the biological fluid within the fluid receiving device to produce a scanned data relating to the biological fluid within the fluid receiving device; and
    a control unit in communication with the scanner and the valve, wherein the control unit is configured to receive the scanned data from the scanner, and wherein the control unit is configured to control the valve based on the scanned data from the scanner;

wherein the control unit is configured to compare the scanned data to a reference data, wherein the reference data includes a characteristic of at least one desirable constituent and a characteristic of an optical artifact;

wherein the control unit is configured to control the valve to (a) direct the biological fluid through the second outlet if the control unit determines that the scanned data indicates a presence of only the at least one desirable constituent and the optical artifact within the biological fluid or (b) direct the biological fluid through the first outlet if the control unit determines that the scanned data does not indicate a presence of only the at least one desirable constituent and the optical artifact within the biological fluid.

2. The biological fluid filtration system of claim 1, wherein the optical artifact is comprised of a halo.

3. The biological fluid filtration system of claim 1, wherein the optical artifact is comprised of an air bubble.

4. The biological fluid filtration system of claim 1, wherein the optical artifact is comprised of blurring.

5. The biological fluid filtration system of claim 1, wherein the at least one desirable constituent includes a healthy cell.

6. The biological fluid filtration system of claim 1, wherein the at least one desirable constituent includes a benign bacterium.

7. The biological fluid filtration system of claim 1, wherein the reference data includes a characteristic of an undesirable constituent.

8. The biological fluid filtration system of claim 7, wherein the control unit is configured to control the valve to (a) direct the biological fluid through the first outlet if the control unit determines that the scanned data indicates a presence of the undesirable constituent within the biological fluid or (b) direct the biological fluid through the second outlet if the control unit determines that the scanned data does not indicate a presence of the undesirable constituent within the biological fluid.

9. The biological fluid filtration system of claim 8, wherein the control unit is configured to determine that the scanned data indicates the presence of the undesirable constituent when the control unit detects the undesirable constituent within the scanned data.

10. The biological fluid filtration system of claim 8, wherein the control unit is configured to determine that the scanned data indicates the presence of the undesirable constituent when the control unit detects an unknown constituent within the scanned data.

11. The biological fluid filtration system of claim 1, wherein the characteristic of at least one desirable constituent is comprised of a size.

12. A biological fluid filtration system, comprising:
a fluid receiving device adapted to receive a biological fluid;
a valve comprising an inlet, a first outlet, and a second outlet, wherein the inlet of the valve is fluidly connected to the fluid receiving device;
a scanner configured to scan the biological fluid within the fluid receiving device to produce a scanned data relating to the biological fluid within the fluid receiving device; and
a control unit in communication with the scanner and the valve, wherein the control unit is configured to receive the scanned data from the scanner, and wherein the control unit is configured to control the valve based on the scanned data from the scanner;

wherein the control unit is configured to compare the scanned data to a reference data, wherein the reference data includes an image of at least one desirable constituent and an image of an optical artifact;

wherein the control unit is configured to control the valve to (a) direct the biological fluid through the second outlet if the control unit determines that the scanned data indicates a presence of only the at least one desirable constituent and the optical artifact within the biological fluid or (b) direct the biological fluid through the first outlet if the control unit determines that the scanned data does not indicate a presence of only the at least one desirable constituent and the optical artifact within the biological fluid.

13. The biological fluid filtration system of claim 12, wherein the optical artifact is comprised of a halo.

14. The biological fluid filtration system of claim 12, wherein the optical artifact is comprised of an air bubble.

15. The biological fluid filtration system of claim 12, wherein the optical artifact is comprised of blurring.

16. The biological fluid filtration system of claim 12, wherein the at least one desirable constituent includes a healthy cell.

17. The biological fluid filtration system of claim 12, wherein the at least one desirable constituent includes a benign bacterium.

18. The biological fluid filtration system of claim 12, wherein the reference data includes an image of an undesirable constituent.

19. The biological fluid filtration system of claim 18, wherein the control unit is configured to control the valve to (a) direct the biological fluid through the first outlet if the control unit determines that the scanned data indicates a presence of the undesirable constituent within the biological fluid or (b) direct the biological fluid through the second outlet if the control unit determines that the scanned data does not indicate the presence of the undesirable constituent within the biological fluid.

20. The biological fluid filtration system of claim 19, wherein the control unit is configured to determine that the scanned data indicates the presence of the undesirable constituent when the control unit detects the undesirable constituent within the scanned data.

21. The biological fluid filtration system of claim 20, wherein the control unit is configured to determine that the scanned data indicates the presence of the undesirable constituent when the control unit detects an unknown constituent within the scanned data.

* * * * *